United States Patent
Brodt et al.

(10) Patent No.: US 10,538,575 B2
(45) Date of Patent: Jan. 21, 2020

(54) SOLUBLE IGF RECEPTOR FC FUSION PROTEINS AND USES THEREOF

(71) Applicants: THE ROYAL INSTITUTION FOR THE ADVANCEMENT OF LEARNING/MCGILL UNIVERSITY, Montreal (CA); THE NATIONAL RESEARCH COUNCIL OF CANADA, Ottawa (CA)

(72) Inventors: Pnina Brodt, Montreal (CA); Bernard Massie, Montreal (CA); Traian Sulea, Kirkland (CA)

(*) Notice: Subject to any disclaimer, the term of this patent is extended or adjusted under 35 U.S.C. 154(b) by 109 days.

(21) Appl. No.: 14/365,250

(22) PCT Filed: Dec. 14, 2012

(86) PCT No.: PCT/CA2012/050899
§ 371 (c)(1),
(2) Date: Jun. 13, 2014

(87) PCT Pub. No.: WO2013/086636
PCT Pub. Date: Jun. 20, 2013

(65) Prior Publication Data
US 2015/0044209 A1    Feb. 12, 2015

Related U.S. Application Data

(60) Provisional application No. 61/576,034, filed on Dec. 15, 2011.

(51) Int. Cl.
| | | |
|---|---|---|
| A61K 38/16 | (2006.01) | |
| C07K 14/71 | (2006.01) | |
| A61K 35/28 | (2015.01) | |
| A61K 39/395 | (2006.01) | |
| A61K 45/06 | (2006.01) | |
| C07K 16/22 | (2006.01) | |
| A61K 48/00 | (2006.01) | |
| A61K 35/12 | (2015.01) | |
| A61K 39/00 | (2006.01) | |

(52) U.S. Cl.
CPC .......... *C07K 14/71* (2013.01); *A61K 35/28* (2013.01); *A61K 39/3955* (2013.01); *A61K 45/06* (2013.01); *C07K 16/22* (2013.01); *A61K 48/00* (2013.01); *A61K 2035/124* (2013.01); *A61K 2039/505* (2013.01); *A61K 2039/515* (2013.01); *C07K 2319/01* (2013.01)

(58) Field of Classification Search
None
See application file for complete search history.

(56) References Cited

U.S. PATENT DOCUMENTS

| | | | | |
|---|---|---|---|---|
| 7,323,549 B2* | 1/2008 | Lauder | ............... | A61K 38/2046 530/350 |
| 7,871,611 B2* | 1/2011 | Calzone | ................. | C07K 16/22 424/130.1 |
| 2010/0047243 A1 | 2/2010 | Burden et al. | | |
| 2011/0152173 A1 | 6/2011 | Lofquist et al. | | |
| 2011/0262430 A1 | 10/2011 | Ellis | | |

FOREIGN PATENT DOCUMENTS

| | | |
|---|---|---|
| WO | 2008/108986 A2 | 9/2008 |
| WO | 2008108986 A2 | 9/2008 |
| WO | 2009/016164 A1 | 2/2009 |
| WO | 2009016164 A1 | 2/2009 |
| WO | 2010/003118 A1 | 1/2010 |
| WO | 2010003108 A2 | 1/2010 |
| WO | 2010012088 A1 | 2/2010 |
| WO | 2010012088 A8 | 2/2010 |
| WO | 2010/037837 A2 | 4/2010 |
| WO | 2010037837 A2 | 4/2010 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Benouchan et al. (2005). Anti-angiogenic strategies for cancer therapy (review). Intl. J. Oncology. 27:563-571.*
Shumizu et al. (2005). Antineovascular therapy, a novel antiangiogenic approach. Expert. Opin. Ther. Targets. 9(1):63-76.*
Surinya KH et al. An investigation of the ligand binding properties and negative cooperativity of soluble insulin-like growth factor receptors. J. Biol. Chem. Feb. 29, 2008, vol. 283, No. 9, pp. 5355-5363. ISSN 0008-5472.
Wang N et al. Autologous bone marrow stromal cells genetically engineered to secrete an IGF-I receptor decoy prevent the growth of liver metastases. Mol. Ther. Jul. 2009, vol. 17, No. 7, pp. 1241-1249. ISSN 1525-0024.
Samani AA et al. Loss of tumorigenicity and metastatic potential in carcinoma cells expressing the extracellular domain of the type 1 insulin-like growth factor receptor. Cancer Res. May 15, 2004, vol. 64, No. 10, pp. 3380-3385. ISSN 0008-5472.
Ni Wang et al., Autologous Bone Marrow Stromal Cells Genetically Engineered to Secrete an IGF-I Receptor Decoy Prevent the Growth of Liver Metastases, Mol Ther. Jul. 2009;17(7):1241-9. doi: 10.1038/mt.2009.82. Epub Apr. 14, 2009.
Samani AA et al., Loss of tumorigenicity and metastatic potential in carcinoma cells expressing the extracellylar domain of the type 1 insulin-like growth factor receptor, Cancer Res. May 15, 2004;64(10):3380-5.

* cited by examiner

*Primary Examiner* — Christine J Saoud
*Assistant Examiner* — Jon M Lockard
(74) *Attorney, Agent, or Firm* — Norton Rose Fulbright Canada; Marie-Helene Rochon

(57) ABSTRACT

There are described herein novel soluble IGF receptor Fc fusion proteins and compositions and methods of use thereof for treating angiogenesis associated disorders and malignant disease, such as cancer and metastasis, wherein the fusion proteins bind specifically to IGF-1 or IGF-2.

13 Claims, 37 Drawing Sheets

Specification includes a Sequence Listing.

A

B

- Biantennary
- Triantennary
- Tetraantennary
- Tetraantennary + LacNAc Repeat
- Hex5HexNAc2
- Hex6HexNAc2
- Hex7HexNAc2
- Hex8HexNAc2
- Hex9HexNAc2

A

B

B
- Control
- 10ng/ml IGF-I
- IGF-I+Trap D
- IGF-I+Trap E

A

B

A

B

A

B

C

D

A

Non-treated                              Trap- treated

B

A

B

A

Non- treated    IGF- Trap- treated

B

A

B

A

B

A

B

C

* IGF1R-hFc-IgG1 homodimer (Fc-β-α-α-β-Fc) in non-reducing form (420-440kDa)

** IGF1R-hFc-IgG1 monomer (Fc-β-α) in partial-reducing form (210-220kDa)

*** IGF1R-hFc-IgG1 monomer (Fc-β & α) in completely reducing form generate a Fc-β chain (80-90kDa) and α-chain (130kDa non detectable with Cy5-goat-anti-human IgG)

SEQUENCE LISTING

<160> NUMBER OF SEQ ID NOS: 18

<210> SEQ ID NO 1
<211> LENGTH: 933
<212> TYPE: PRT
<213> ORGANISM: Artificial Sequence
<220> FEATURE:
<223> OTHER INFORMATION: sIGF1R933 protein sequence

<400> SEQUENCE: 1

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
       35                40                45

Leu Glu Asn Cys Thr Val Ile Glu Gly Tyr Leu His Ile Leu Leu Ile
 50              55                  60

Ser Lys Ala Glu Asp Tyr Arg Ser Tyr Arg Phe Pro Lys Leu Thr Val
 65          70              75                  80

Ile Thr Glu Tyr Leu Leu Leu Phe Arg Val Ala Gly Leu Glu Ser Leu
             85              90                  95

Gly Asp Leu Phe Pro Asn Leu Thr Val Ile Arg Gly Trp Lys Leu Phe
            100             105             110

Tyr Asn Tyr Ala Leu Val Ile Phe Glu Met Thr Asn Leu Lys Asp Ile
            115             120             125

Gly Leu Tyr Asn Leu Arg Asn Ile Thr Arg Gly Ala Ile Arg Ile Glu
            130             135             140

Lys Asn Ala Asp Leu Cys Tyr Leu Ser Thr Val Asp Trp Ser Leu Ile
145             150             155             160

Leu Asp Ala Val Ser Asn Asn Tyr Ile Val Gly Asn Lys Pro Pro Lys
                165             170             175

Glu Cys Gly Asp Leu Cys Pro Gly Thr Met Glu Glu Lys Pro Met Cys
            180             185             190

Glu Lys Thr Thr Ile Asn Asn Glu Tyr Asn Tyr Arg Cys Trp Thr Thr
            195             200             205

Asn Arg Cys Gln Lys Met Cys Pro Ser Thr Cys Gly Lys Arg Ala Cys
210             215             220

Thr Glu Asn Asn Glu Cys Cys His Pro Glu Cys Leu Gly Ser Cys Ser
225             230             235             240

Ala Pro Asp Asn Asp Thr Ala Cys Val Ala Cys Arg His Tyr Tyr Tyr
                245             250             255

Ala Gly Val Cys Val Pro Ala Cys Pro Pro Asn Thr Tyr Arg Phe Glu
            260             265             270

Gly Trp Arg Cys Val Asp Arg Asp Phe Cys Ala Asn Ile Leu Ser Ala
            275             280             285

Glu Ser Ser Asp Ser Glu Gly Phe Val Ile His Asp Gly Glu Cys Met
            290             295             300

Gln Glu Cys Pro Ser Gly Phe Ile Arg Asn Gly Ser Gln Ser Met Tyr
305             310             315             320

Cys Ile Pro Cys Glu Gly Pro Cys Pro Lys Val Cys Glu Glu Glu Lys
            325             330             335

Lys Thr Lys Thr Ile Asp Ser Val Thr Ser Ala Gln Met Leu Gln Gly
            340             345             350

Cys Thr Ile Phe Lys Gly Asn Leu Leu Ile Asn Ile Arg Arg Gly Asn
            355             360             365

Asn Ile Ala Ser Glu Leu Glu Asn Phe Met Gly Leu Ile Glu Val Val
370             375             380

Thr Gly Tyr Val Lys Ile Arg His Ser His Ala Leu Val Ser Leu Ser
385             390             395             400

Phe Leu Lys Asn Leu Arg Leu Ile Leu Gly Glu Glu Gln Leu Glu Gly
            405             410             415

Asn Tyr Ser Phe Tyr Val Leu Asp Asn Gln Asn Leu Gln Gln Leu Trp
            420             425             430

Asp Trp Asp His Arg Asn Leu Thr Ile Lys Ala Gly Lys Met Tyr Phe
            435             440             445

-continued

```
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
    610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
    690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
        755                 760                 765
Glu Glu Leu Glu Thr Glu Tyr Pro Phe Phe Glu Ser Arg Val Asp Asn
    770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
        835                 840                 845
Phe Leu Lys Trp Pro Glu Pro Glu Asn Pro Asn Gly Leu Ile Leu Met
    850                 855                 860
Tyr Glu Ile Lys Tyr Gly Ser Gln Val Glu Asp Gln Arg Glu Cys Val
```

```
                865                 870                 875                 880
            Ser Arg Gln Glu Tyr Arg Lys Tyr Gly Gly Ala Lys Leu Asn Arg Leu
                            885                 890                 895
            Asn Pro Gly Asn Tyr Thr Ala Arg Ile Gln Ala Thr Ser Leu Ser Gly
                        900                 905                 910
            Asn Gly Ser Trp Thr Asp Pro Val Phe Phe Tyr Val Gln Ala Lys Thr
                    915                 920                 925
            Gly Tyr Glu Asn Phe
                930

<210> SEQ ID NO 2
<211> LENGTH: 2799
<212> TYPE: DNA
<213> ORGANISM: Homo sapiens

<400> SEQUENCE: 2
atgaagtctg gctccggagg agggtccccg acctcgctgt gggggctcct gtttctctcc        60
gccgcgctct cgctctggcc gacgagtgga gaaatctgcg gccaggcat  cgacatccgc       120 aacgactatc agcagctgaa gcgcctggag aactgcacgg tgatcgaggg ctacctccac       180
atcctgctca tctccaaggc cgaggactac cgcagctacc gcttcccaa  gctcacggtc       240 attaccgagt acttgctgct gttccgagtg gctggcctcg agagcctcgg agacctcttc       300
cccaacctca cggtcatccg cggctggaaa ctcttctaca actacgccct ggtcatcttc       360
gagatgacca atctcaagga tattgggctt acaacctga  ggaacattac tcgggggggcc      420 atcaggattg agaaaaatgc tgacctctgt tacctctcca ctgtggactg gtccctgatc       480
ctggatgcgg tgtccaataa ctacattgtg gggaataagc ccccaaagga atgtggggac       540
ctgtgtccag ggaccatgga ggagaagccg atgtgtgaga gaccaccat  caacaatgag       600 tacaactacc gctgctggac cacaaaccgc tgccagaaaa tgtgcccaag cacgtgtggg       660
aagcgggcgt gcaccgagaa caatgagtgc tgccaccccg agtgcctggg cagctgcagc       720
gcgcctgaca acgacacggc ctgtgtagct tgccgccact actactatgc cggtgtctgt       780
gtgcctgcct gcccgcccaa cacctacagg tttgagggct ggcgctgtgt ggaccgtgac       840
ttctgcgcca acatcctcag cgccgagagc agcgactccg aggggtttgt gatccacgac       900
ggcgagtgca tgcaggagtg cccctcgggc ttcatccgca acggcagcca gagcatgtac       960
tgcatccctt gtgaaggtcc ttgcccgaag gtctgtgagg aagaaaagaa aacaaagacc      1020
attgattctg ttacttctgc tcagatgctc caaggatgca ccatcttcaa gggcaatttg      1080
ctcattaaca tccgacgggg gaataacatt gcttcagagc tggagaactt catggggctc      1140
atcgaggtgg tgacgggcta cgtgaagatc cgccattctc atgccttggt ctccttgtcc      1200
ttcctaaaaa accttcgcct catcctagga gaggagcagc tagaagggaa ttactccttc      1260
tacgtcctcg acaaccagaa cttgcagcaa ctgtgggact gggaccaccg caacctgacc      1320
atcaaagcag ggaaaatgta ctttgctttc aatcccaaat atgtgtttc  gaaatttac       1380 cgcatggagg aagtgacggg gactaaaggg cgccaaagca agggggacat aaacaccagg      1440
aacaacgggg agagagcctc ctgtgaaagt gacgtcctgc atttcacctc caccaccacg      1500
tcgaagaatc gcatcatcat aacctggcac cggtaccggc ccctgactca gggatctc       1560 atcagcttca ccgtttacta caaggaagca cccttaag   atgtcacaga gtatgatggg      1620
caggatgcct gcggctccaa cagctggaac atggtggacg tggacctccc gcccaacaag      1680
gacgtggagc ccggcatctt actacatggg ctgaagcct  ggactcagta cgccgtttac      1740
```

-continued

```
gtcaaggctg tgaccctcac catggtggag aacgaccata tccgtggggc caagagtgag    1800
atcttgtaca ttcgcaccaa tgcttcagtt ccttccattc ccttggacgt tctttcagca    1860
tcgaactcct cttctcagtt aatcgtgaag tggaaccctc cctctctgcc aacggcaac     1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca catcaccga cccggaagag ctggagacag agtacccttt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttc                            2799
```

<210> SEQ ID NO 3
<211> LENGTH: 4104
<212> TYPE: DNA
<213> ORGANISM: Homo sapiens
<220> FEATURE:
<223> OTHER INFORMATION: Full length IGF-IR

<400> SEQUENCE: 3

```
atgaagtctg gctccggagg agggtccccg acctcgctgt ggggctcct gtttctctcc      60
gccgcgctct cgctctggcc gacgagtgga gaaatctgcg gccaggcat cgacatccgc     120
aacgactatc agcagctgaa gcgcctggag aactgcacgg tgatcgaggg ctacctccac    180
atcctgctca tctccaaggc cgaggactac cgcagctacc gcttcccaa gctcacggtc    240
attaccgagt acttgctgct gttccgagtg gctggcctcg agagcctcgg agacctcttc    300
cccaacctca cggtcatccg cggctggaaa ctcttctaca actacgccct ggtcatcttc    360
gagatgacca atctcaagga tattgggctt acaacctga ggaacattac tcgggggggcc    420
atcaggattg agaaaaatgc tgacctctgt tacctctcca ctgtggactg gtccctgatc    480
ctggatgcgg tgtccaataa ctacattgtg gggaataagc ccccaaagga atgtggggac    540
ctgtgtccag ggaccatgga ggagaagccg atgtgtgaga agaccaccat caacaatgag    600
tacaactacc gctgctggac cacaaaccgc tgccagaaaa tgtgcccaag cacgtgtggg    660
aagcgggcgt gcaccgagaa caatgagtgc tgccacccg agtgcctggg cagctgcagc    720
gcgcctgaca acgacacggc ctgtgtagct tgccgccact actactatgc cggtgtctgt    780
gtgcctgcct gccgccaa cacctacagg tttgagggct ggcgctgtgt ggaccgtgac    840
ttctgcgcca acatcctcag cgccgagagc agcgactccg aggggtttgt gatccacgac    900
ggcgagtgca tgcaggagtg cccctcgggc ttcatccgca acggcagcca gagcatgtac    960
```

```
tgcatccctt gtgaaggtcc ttgcccgaag gtctgtgagg aagaaaagaa aacaaagacc      1020
attgattctg ttacttctgc tcagatgctc caaggatgca ccatcttcaa gggcaatttg      1080
ctcattaaca tccgacgggg gaataacatt gcttcagagc tggagaactt catggggctc      1140
atcgaggtgg tgacgggcta cgtgaagatc cgccattctc atgccttggt ctccttgtcc      1200
ttcctaaaaa accttcgcct catcctagga gaggagcagc tagaagggaa ttactccttc      1260
tacgtcctcg acaaccagaa cttgcagcaa ctgtgggact gggaccaccg caacctgacc      1320
atcaaagcag ggaaaatgta ctttgctttc aatcccaaat tatgtgtttc cgaaatttac      1380
cgcatggagg aagtgacggg gactaaaggg cgccaaagca aagggacat aaacaccagg       1440 aacaacgggg agagagcctc ctgtgaaagt gacgtcctgc atttcacctc caccaccacg      1500
tcgaagaatc gcatcatcat aacctggcac cggtaccggc cccctgacta cagggatctc      1560
atcagcttca ccgtttacta caaggaagca ccctttaaga atgtcacaga gtatgatggg      1620
caggatgcct gcggctccaa cagctggaac atggtggacg tggacctccc gcccaacaag      1680
gacgtggagc ccggcatctt actacatggg ctgaagccct ggactcagta cgccgtttac      1740
gtcaaggctg tgaccctcac catggtggag aacgaccata tccgtggggc caagagtgag      1800
atcttgtaca ttcgcaccaa tgcttcagtt ccttccattc ccttggacgt tctttcagca      1860
tcgaactcct cttctcagtt aatcgtgaag tggaaccctc cctctctgcc caacggcaac      1920
ctgagttact acattgtgcg ctggcagcgg cagcctcagg acggctacct ttaccggcac      1980
aattactgct ccaaagacaa aatccccatc aggaagtatg ccgacggcac catcgacatt      2040
gaggaggtca cagagaaccc caagactgag gtgtgtggtg gggagaaagg gccttgctgc      2100
gcctgcccca aaactgaagc cgagaagcag gccgagaagg aggaggctga ataccgcaaa      2160
gtctttgaga atttcctgca caactccatc ttcgtgccca gacctgaaag gaagcggaga      2220
gatgtcatgc aagtggccaa caccaccatg tccagccgaa gcaggaacac cacggccgca      2280
gacacctaca acatcaccga cccggaagag ctggagacag agtacccttt ctttgagagc      2340
agagtggata caaggagag aactgtcatt tctaaccttc ggcctttcac attgtaccgc      2400
atcgatatcc acagctgcaa ccacgaggct gagaagctgg gctgcagcgc ctccaacttc      2460
gtctttgcaa ggactatgcc cgcagaagga gcagatgaca ttcctgggcc agtgacctgg      2520
gagccaaggc ctgaaaactc catctttta aagtggccgg aacctgagaa tcccaatgga      2580
ttgattctaa tgtatgaaat aaaatacgga tcacaagttg aggatcagcg agaatgtgtg      2640
tccagacagg aatacaggaa gtatggaggg gccaagctaa accggctaaa cccggggaac      2700
tacacagccc ggattcaggc cacatctctc tctgggaatg ggtcgtggac agatcctgtg      2760
ttcttctatg tccaggccaa aacaggatat gaaaacttca tccatctgat catcgctctg      2820
cccgtcgctg tcctgttgat cgtgggaggg ttggtgatta tgctgtacgt cttccataga      2880
aagagaaata acagcaggct ggggaatgga gtgctgtatg cctctgtgaa cccggagtac      2940
ttcagcgctg ctgatgtgta cgttcctgat gagtgggagg tggctcggga agagatcacc      3000
atgagccggg aacttgggca ggggtcgttt gggatggtct atgaaggagt tgccaagggt      3060
gtggtgaaag atgaacctga aaccagagtg gccattaaaa cagtgaacga ggccgcaagc      3120
atgcgtgaga ggattgagtt tctcaacgaa gcttctgtga tgaaggagtt caattgtcac      3180
catgtggtgc gattgctggg tgtggtgtcc caaggccagc caacactggt catcatggaa      3240
ctgatgacac ggggcgatct caaaagttat ctccggtctc tgaggccaga aatggagaat      3300
aatccagtcc tagcacctcc aagcctgagc aagatgattc agatggccgg agagattgca      3360
```

```
gacggcatgg catacctcaa cgccaataag ttcgtccaca gagaccttgc tgcccggaat    3420
tgcatggtag ccgaagattt cacagtcaaa atcggagatt ttggtatgac gcgagatatc    3480
tatgagacag actattaccg gaaaggaggg aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc aacgagcaa    3660 gtccttcgct tcgtcatgga gggcggcctt ctggacaagc agacaactg tcctgacatg    3720 ctgtttgaac tgatgcgcat gtgctggcag tataacccca agatgaggcc ttccttcctg    3780
gagatcatca gcagcatcaa agaggagatg gagcctggct ccgggaggt ctccttctac    3840 tacagcgagg agaacaagct gcccgagccg gaggagctgg acctggagcc agagaacatg    3900
gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac gggggccgca agaacgagcg ggccttgccg    4080
ctgccccagt cttcgacctg ctga                                          4104

<210> SEQ ID NO 4
<211> LENGTH: 1367
<212> TYPE: PRT
<213> ORGANISM: Homo sapiens
<220> FEATURE:
<223> OTHER INFORMATION: Full length IGF-IR

<400> SEQUENCE: 4

Met Lys Ser Gly Ser Gly Gly Gly Ser Pro Thr Ser Leu Trp Gly Leu
  1               5                  10                  15

Leu Phe Leu Ser Ala Ala Leu Ser Leu Trp Pro Thr Ser Gly Glu Ile
                 20                  25                  30

Cys Gly Pro Gly Ile Asp Ile Arg Asn Asp Tyr Gln Gln Leu Lys Arg
             35                  40                  45

Leu Glu Asn Cys Thr Val Ile Glu Gly Tyr Leu His Ile Leu Leu Ile
         50                  55                  60

Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220
```

-continued

```
Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
```

```
                645                 650                 655
Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
                755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn Phe Ile His Leu Ile Ile Ala Leu Pro Val Ala Val
            930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
            995                 1000                1005

Ser Phe Gly Met Val Tyr Glu Gly Val Ala Lys Gly Val Val Lys Asp
    1010                1015                1020

Glu Pro Glu Thr Arg Val Ala Ile Lys Thr Val Asn Glu Ala Ala Ser
1025                1030                1035                1040

Met Arg Glu Arg Ile Glu Phe Leu Asn Glu Ala Ser Val Met Lys Glu
                1045                1050                1055

Phe Asn Cys His His Val Val Arg Leu Leu Gly Val Val Ser Gln Gly
                1060                1065                1070
```

Gln Pro Thr Leu Val Ile Met Glu Leu Met Thr Arg Gly Asp Leu Lys
    1075                1080                1085

Ser Tyr Leu Arg Ser Leu Arg Pro Glu Met Glu Asn Asn Pro Val Leu
    1090                1095                1100

Ala Pro Pro Ser Leu Ser Lys Met Ile Gln Met Ala Gly Glu Ile Ala
1105                1110                1115                1120

Asp Gly Met Ala Tyr Leu Asn Ala Asn Lys Phe Val His Arg Asp Leu
                1125                1130                1135

Ala Ala Arg Asn Cys Met Val Ala Glu Asp Phe Thr Val Lys Ile Gly
            1140                1145                1150

Asp Phe Gly Met Thr Arg Asp Ile Tyr Glu Thr Asp Tyr Tyr Arg Lys
                1155                1160                1165

Gly Gly Lys Gly Leu Leu Pro Val Arg Trp Met Ser Pro Glu Ser Leu
    1170                1175                1180

Lys Asp Gly Val Phe Thr Thr Tyr Ser Asp Val Trp Ser Phe Gly Val
1185                1190                1195                1200

Val Leu Trp Glu Ile Ala Thr Leu Ala Glu Gln Pro Tyr Gln Gly Leu
                1205                1210                1215

Ser Asn Glu Gln Val Leu Arg Phe Val Met Glu Gly Gly Leu Leu Asp
            1220                1225                1230

Lys Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile Ser
    1250                1255                1260

Ser Ile Lys Glu Glu Met Glu Pro Gly Phe Arg Glu Val Ser Phe Tyr
1265                1270                1275                1280

Tyr Ser Glu Glu Asn Lys Leu Pro Glu Pro Glu Glu Leu Asp Leu Glu
                1285                1290                1295

Pro Glu Asn Met Glu Ser Val Pro Leu Asp Pro Ser Ala Ser Ser Ser
            1300                1305                1310

Ser Leu Pro Leu Pro Asp Arg His Ser Gly His Lys Ala Glu Asn Gly
    1315                1320                1325

Pro Gly Pro Gly Val Leu Val Leu Arg Ala Ser Phe Asp Glu Arg Gln
    1330                1335                1340

Pro Tyr Ala His Met Asn Gly Gly Arg Lys Asn Glu Arg Ala Leu Pro
1345                1350                1355                1360

Leu Pro Gln Ser Ser Thr Cys
            1365

<210> SEQ ID NO 5
<211> LENGTH: 2802
<212> TYPE: DNA
<213> ORGANISM: Artificial sequence
<220> FEATURE:
<223> OTHER INFORMATION: IGF1R from ATG to STOP

<400> SEQUENCE: 5
atgaagtctg gctccggagg agggtccccg acctcgctgt gggggctcct gtttctctcc      60
gccgcgctct cgctctggcc gacgagtgga gaaatctgcg gccaggcat cgacatccgc      120 aacgactatc agcagctgaa gcgcctggag aactgcacgg tgatcgaggg ctacctccac      180
atcctgctca tctccaaggc cgaggactac cgcagctacc gcttcccaa gctcacggtc      240 attaccgagt acttgctgct gttccgagtg gctggcctcg agagcctcgg agacctcttc      300
cccaacctca cggtcatccg cggctggaaa ctcttctaca actacgccct ggtcatcttc      360

```
gagatgacca atctcaagga tattgggctt tacaacctga ggaacattac tcgggggcc    420 atcaggattg agaaaaatgc tgacctctgt tacctctcca ctgtggactg gtccctgatc   480
ctggatgcgg tgtccaataa ctacattgtg gggataagc ccccaaagga atgtggggac    540
ctgtgtccag ggaccatgga ggagaagccg atgtgtgaga agaccaccat caacaatgag   600
tacaactacc gctgctggac cacaaaccgc tgccagaaaa tgtgcccaag cacgtgtggg   660
aagcgggcgt gcaccgagaa caatgagtgc tgccaccccg agtgcctggg cagctgcagc   720
gcgcctgaca acgacacggc ctgtgtagct tgccgccact actactatgc cggtgtctgt   780
gtgcctgcct gcccgcccaa cacctacagg tttgagggct ggcgctgtgt ggaccgtgac   840
ttctgcgcca acatcctcag cgccgagagc agcgactccg aggggtttgt gatccacgac   900
ggcgagtgca tgcaggagtg cccctcgggc ttcatccgca acggcagcca gagcatgtac   960
tgcatccctt gtgaaggtcc ttgcccgaag gtctgtgagg aagaaaagaa aacaaagacc   1020
attgattctg ttacttctgc tcagatgctc caaggatgca ccatcttcaa gggcaatttg   1080
ctcattaaca tccgacgggg gaataacatt gcttcagagc tggagaactt catggggctc   1140
atcgaggtgg tgacgggcta cgtgaagatc cgccattctc atgccttggt ctccttgtcc   1200
ttcctaaaaa accttcgcct catcctagga gaggagcagc tagaagggaa ttactccttc   1260
tacgtcctcg acaaccagaa cttgcagcaa ctgtgggact gggaccaccg caacctgacc   1320
atcaaagcag ggaaaatgta ctttgctttc aatcccaaat tatgtgtttc cgaaatttac   1380
cgcatggagg aagtgacggg gactaaaggg cgccaaagca aggggacat aaacaccagg    1440 aacaacgggg agagagcctc ctgtgaaagt gacgtcctgc atttcacctc caccaccacg   1500
tcgaagaatc gcatcatcat aacctggcac cggtaccggc cccctgacta cagggatctc   1560
atcagcttca ccgtttacta caaggaagca ccctttaaga atgtcacaga gtatgatggg   1620
caggatgcct gcggctccaa cagctggaac atggtggacg tggacctccc gcccaacaag   1680
gacgtggagc ccggcatctt actacatggg ctgaagccct ggactcagta cgccgtttac   1740
gtcaaggctg tgaccctcac catggtggag aacgaccata tccgtggggc caagagtgag   1800
atcttgtaca ttcgcaccaa tgcttcagtt ccttccattc ccttggacgt tctttcagca   1860
tcgaactcct cttctcagtt aatcgtgaag tggaaccctc cctctctgcc caacggcaac   1920
ctgagttact acattgtgcg ctggcagcgg cagcctcagg acggctacct ttaccggcac   1980
aattactgct ccaaagacaa aatccccatc aggaagtatg ccgacggcac catcgacatt   2040
gaggaggtca cagagaaccc caagactgag gtgtgtggtg gggagaaagg gccttgctgc   2100
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca   2280
gacacctaca acatcaccga cccggaagag ctggagacag agtacccttt ctttgagagc   2340
agagtggata caaggagag aactgtcatt tctaaccttc ggcctttcac attgtaccgc   2400
atcgatatcc acagctgcaa ccacgaggct gagaagctgg gctgcagcgc ctccaacttc   2460
gtctttgcaa ggactatgcc cgcagaagga gcagatgaca ttcctgggcc agtgacctgg   2520
gagccaaggc ctgaaaactc catcttttta aagtggccgg aacctgagaa tcccaatgga   2580
ttgattctaa tgtatgaaat aaaatacgga tcacaagttg aggatcagcg agaatgtgtg   2640
tccagacagg aatacaggaa gtatggaggg gccaagctaa accggctaaa cccggggaac   2700
```

-continued

```
tacacagccc ggattcaggc cacatctctc tctgggaatg ggtcgtggac agatcctgtg    2760
ttcttctatg tccaggccaa aacaggatat gaaaacttct ga                      2802
```

<210> SEQ ID NO 6
<211> LENGTH: 933
<212> TYPE: PRT
<213> ORGANISM: Artificial sequence
<220> FEATURE:
<223> OTHER INFORMATION: IGF1R

<400> SEQUENCE: 6

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350
```

```
Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
                580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765
```

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn Phe
            930

<210> SEQ ID NO 7
<211> LENGTH: 3516
<212> TYPE: DNA
<213> ORGANISM: Artificial sequence
<220> FEATURE:
<223> OTHER INFORMATION: sIGF1R-hFc-IgG1

<400> SEQUENCE: 7

```
atgaagtctg gctccggagg agggtccccg acctcgctgt ggggggctcct gtttctctcc      60
gccgcgctct cgctctggcc gacgagtgga gaaatctgcg ggccaggcat cgacatccgc     120
aacgactatc agcagctgaa gcgcctggag aactgcacgg tgatcgaggg ctacctccac     180
atcctgctca tctccaaggc cgaggactac cgcagctacc gcttcccaa gctcacggtc     240
attaccgagt acttgctgct gttccgagtg gctggcctcg agagcctcgg agacctcttc     300
cccaacctca cggtcatccg cggctggaaa ctcttctaca actacgccct ggtcatcttc     360
gagatgacca atctcaagga tattgggctt acaacctga ggaacattac tcggggggcc     420
atcaggattg agaaaaatgc tgacctctgt tacctctcca ctgtggactg gtccctgatc     480
ctggatgcgg tgtccaataa ctacattgtg ggaataagc ccccaaagga atgtggggac     540
ctgtgtccag ggaccatgga ggagaagccg atgtgtgaga agaccaccat caacaatgag     600
tacaactacc gctgctggac cacaaaccgc tgccagaaaa tgtgcccaag cacgtgtggg     660
aagcgggcgt gcaccgagaa caatgagtgc tgccaccccg agtgcctggg cagctgcagc     720
gcgcctgaca cgacacggc ctgtgtagct tgccgccact actactatgc cggtgtctgt     780
gtgcctgcct gcccgcccaa cacctacagg tttgagggct ggcgctgtgt ggaccgtgac     840
ttctgcgcca acatcctcag cgccgagagc agcgactccg aggggtttgt gatccacgac     900
ggcgagtgca tgcaggagtg ccctctcggc ttcatccgca acggcagcca gagcatgtac     960
tgcatccctt gtgaaggtcc ttgcccgaag gtctgtgagg aagaaagaa aacaaagacc    1020
attgattctg ttacttctgc tcagatgctc caaggatgca ccatcttcaa gggcaatttg    1080
```

```
ctcattaaca tccgacgggg gaataacatt gcttcagagc tggagaactt catggggctc    1140
atcgaggtgg tgacgggcta cgtgaagatc cgccattctc atgccttggt ctccttgtcc    1200
ttcctaaaaa accttcgcct catcctagga gaggagcagc tagaagggaa ttactccttc    1260
tacgtcctcg acaaccagaa cttgcagcaa ctgtgggact gggaccaccg caacctgacc    1320
atcaaagcag ggaaaatgta ctttgctttc aatcccaaat tatgtgtttc cgaaatttac    1380
cgcatggagg aagtgacggg gactaaaggg cgccaaagca aggggacat  aaacaccagg    1440
aacaacgggg agagagcctc ctgtgaaagt gacgtcctgc atttcacctc caccaccacg    1500
tcgaagaatc gcatcatcat aacctggcac cggtaccggc cccctgacta cagggatctc    1560
atcagcttca ccgtttacta caaggaagca ccctttaaga atgtcacaga gtatgatggg    1620
caggatgcct gcggctccaa cagctggaac atggtggacg tggacctccc gcccaacaag    1680
gacgtggagc ccggcatctt actacatggg ctgaagccct ggactcagta cgccgtttac    1740
gtcaaggctg tgaccctcac catggtggag aacgaccata tccgtggggc caagagtgag    1800
atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggccttttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta  aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttcg aattcgatat ctcgagcacc    2820
atggttagat ctgacaaaac tcacacatgc ccaccgtgcc cagcacctga actcctgggg    2880
ggaccgtcag tcttcctctt ccccccaaaa cccaaggaca ccctcatgat ctcccggacc    2940
cctgaggtca catgcgtggt ggtggacgtg agccacgaag accctgaggt caagttcaac    3000
tggtacgtgg acggcgtgga ggtgcataat gccaagacaa agccgcggga ggagcagtac    3060
aacagcacgt accgtgtggt cagcgtcctc accgtcctgc accaggactg gctgaatggc    3120
aaggagtaca agtgcaaggt ctccaacaaa gccctcccag cccccatcga gaaaaccatc    3180
tccaaagcca agggcagccc cgagaaccca caggtgtaca ccctgccccc atcccgggag    3240
gagatgacca agaaccaggt cagcctgacc tgcctggtca aaggcttcta tcccagcgac    3300
atcgccgtgg agtgggagag caatgggcag ccggagaaca actacaagac cacgcctccc    3360
gtgctggact ccgacggctc cttcttcctc tacagcaagc tcaccgtgga caagagcagg    3420
tggcagcagg ggaacgtctt ctcatgctcc gtgatgcacg aggctctgca caaccactac    3480
```

```
acgcagaaga gcctctccct gtctccgggt aaatga                                  3516
```

<210> SEQ ID NO 8
<211> LENGTH: 1171
<212> TYPE: PRT
<213> ORGANISM: Artificial sequence
<220> FEATURE:
<223> OTHER INFORMATION: sIGF1R-hFc-IgG1

<400> SEQUENCE: 8

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350
```

-continued

Cys Thr Ile Phe Lys Gly Asn Leu Leu Ile Asn Ile Arg Gly Asn
            355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
            405                 410                 415

Asn Tyr Ser Phe Tyr Val Leu Asp Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn

```
            770             775             780
Lys Glu Arg Thr Val Ile Ser Asn Leu Arg Pro Phe Thr Leu Tyr Arg
785                 790             795                 800

Ile Asp Ile His Ser Cys Asn His Glu Ala Glu Lys Leu Gly Cys Ser
                805             810              815

Ala Ser Asn Phe Val Phe Ala Arg Thr Met Pro Ala Glu Gly Ala Asp
                820             825             830

Asp Ile Pro Gly Pro Val Thr Trp Glu Pro Arg Pro Glu Asn Ser Ile
            835             840             845

Phe Leu Lys Trp Pro Glu Pro Glu Asn Pro Asn Gly Leu Ile Leu Met
        850             855             860

Tyr Glu Ile Lys Tyr Gly Ser Gln Val Glu Asp Gln Arg Glu Cys Val
865             870             875             880

Ser Arg Gln Glu Tyr Arg Lys Tyr Gly Gly Ala Lys Leu Asn Arg Leu
                885             890             895

Asn Pro Gly Asn Tyr Thr Ala Arg Ile Gln Ala Thr Ser Leu Ser Gly
                900             905             910

Asn Gly Ser Trp Thr Asp Pro Val Phe Phe Tyr Val Gln Ala Lys Thr
            915             920             925

Gly Tyr Glu Asn Phe Glu Phe Asp Ile Ser Ser Thr Met Val Arg Ser
            930             935             940

Asp Lys Thr His Thr Cys Pro Pro Cys Pro Ala Pro Glu Leu Leu Gly
945             950             955             960

Gly Pro Ser Val Phe Leu Phe Pro Pro Lys Pro Lys Asp Thr Leu Met
                965             970             975

Ile Ser Arg Thr Pro Glu Val Thr Cys Val Val Val Asp Val Ser His
            980             985             990

Glu Asp Pro Glu Val Lys Phe Asn Trp Tyr Val Asp Gly Val Glu Val
                995             1000            1005

His Asn Ala Lys Thr Lys Pro Arg Glu Glu Gln Tyr Asn Ser Thr
    1010            1015            1020

Tyr Arg Val Val Ser Val Leu Thr Val Leu His Gln Asp Trp Leu
    1025            1030            1035

Asn Gly Lys Glu Tyr Lys Cys Lys Val Ser Asn Lys Ala Leu Pro
    1040            1045            1050

Ala Pro Ile Glu Lys Thr Ile Ser Lys Ala Lys Gly Gln Pro Arg
    1055            1060            1065

Glu Pro Gln Val Tyr Thr Leu Pro Pro Ser Arg Glu Glu Met Thr
    1070            1075            1080

Lys Asn Gln Val Ser Leu Thr Cys Leu Val Lys Gly Phe Tyr Pro
    1085            1090            1095

Ser Asp Ile Ala Val Glu Trp Glu Ser Asn Gly Gln Pro Glu Asn
    1100            1105            1110

Asn Tyr Lys Thr Thr Pro Pro Val Leu Asp Ser Asp Gly Ser Phe
    1115            1120            1125

Phe Leu Tyr Ser Lys Leu Thr Val Asp Lys Ser Arg Trp Gln Gln
    1130            1135            1140

Gly Asn Val Phe Ser Cys Ser Val Met His Glu Ala Leu His Asn
    1145            1150            1155

His Tyr Thr Gln Lys Ser Leu Ser Leu Ser Pro Gly Lys
    1160            1165            1170

<210> SEQ ID NO 9
```

<211> LENGTH: 3486
<212> TYPE: DNA
<213> ORGANISM: Artificial sequence
<220> FEATURE:
<223> OTHER INFORMATION: sIGF1R-hFc-IgG2

<400> SEQUENCE: 9

| | | | | | |
|---|---|---|---|---|---:|
| atgaagtctg | gctccggagg | agggtccccg | acctcgctgt | gggggctcct | gtttctctcc | 60 |
| gccgcgctct | cgctctggcc | gacgagtgga | gaaatctgcg | gccaggcat | cgacatccgc | 120 |
| aacgactatc | agcagctgaa | gcgcctggag | aactgcacgg | tgatcgaggg | ctacctccac | 180 |
| atcctgctca | tctccaaggc | cgaggactac | cgcagctacc | gcttccccaa | gctcacggtc | 240 |
| attaccgagt | acttgctgct | gttccgagtg | gctggcctcg | agagcctcgg | agacctcttc | 300 |
| cccaacctca | cggtcatccg | cggctggaaa | ctcttctaca | actacgccct | ggtcatcttc | 360 |
| gagatgacca | atctcaagga | tattgggctt | acaacctga | ggaacattac | tcggggggcc | 420 |
| atcaggattg | agaaaaatgc | tgacctctgt | tacctctcca | ctgtggactg | gtccctgatc | 480 |
| ctggatgcgg | tgtccaataa | ctacattgtg | gggaataagc | ccccaaagga | atgtggggac | 540 |
| ctgtgtccag | ggaccatgga | ggagaagccg | atgtgtgaga | agaccaccat | caacaatgag | 600 |
| tacaactacc | gctgctggac | cacaaaccgc | tgccagaaaa | tgtgcccaag | cacgtgtggg | 660 |
| aagcgggcgt | gcaccgagaa | caatgagtgc | tgccacccccg | agtgcctggg | cagctgcagc | 720 |
| gcgcctgaca | acgacacggc | ctgtgtagct | tgccgccact | actactatgc | cggtgtctgt | 780 |
| gtgcctgcct | gcccgcccaa | cacctacagg | tttgagggct | ggcgctgtgt | ggaccgtgac | 840 |
| ttctgcgcca | catcctcag | cgccgagagc | agcgactccg | aggggtttgt | gatccacgac | 900 |
| ggcgagtgca | tgcaggagtg | ccccctcggc | ttcatccgca | acggcagcca | gagcatgtac | 960 |
| tgcatccctt | gtgaaggtcc | ttgcccgaag | gtctgtgagg | aagaaaagaa | aacaaagacc | 1020 |
| attgattctg | ttacttctgc | tcagatgctc | caaggatgca | ccatcttcaa | gggcaatttg | 1080 |
| ctcattaaca | tccgacgggg | gaataacatt | gcttcagagc | tggagaactt | catgggctc | 1140 |
| atcgaggtgg | tgacgggcta | cgtgaagatc | cgccattctc | atgccttggt | ctccttgtcc | 1200 |
| ttcctaaaaa | accttcgcct | catcctagga | gaggagcagc | tagaagggaa | ttactccttc | 1260 |
| tacgtcctcg | acaaccagaa | cttgcagcaa | ctgtgggact | gggaccaccg | caacctgacc | 1320 |
| atcaaagcag | ggaaaatgta | ctttgctttc | aatcccaaat | tatgtgtttc | gaaatttac | 1380 |
| cgcatggagg | aagtgacggg | gactaaaggg | cgccaaagca | aagggacat | aaacaccagg | 1440 |
| aacaacgggg | agagagcctc | ctgtgaaagt | gacgtcctgc | atttcacctc | caccaccacg | 1500 |
| tcgaagaatc | gcatcatcat | aacctggcac | cggtaccggc | ccctgactg | agggatctc | 1560 |
| atcagcttca | ccgtttacta | caaggaagca | ccctttaaga | atgtcacaga | gtatgatggg | 1620 |
| caggatgcct | gcggctccaa | cagctggaac | atggtggacg | tggacctccc | gcccaacaag | 1680 |
| gacgtggagc | ccggcatctt | actacatggg | ctgaagcct | ggactcagta | cgccgtttac | 1740 |
| gtcaaggctg | tgacctcac | catggtggag | aacgaccata | tccgtgggc | caagagtgag | 1800 |
| atcttgtaca | ttcgcaccaa | tgcttcagtt | cctccattc | ccttggacgt | tctttcagca | 1860 |
| tcgaactcct | cttctcagtt | aatcgtgaag | tggaacccctc | cctctctgcc | aacggcaac | 1920 |
| ctgagttact | acattgtgcg | ctggcagcgg | cagcctcagg | acggctacct | ttaccggcac | 1980 |
| aattactgct | ccaaagacaa | aatcccatc | aggaagtatg | ccgacggcac | catcgacatt | 2040 |
| gaggaggtca | cagagaaccc | caagactgag | gtgtgtggtg | gggagaaagg | gccttgctgc | 2100 |
| gcctgcccca | aaactgaagc | cgagaagcag | gccgagaagg | aggaggctga | ataccgcaaa | 2160 |

```
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtaccettt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg ccaagctaa accggctaaa cccggggaac    2700
tacacagccc ggattcaggc cacatctctc tctgggaatg ggtcgtggac agatcctgtg    2760
ttcttctatg tccaggccaa acaggatat gaaaacttcg agcgcaaatg ttgtgtcgag    2820
tgcccaccgt gccagcacc acctgtggca ggaccgtcag tcttcctctt ccccccaaaa    2880
cccaaggaca ccctcatgat ctcccggacc cctgaggtca cgtgcgtggt ggtggacgtg    2940
agccacgaag accccgaggt ccagttcaac tggtacgtgg acggcgtgga ggtgcataat    3000
gccaagacaa agccacggga ggagcagttc aacagcacgt tccgtgtggt cagcgtcctc    3060
accgttgtgc accaggactg gctgaacggc aaggagtaca agtgcaaggt ctccaacaaa    3120
ggcctcccag ccccatcga aaaaccatc tccaaaacca aagggcagcc ccgagaacca    3180
caggtgtaca ccctgccccc atccccggag gagatgacca agaaccaggt cagcctgacc    3240
tgcctggtca aaggcttcta ccccagcgac atcgccgtgg agtgggagag caatgggcag    3300
ccggagaaca actacaagac cacctcccc atgctggact ccgacggctc cttcttcctc    3360
tacagcaagc tcaccgtgga caagagcagg tggcagcagg ggaacgtctt ctcatgctcc    3420
gtgatgcatg aggctctgca caaccactac acgcagaaga gcctctccct gtctccgggt    3480
aaatga                                                               3486
```

<210> SEQ ID NO 10
<211> LENGTH: 1161
<212> TYPE: PRT
<213> ORGANISM: Artificial sequence
<220> FEATURE:
<223> OTHER INFORMATION: sIGF1R-hFc-IgG2

<400> SEQUENCE: 10

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
```

```
            115                 120                 125
Gly Leu Tyr Asn Leu Arg Asn Ile Thr Arg Gly Ala Ile Arg Ile Glu
130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                    165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
530                 535                 540
```

```
Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
        580                 585                 590

His Ile Arg Gly Ala Lys Ser Glu Ile Leu Tyr Ile Arg Thr Asn Ala
    595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Glu Arg Lys Cys Cys Val Glu Cys Pro Cys
    930                 935                 940

Pro Ala Pro Pro Val Ala Gly Pro Ser Val Phe Leu Phe Pro Pro Lys
945                 950                 955                 960
```

Pro Lys Asp Thr Leu Met Ile Ser Arg Thr Pro Glu Val Thr Cys Val
                965                 970                 975

Val Val Asp Val Ser His Glu Asp Pro Glu Val Gln Phe Asn Trp Tyr
        980                 985                 990

Val Asp Gly Val Glu Val His Asn Ala Lys Thr Lys Pro Arg Glu Glu
        995                 1000                1005

Gln Phe Asn Ser Thr Phe Arg Val Val Ser Val Leu Thr Val Val
    1010                1015                1020

His Gln Asp Trp Leu Asn Gly Lys Glu Tyr Lys Cys Lys Val Ser
    1025                1030                1035

Asn Lys Gly Leu Pro Ala Pro Ile Glu Lys Thr Ile Ser Lys Thr
    1040                1045                1050

Lys Gly Gln Pro Arg Glu Pro Gln Val Tyr Thr Leu Pro Pro Ser
    1055                1060                1065

Arg Glu Glu Met Thr Lys Asn Gln Val Ser Leu Thr Cys Leu Val
    1070                1075                1080

Lys Gly Phe Tyr Pro Ser Asp Ile Ala Val Glu Trp Glu Ser Asn
    1085                1090                1095

Gly Gln Pro Glu Asn Asn Tyr Lys Thr Thr Pro Pro Met Leu Asp
    1100                1105                1110

Ser Asp Gly Ser Phe Phe Leu Tyr Ser Lys Leu Thr Val Asp Lys
    1115                1120                1125

Ser Arg Trp Gln Gln Gly Asn Val Phe Ser Cys Ser Val Met His
    1130                1135                1140

Glu Ala Leu His Asn His Tyr Thr Gln Lys Ser Leu Ser Leu Ser
    1145                1150                1155

Pro Gly Lys
    1160

<210> SEQ ID NO 11
<211> LENGTH: 3516
<212> TYPE: DNA
<213> ORGANISM: Artificial Sequence
<220> FEATURE:
<223> OTHER INFORMATION: Encodes modified human Trap H protein

<400> SEQUENCE: 11
atgaagtctg gctccggagg agggtccccg acctcgctgt gggggctcct gtttctctcc      60
gccgcgctct cgctctggcc gacgagtgga gaaatctgcg ggccaggcat cgacatccgc     120
aacgactatc agcagctgaa gcgcctggag aactgcacgg tgatcgaggg ctacctccac     180
atcctgctca tctccaaggc cgaggactac cgcagctacc gcttccccaa gctcacggtc     240
attaccgagt acttgctgct gttccgagtg gctggcctcg agagcctcgg agacctcttc     300
cccaacctca cggtcatccg cggctggaaa ctcttctaca actacgccct ggtcatcttc     360
gagatgacca atctcaagga tattgggctt acaacctga ggaacattac tcgggggggcc     420 atcaggattg agaaaaatgc tgacctctgt tacctctcca ctgtggactg gtccctgatc     480
ctggatgcgg tgtccaataa ctacattgtg gggaataagc ccccaaagga atgtggggac     540
ctgtgtccag ggaccatgga ggagaagccg atgtgtgaga agaccaccat caacaatgag     600
tacaactacc gctgctggac cacaaaccgc tgccagaaaa tgtgcccaag cacgtgtggg     660
aagcgggcgt gcaccgagaa caatgagtgc tgccacccccg agtgcctggg cagctgcagc     720
gcgcctgaca cgacacggc ctgtgtagct tgccgccact actactatgc cggtgtctgt     780
gtgcctgcct gcccgcccaa cacctacagg tttgagggct ggcgctgtgt ggaccgtgac     840

```
ttctgcgcca acatcctcag cgccgagagc agcgactccg aggggtttgt gatccacgac      900
ggcgagtgca tgcaggagtg cccctcgggc ttcatccgca acggcagcca gagcatgtac      960
tgcatccctt gtgaaggtcc ttgcccgaag gtctgtgagg aagaaaagaa aacaaagacc     1020
attgattctg ttacttctgc tcagatgctc caaggatgca ccatcttcaa gggcaatttg     1080
ctcattaaca tccgacgggg gaataacatt gcttcagagc tggagaactt catggggctc     1140
atcgaggtgg tgacgggcta cgtgaagatc cgccattctc atgccttggt ctccttgtcc     1200
ttcctaaaaa accttcgcct catcctagga gaggagcagc tagaagggaa ttactccttc     1260
tacgtcctcg acaaccagaa cttgcagcaa ctgtgggact gggaccaccg caacctgacc     1320
atcaaagcag ggaaaatgta ctttgctttc aatcccaaat tatgtgtttc cgaaatttac     1380
cgcatggagg aagtgacggg gactaaaggg cgccaaagca aagggacat  aaacaccagg     1440
aacaacgggg agagagcctc ctgtgaaagt gacgtcctgc atttcacctc caccaccacg     1500
tcgaagaatc gcatcatcat aacctggcac cggtaccggc cccctgacta cagggatctc     1560
atcagcttca ccgtttacta caaggaagca cccttttaaga atgtcacaga gtatgatggg     1620
caggatgcct gcggctccaa cagctggaac atggtggacg tggacctccc gcccaacaag     1680
gacgtggagc ccggcatctt actacatggg ctgaagccct ggactcagta cgccgtttac     1740
gtcaaggctg tgaccctcac catggtggag aacgaccata tccgtgggc  caagagtgag     1800
atcttgtaca ttcgcaccaa tgcttcagtt ccttccattc ccttggacgt tctttcagca     1860
tcgaactcct cttctcagtt aatcgtgaag tggaaccctc cctctctgcc caacggcaac     1920
ctgagttact acattgtgcg ctggcagcgg cagcctcagg acggctacct ttaccggcac     1980
aattactgct ccaaagacaa aatccccatc aggaagtatg ccgacggcac catcgacatt     2040
gaggaggtca cagagaaccc caagactgag gtgtgtggtg gggagaaagg gccttgctgc     2100
gcctgcccca aaactgaagc cgagaagcag gccgagaagg aggaggctga ataccgcaaa     2160
gtctttgaga atttcctgca caactccatc ttcgtgccca gacctgaaag gaagcggaga     2220
gatgtcatgc aagtggccaa caccaccatg tccagccgaa gcaggaacac cacgccgca     2280
gacacctaca acatcaccga cccggaagag ctggagacag agtacccttt ctttgagagc     2340
agagtggata caaggagag aactgtcatt tctaaccttc ggcctttcac attgtaccgc     2400
atcgatatcc acagctgcaa ccacgaggct gagaagctgg gctgcagcgc ctccaacttc     2460
gtctttgcaa ggactatgcc cgcagaagga gcagatgaca ttcctgggcc agtgacctgg     2520
gagccaaggc ctgaaaactc catcttttta agtggccgg  aacctgagaa tcccaatgga     2580
ttgattctaa tgtatgaaat aaaatacgga tcacaagttg aggatcagcg agaatgtgtg     2640
tccagacagg aatacaggaa gtatggaggg gccaagctaa accggctaaa cccgggaac      2700
tacacagccc ggattcaggc cacatctctc tctgggaatg ggtcgtggac agatcctgtg     2760
ttcttctatg tccaggccaa aacaggatat gaaaacttcg aattcgatat ctcgagcacc     2820
atggttagat ctgacaaaac tcacacaagc ccaccgagtc cagcacctga actcctgggg     2880
ggaccgtcag tcttcctctt ccccccaaaa cccaaggaca ccctcatgat ctcccggacc     2940
cctgaggtca catgcgtggt ggtggacgtg agccacgaag accctgaggt caagttcaac     3000
tggtacgtgg acggcgtgga ggtgcataat gccaagacaa agccgcggga ggagcagtac     3060
aacagcacgt accgtgtggt cagcgtcctc accgtcctgc accaggactg gctgaatggc     3120
aaggagtaca agtgcaaggt ctccaacaaa gccctcccag cccccatcga gaaaaccatc     3180
```

-continued

```
tccaaagcca aagggcagcc ccgagaacca caggtgtaca ccctgccccc atcccgggag    3240
gagatgacca agaaccaggt cagcctgacc tgcctggtca aaggcttcta tcccagcgac    3300
atcgccgtgg agtgggagag caatgggcag ccggagaaca actacaagac cacgcctccc    3360
gtgctggact ccgacggctc cttcttcctc tacagcaagc tcaccgtgga caagagcagg    3420
tggcagcagg ggaacgtctt ctcatgctcc gtgatgcacg aggctctgca caaccactac    3480
acgcagaaga gcctctccct gtctccgggt aaatga                              3516
```

<210> SEQ ID NO 12
<211> LENGTH: 1171
<212> TYPE: PRT
<213> ORGANISM: Artificial Sequence
<220> FEATURE:
<223> OTHER INFORMATION: Modified human Trap H protein

<400> SEQUENCE: 12

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300
```

```
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
```

```
                725                 730                 735
Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
            850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
            915                 920                 925

Gly Tyr Glu Asn Phe Glu Phe Asp Ile Ser Ser Thr Met Val Arg Ser
            930                 935                 940

Asp Lys Thr His Thr Ser Pro Pro Ser Pro Ala Pro Glu Leu Leu Gly
945                 950                 955                 960

Gly Pro Ser Val Phe Leu Phe Pro Pro Lys Pro Lys Asp Thr Leu Met
                965                 970                 975

Ile Ser Arg Thr Pro Glu Val Thr Cys Val Val Val Asp Val Ser His
                980                 985                 990

Glu Asp Pro Glu Val Lys Phe Asn Trp Tyr Val Asp Gly Val Glu Val
            995                 1000                1005

His Asn Ala Lys Thr Lys Pro Arg Glu Glu Gln Tyr Asn Ser Thr
        1010                1015                1020

Tyr Arg Val Val Ser Val Leu Thr Val Leu His Gln Asp Trp Leu
        1025                1030                1035

Asn Gly Lys Glu Tyr Lys Cys Lys Val Ser Asn Lys Ala Leu Pro
        1040                1045                1050

Ala Pro Ile Glu Lys Thr Ile Ser Lys Ala Lys Gly Gln Pro Arg
        1055                1060                1065

Glu Pro Gln Val Tyr Thr Leu Pro Pro Ser Arg Glu Glu Met Thr
        1070                1075                1080

Lys Asn Gln Val Ser Leu Thr Cys Leu Val Lys Gly Phe Tyr Pro
        1085                1090                1095

Ser Asp Ile Ala Val Glu Trp Glu Ser Asn Gly Gln Pro Glu Asn
        1100                1105                1110

Asn Tyr Lys Thr Thr Pro Pro Val Leu Asp Ser Asp Gly Ser Phe
        1115                1120                1125

Phe Leu Tyr Ser Lys Leu Thr Val Asp Lys Ser Arg Trp Gln Gln
        1130                1135                1140
```

Gly Asn Val Phe Ser Cys Ser Val Met His Glu Ala Leu His Asn
        1145                1150                1155

His Tyr Thr Gln Lys Ser Leu Ser Leu Ser Pro Gly Lys
    1160                1165             1170

<210> SEQ ID NO 13
<211> LENGTH: 3549
<212> TYPE: DNA
<213> ORGANISM: Artificial Sequence
<220> FEATURE:
<223> OTHER INFORMATION: Encodes modified human Trap H protein

<400> SEQUENCE: 13

| | | | | | |
|---|---|---|---|---|---|
| atgaagtctg | gctccggagg | agggtccccg | acctcgctgt | gggggctcct | gtttctctcc | 60 |
| gccgcgctct | cgctctggcc | gacgagtgga | gaaatctgcg | ggccaggcat | cgacatccgc | 120 |
| aacgactatc | agcagctgaa | gcgcctggag | aactgcacgg | tgatcgaggg | ctacctccac | 180 |
| atcctgctca | tctccaaggc | cgaggactac | cgcagctacc | gcttccccaa | gctcacggtc | 240 |
| attccgagt | acttgctgct | gttccgagtg | gctggcctcg | agagcctcgg | agacctcttc | 300 |
| cccaacctca | cggtcatccg | cggctggaaa | ctcttctaca | actacgccct | ggtcatcttc | 360 |
| gagatgacca | atctcaagga | tattgggctt | acaacctga | ggaacattac | tcgggggcc | 420 |
| atcaggattg | agaaaaatgc | tgacctctgt | tacctctcca | ctgtggactg | gtccctgatc | 480 |
| ctggatgcgg | tgtccaataa | ctacattgtg | gggaataagc | ccccaaagga | atgtgggac | 540 |
| ctgtgtccag | ggaccatgga | ggagaagccg | atgtgtgaga | agaccaccat | caacaatgag | 600 |
| tacaactacc | gctgctggac | cacaaaccgc | tgccagaaaa | tgtgcccaag | cacgtgtggg | 660 |
| aagcgggcgt | gcaccgagaa | caatgagtgc | tgccacccg | agtgcctggg | cagctgcagc | 720 |
| gcgcctgaca | acgacacggc | ctgtgtagct | tgccgccact | actactatgc | cggtgtctgt | 780 |
| gtgcctgcct | gcccgcccaa | cacctacagg | tttgagggct | ggcgctgtgt | ggaccgtgac | 840 |
| ttctgcgcca | acatcctcag | cgccgagagc | agcgactccg | aggggtttgt | gatccacgac | 900 |
| ggcgagtgca | tgcaggagtg | cccctcgggc | ttcatccgca | acggcagcca | gagcatgtac | 960 |
| tgcatcccctt | gtgaaggtcc | ttgcccgaag | gtctgtgagg | aagaaaagaa | aacaaagacc | 1020 |
| attgattctg | ttacttctgc | tcagatgctc | caaggatgca | ccatcttcaa | gggcaatttg | 1080 |
| ctcattaaca | tccgacgggg | gaataacatt | gcttcagagc | tggagaactt | catggggctc | 1140 |
| atcgaggtgg | tgacgggcta | cgtgaagatc | cgccattctc | atgccttggt | ctccttgtcc | 1200 |
| ttcctaaaaa | accttcgcct | catcctagga | gaggagcagc | tagaagggaa | ttactccttc | 1260 |
| tacgtcctcg | acaaccagaa | cttgcagcaa | ctgtgggact | gggaccaccg | caacctgacc | 1320 |
| atcaaagcag | ggaaaatgta | ctttgctttc | aatcccaaat | tatgtgtttc | gaaatttac | 1380 |
| cgcatggagg | aagtgacggg | gactaaaggg | cgccaaagca | agggggacat | aaacaccagg | 1440 |
| aacaacgggg | agagagcctc | ctgtgaaagt | gacgtcctgc | atttcacctc | caccaccacg | 1500 |
| tcgaagaatc | gcatcatcat | aacctggcac | cggtaccggc | ccctgactca | cagggatctc | 1560 |
| atcagcttca | ccgtttacta | caaggaagca | ccctttaaga | atgtcacaga | gtatgatggg | 1620 |
| caggatgcct | gcggctccaa | cagctggaac | atggtggacg | tggacctccc | gcccaacaag | 1680 |
| gacgtggagc | ccggcatctt | actacatggg | ctgaagcct | ggactcagta | cgccgtttac | 1740 |
| gtcaaggctg | tgaccctcac | catggtggag | aacgaccata | tccgtgggc | caagagtgag | 1800 |
| atcttgtaca | ttcgcaccaa | tgcttcagtt | ccttccattc | ccttggacgt | tctttcagca | 1860 |

```
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa atccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggccttttcac attgtaccgc    2400 atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catcttttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttcg gcggcggcgg tagtggcggc    2820
ggtggcagcg gcggtggcgg cagtggtggc ggcggcagcg gtggcgacaa aactcacaca    2880
tgcccaccgt gcccagcacc tgaactcctg gggggaccgt cagtcttcct cttcccccca    2940
aaacccaagg acaccctcat gatctcccgg acccctgagg tcacatgcgt ggtggtggac    3000
gtgagccacg aagaccctga ggtcaagttc aactggtacg tggacggcgt ggaggtgcat    3060
aatgccaaga caaagccgcg ggaggagcag tacaacagca cgtaccgtgt ggtcagcgtc    3120
ctcaccgtcc tgcaccagga ctggctgaat ggcaaggagt acaagtgcaa ggtctccaac    3180
aaagccctcc cagcccccat cgagaaaacc atctccaaag ccaaagggca gccccgagaa    3240
ccacaggtgt acaccctgcc cccatcccgg gaggagatga ccaagaacca ggtcagcctg    3300
acctgcctgg tcaaaggctt ctatcccagc gacatcgccg tggagtggga gagcaatggg    3360
cagccggaga caaactacaa gaccacgcct cccgtgctgg actccgacgg ctccttcttc    3420
ctctacagca agctcaccgt ggacaagagc aggtggcagc aggggaacgt cttctcatgc    3480
tccgtgatgc acgaggctct gcacaaccac tacacgcaga agagcctctc cctgtctccg    3540
ggtaaatga                                                            3549
```

<210> SEQ ID NO 14
<211> LENGTH: 1182
<212> TYPE: PRT
<213> ORGANISM: Artificial Sequence
<220> FEATURE:
<223> OTHER INFORMATION: Modified human Trap H protein

<400> SEQUENCE: 14

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60
```

```
Ser Lys Ala Glu Asp Tyr Arg Ser Tyr Arg Phe Pro Lys Leu Thr Val
 65                  70                  75                  80

Ile Thr Glu Tyr Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
                290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
                355                 360                 365

Asn Ile Ala Ser Glu Leu Glu Asn Phe Met Gly Leu Ile Glu Val Val
                370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
                435                 440                 445

Ala Phe Asn Pro Lys Leu Cys Val Ser Glu Ile Tyr Arg Met Glu Glu
                450                 455                 460

Val Thr Gly Thr Lys Gly Arg Gln Ser Lys Gly Asp Ile Asn Thr Arg
465                 470                 475                 480
```

```
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
            515                 520                 525
Glu Ala Pro Phe Lys Asn Val Thr Glu Tyr Asp Gly Gln Asp Ala Cys
            530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
                660                 665                 670
Tyr Ala Asp Gly Thr Ile Asp Ile Glu Glu Val Thr Glu Asn Pro Lys
            675                 680                 685
Thr Glu Val Cys Gly Gly Glu Lys Gly Pro Cys Cys Ala Cys Pro Lys
            690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
            755                 760                 765
Glu Glu Leu Glu Thr Glu Tyr Pro Phe Phe Glu Ser Arg Val Asp Asn
            770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                885                 890                 895
Asn Pro Gly Asn Tyr Thr Ala Arg Ile Gln Ala Thr Ser Leu Ser Gly
```

Asn Gly Ser Trp Thr Asp Pro Val Phe Phe Tyr Val Gln Ala Lys Thr
            915                 920                 925
Gly Tyr Glu Asn Phe Gly Gly Gly Ser Gly Gly Gly Ser Gly
        930                 935                 940
Gly Gly Gly Ser Gly Gly Gly Ser Gly Gly Asp Lys Thr His Thr
945                 950                 955                 960
Cys Pro Pro Cys Pro Ala Pro Glu Leu Leu Gly Gly Pro Ser Val Phe
                965                 970                 975
Leu Phe Pro Pro Lys Pro Lys Asp Thr Leu Met Ile Ser Arg Thr Pro
            980                 985                 990
Glu Val Thr Cys Val Val Val Asp Val Ser His Glu Asp Pro Glu Val
        995                 1000                1005
Lys Phe Asn Trp Tyr Val Asp Gly Val Glu Val His Asn Ala Lys
    1010                1015                1020
Thr Lys Pro Arg Glu Glu Gln Tyr Asn Ser Thr Tyr Arg Val Val
    1025                1030                1035
Ser Val Leu Thr Val Leu His Gln Asp Trp Leu Asn Gly Lys Glu
    1040                1045                1050
Tyr Lys Cys Lys Val Ser Asn Lys Ala Leu Pro Ala Pro Ile Glu
    1055                1060                1065
Lys Thr Ile Ser Lys Ala Lys Gly Gln Pro Arg Glu Pro Gln Val
    1070                1075                1080
Tyr Thr Leu Pro Pro Ser Arg Glu Glu Met Thr Lys Asn Gln Val
    1085                1090                1095
Ser Leu Thr Cys Leu Val Lys Gly Phe Tyr Pro Ser Asp Ile Ala
    1100                1105                1110
Val Glu Trp Glu Ser Asn Gly Gln Pro Glu Asn Asn Tyr Lys Thr
    1115                1120                1125
Thr Pro Pro Val Leu Asp Ser Asp Gly Ser Phe Phe Leu Tyr Ser
    1130                1135                1140
Lys Leu Thr Val Asp Lys Ser Arg Trp Gln Gln Gly Asn Val Phe
    1145                1150                1155
Ser Cys Ser Val Met His Glu Ala Leu His Asn His Tyr Thr Gln
    1160                1165                1170
Lys Ser Leu Ser Leu Ser Pro Gly Lys
    1175                1180

<210> SEQ ID NO 15
<211> LENGTH: 3549
<212> TYPE: DNA
<213> ORGANISM: Artificial Sequence
<220> FEATURE:
<223> OTHER INFORMATION: Encodes modified human Trap H protein

<400> SEQUENCE: 15
atgaagtctg gctccggagg agggtccccg acctcgctgt gggggctcct gtttctctcc      60
gccgcgctct cgctctggcc gacgagtgga gaaatctgcg gccaggcat cgacatccgc      120 aacgactatc agcagctgaa gcgcctggag aactgcacgg tgatcgaggg ctacctccac     180
atcctgctca tctccaaggc cgaggactac cgcagctacc gcttcccaa gctcacggtc     240 attaccgagt acttgctgct gttccgagtg ctggcctcg agagcctcgg agacctcttc     300
cccaacctca cggtcatccg cggctggaaa ctcttctaca actacgccct ggtcatcttc     360
gagatgacca atctcaagga tattgggctt tacaacctga ggaacattac tcgggggggcc     420

```
atcaggattg agaaaaatgc tgacctctgt tacctctcca ctgtggactg gtccctgatc    480
ctggatgcgg tgtccaataa ctacattgtg gggaataagc ccccaaagga atgtggggac    540
ctgtgtccag ggaccatgga ggagaagccg atgtgtgaga agaccaccat caacaatgag    600
tacaactacc gctgctggac cacaaaccgc tgccagaaaa tgtgcccaag cacgtgtggg    660
aagcgggcgt gcaccgagaa caatgagtgc tgccaccccg agtgcctggg cagctgcagc    720
gcgcctgaca cgacacggc ctgtgtagct tgccgccact actactatgc cggtgtctgt    780
gtgcctgcct gcccgcccaa cacctacagg tttgagggct ggcgctgtgt ggaccgtgac    840
ttctgcgcca acatcctcag cgccgagagc agcgactccg aggggtttgt gatccacgac    900
ggcgagtgca tgcaggagtg cccctcgggc ttcatccgca acggcagcca gagcatgtac    960
tgcatccctt gtgaaggtcc ttgcccgaag gtctgtgagg aagaaaagaa aacaaagacc   1020
attgattctg ttacttctgc tcagatgctc caaggatgca ccatcttcaa gggcaatttg   1080
ctcattaaca tccgacgggg gaataacatt gcttcagagc tggagaactt catggggctc   1140
atcgaggtgg tgacgggcta cgtgaagatc cgccattctc atgccttggt ctccttgtcc   1200
ttcctaaaaa accttcgcct catcctagga gaggagcagc tagaagggaa ttactccttc   1260
tacgtcctcg acaaccagaa cttgcagcaa ctgtgggact gggaccaccg caacctgacc   1320
atcaaagcag ggaaaatgta ctttgctttc aatcccaaat tatgtgtttc cgaaatttac   1380
cgcatggagg aagtgacggg gactaaaggg cgccaaagca aggggacat aaacaccagg   1440 aacaacgggg agagagcctc ctgtgaaagt gacgtcctgc atttcacctc caccaccacg   1500
tcgaagaatc gcatcatcat aacctggcac cggtaccggc ccctgacta cagggatctc   1560 atcagcttca ccgtttacta caaggaagca ccctttaaga atgtcacaga gtatgatggg   1620
caggatgcct gcggctccaa cagctggaac atggtggacg tggacctccc gcccaacaag   1680
gacgtggagc ccggcatctt actacatggg ctgaagccct ggactcagta cgccgtttac   1740
gtcaaggctg tgaccctcac catggtggag aacgaccata tccgtggggc caagagtgag   1800
atcttgtaca ttcgcaccaa tgcttcagtt ccttccattc ccttggacgt tctttcagca   1860
tcgaactcct cttctcagtt aatcgtgaag tggaaccctc cctctctgcc aacggcaac   1920 ctgagttact acattgtgcg ctggcagcgg cagcctcagg acggctacct ttaccggcac   1980
aattactgct ccaaagacaa aatccccatc aggaagtatg ccgacggcac catcgacatt   2040
gaggaggtca cagagaaccc caagactgag gtgtgtggtg gggagaaagg gccttgctgc   2100
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca   2280
gacacctaca catcaccga cccggaagag ctggagacag agtacccttt ctttgagagc   2340
agagtggata caaggagag aactgtcatt tctaaccttc ggcctttcac attgtaccgc   2400
atcgatatcc acagctgcaa ccacgaggct gagaagctgg gctgcagcgc ctccaacttc   2460
gtctttgcaa ggactatgcc cgcagaagga gcagatgaca ttcctgggcc agtgacctgg   2520
gagccaaggc ctgaaaactc catctttta aagtggccgg aacctgagaa tcccaatgga   2580
ttgattctaa tgtatgaaat aaaatacgga tcacaagttg aggatcagcg agaatgtgtg   2640
tccagacagg aatacaggaa gtatggaggg gccaagctaa accggctaaa cccggggaac   2700
tacacagccc ggattcaggc cacatctctc tctgggaatg ggtcgtggac agatcctgtg   2760
```

-continued

```
ttcttctatg tccaggccaa acaggatat gaaaacttcg gcggcggcgg tagtggcggc    2820
ggtggcagcg gcggtggcgg cagtggtggc ggcggcagcg gtggcgacaa aactcacaca    2880
agcccaccga gtccagcacc tgaactcctg gggggaccgt cagtcttcct cttcccccca    2940
aaacccaagg acaccctcat gatctcccgg acccctgagg tcacatgcgt ggtggtggac    3000
gtgagccacg aagaccctga ggtcaagttc aactggtacg tggacggcgt ggaggtgcat    3060
aatgccaaga caaagccgcg ggaggagcag tacaacagca cgtaccgtgt ggtcagcgtc    3120
ctcaccgtcc tgcaccagga ctggctgaat ggcaaggagt acaagtgcaa ggtctccaac    3180
aaagccctcc cagcccccat cgagaaaacc atctccaaag ccaagggcag ccccgagaa    3240
ccacaggtgt acaccctgcc cccatcccgg gaggagatga ccaagaacca ggtcagcctg    3300
acctgcctgg tcaaaggctt ctatcccagc gacatcgccg tggagtggga gagcaatggg    3360
cagccggaga acaactacaa gaccacgcct cccgtgctgg actccgacgg ctccttcttc    3420
ctctacagca agctcaccgt ggacaagagc aggtggcagc aggggaacgt cttctcatgc    3480
tccgtgatgc acgaggctct gcacaaccac tacacgcaga agagcctctc cctgtctccg    3540
ggtaaatga                                                            3549
```

<210> SEQ ID NO 16
<211> LENGTH: 1182
<212> TYPE: PRT
<213> ORGANISM: Artificial Sequence
<220> FEATURE:
<223> OTHER INFORMATION: Modified human Trap H protein
<400> SEQUENCE: 16

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220
```

```
Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
        260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640
```

```
Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
            675                 680                 685

Thr Glu Val Cys Gly Gly Lys Gly Pro Cys Cys Ala Cys Pro Lys
        690                 695                 700

Thr Glu Ala Glu Lys Gln Ala Lys Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
        770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
        850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
        915                 920                 925

Gly Tyr Glu Asn Phe Gly Gly Gly Ser Gly Gly Gly Ser Gly
                930                 935                 940

Gly Gly Gly Ser Gly Gly Gly Gly Ser Gly Gly Asp Lys Thr His Thr
945                 950                 955                 960

Ser Pro Pro Ser Pro Ala Pro Glu Leu Leu Gly Gly Pro Ser Val Phe
        965                 970                 975

Leu Phe Pro Pro Lys Pro Lys Asp Thr Leu Met Ile Ser Arg Thr Pro
        980                 985                 990

Glu Val Thr Cys Val Val Val Asp Val Ser His Glu Asp Pro Glu Val
            995                 1000                1005

Lys Phe Asn Trp Tyr Val Asp Gly Val Glu Val His Asn Ala Lys
        1010                1015                1020

Thr Lys Pro Arg Glu Glu Gln Tyr Asn Ser Thr Tyr Arg Val Val
        1025                1030                1035

Ser Val Leu Thr Val Leu His Gln Asp Trp Leu Asn Gly Lys Glu
        1040                1045                1050

Tyr Lys Cys Lys Val Ser Asn Lys Ala Leu Pro Ala Pro Ile Glu
```

```
                1055                1060                1065
Lys Thr Ile Ser Lys Ala Lys Gly Gln Pro Arg Glu Pro Gln Val
    1070                1075                1080

Tyr Thr Leu Pro Pro Ser Arg Glu Glu Met Thr Lys Asn Gln Val
    1085                1090                1095

Ser Leu Thr Cys Leu Val Lys Gly Phe Tyr Pro Ser Asp Ile Ala
    1100                1105                1110

Val Glu Trp Glu Ser Asn Gly Gln Pro Glu Asn Tyr Lys Thr
    1115                1120                1125

Thr Pro Pro Val Leu Asp Ser Asp Gly Ser Phe Phe Leu Tyr Ser
    1130                1135                1140

Lys Leu Thr Val Asp Lys Ser Arg Trp Gln Gln Gly Asn Val Phe
    1145                1150                1155

Ser Cys Ser Val Met His Glu Ala Leu His Asn His Tyr Thr Gln
    1160                1165                1170

Lys Ser Leu Ser Leu Ser Pro Gly Lys
    1175                1180

<210> SEQ ID NO 17
<211> LENGTH: 3540
<212> TYPE: DNA
<213> ORGANISM: Artificial Sequence
<220> FEATURE:
<223> OTHER INFORMATION: Encodes modified human Trap H protein

<400> SEQUENCE: 17
atgaagtctg ctccggagg agggtccccg acctcgctgt ggggctcct gtttctctcc      60 gccgcgctct cgctctggcc gacgagtgga gaaatctgcg gccaggcat cgacatccgc    120 aacgactatc agcagctgaa cgcctggag aactgcacgg tgatcgaggg ctacctccac    180
atcctgctca tctccaaggc cgaggactac cgcagctacc gcttccccaa gctcacggtc    240
attaccgagt acttgctgct gttccgagtg gctggcctcg agagcctcgg agacctcttc    300
cccaacctca cggtcatccg cggctggaaa ctcttctaca actacgccct ggtcatcttc    360
gagatgacca atctcaagga tattggctt tacaacctga ggaacattac tcggggggcc    420
atcaggattg agaaaaatgc tgacctctgt tacctctcca ctgtggactg tccctgatc    480 ctggatgcgg tgtccaataa ctacattgtg gggaataagc ccccaaagga atgtggggac    540
ctgtgtccag ggaccatgga ggagaagccg atgtgtgaga agaccaccat caacaatgag    600
tacaactacc gctgctggac cacaaaccgc tgccagaaaa tgtgcccaag cacgtgtggg    660
aagcgggcgt gcaccgagaa caatgagtgc tgccacccg agtgcctggg cagctgcagc    720
gcgcctgaca cgacacggc ctgtgtagct tgccgccact actactatgc cggtgtctgt    780
gtgcctgcct gcccgcccaa cacctacagg tttgagggct ggcgctgtgt ggaccgtgac    840
ttctgcgcca acatcctcag cgccgagagc gcgactccg aggggtttgt gatccacgac    900
ggcgagtgca tgcaggagtg cccctcgggc ttcatccgca acggcagcca gagcatgtac    960
tgcatcccct tgtgaaggtc cttgcccgaa gtctgtgagg aagaaaagaa aacaaagacc   1020
attgattctg ttacttctgc tcagatgctc caaggatgca ccatcttcaa gggcaatttg   1080
ctcattaaca tccgacgggg gaataacatt gcttcagagc tggagaactt catggggctc   1140
atcgaggtgg tgacgggcta cgtgaagatc cgccattctc atgccttggt ctccttgtcc   1200
ttcctaaaaa accttcgcct catcctagga gaggagcagc tagaagggaa ttactccttc   1260
tacgtcctcg acaaccagaa cttgcagcaa ctgtgggact gggaccaccg caacctgacc   1320
```

| | | | |
|---|---|---|---|
| atcaaagcag | ggaaaatgta | ctttgctttc aatcccaaat tatgtgtttc gaaatttac | 1380 |
| cgcatggagg | aagtgacggg | gactaaaggg cgccaaagca aagggacat aaacaccagg | 1440 |
| aacaacgggg | agagagcctc | ctgtgaaagt gacgtcctgc atttcacctc caccaccacg | 1500 |
| tcgaagaatc | gcatcatcat | aacctggcac cggtaccggc ccctgacta cagggatctc | 1560 |
| atcagcttca | ccgtttacta | caaggaagca ccctttaaga atgtcacaga gtatgatggg | 1620 |
| caggatgcct | gcggctccaa | cagctggaac atggtggacg tggacctccc gcccaacaag | 1680 |
| gacgtggagc | ccggcatctt | actacatggg ctgaagccct ggactcagta cgccgtttac | 1740 |
| gtcaaggctg | tgaccctcac | catggtggag aacgaccata tccgtggggc caagagtgag | 1800 |
| atcttgtaca | ttcgcaccaa | tgcttcagtt ccttccattc ccttggacgt tctttcagca | 1860 |
| tcgaactcct | cttctcagtt | aatcgtgaag tggaaccctc cctctctgcc caacggcaac | 1920 |
| ctgagttact | acattgtgcg | ctggcagcgg cagcctcagg acggctacct ttaccggcac | 1980 |
| aattactgct | ccaaagacaa | aatccccatc aggaagtatg ccgacggcac catcgacatt | 2040 |
| gaggaggtca | cagagaaccc | caagactgag gtgtgtggtg gggagaaagg gccttgctgc | 2100 |
| gcctgcccca | aaactgaagc | cgagaagcag gccgagaagg aggaggctga ataccgcaaa | 2160 |
| gtctttgaga | atttcctgca | caactccatc ttcgtgccca gacctgaaag gaagcggaga | 2220 |
| gatgtcatgc | aagtggccaa | caccaccatg tccagccgaa gcaggaacac cacggccgca | 2280 |
| gacacctaca | acatcaccga | cccggaagag ctggagacag agtacccttt ctttgagagc | 2340 |
| agagtggata | caaggagag | aactgtcatt tctaaccttc ggcctttcac attgtaccgc | 2400 |
| atcgatatcc | acagctgcaa | ccacgaggct gagaagctgg gctgcagcgc ctccaacttc | 2460 |
| gtctttgcaa | ggactatgcc | cgcagaagga gcagatgaca ttcctgggcc agtgacctgg | 2520 |
| gagccaaggc | ctgaaaactc | catcttttta aagtggccgg aacctgagaa tcccaatgga | 2580 |
| ttgattctaa | tgtatgaaat | aaaatacgga tcacaagttg aggatcagcg agaatgtgtg | 2640 |
| tccagacagg | aatacaggaa | gtatggaggg gccaagctaa accggctaaa cccggggaac | 2700 |
| tacacagccc | ggattcaggc | cacatctctc tctgggaatg ggtcgtggac agatcctgtg | 2760 |
| ttcttctatg | tccaggccaa | aacaggatat gaaaacttcg gcggcggcgg tagtggcggc | 2820 |
| ggtggcagcg | gcggtggcgg | cagtggtggc ggcggcagcg gcggcggcgg tagtggtggc | 2880 |
| tgcccagcac | ctgaactcct | gggggaccgt cagtcttcc tcttcccccc aaaacccaag | 2940 |
| gacaccctca | tgatctcccg | gacccctgag gtcacatgcg tggtggtgga cgtgagccac | 3000 |
| gaagaccctg | aggtcaagtt | caactggtac gtggacggcg tggaggtgca taatgccaag | 3060 |
| acaaagccgc | gggaggagca | gtacaacagc acgtaccgtg tggtcagcgt cctcaccgtc | 3120 |
| ctgcaccagg | actggctgaa | tggcaaggag tacaagtgca aggtctccaa caaagccctc | 3180 |
| ccagccccca | tcgagaaaac | catctccaaa gccaaggc agccccgaga accacaggtg | 3240 |
| tacaccctgc | ccccatcccg | ggaggagatg accaagaacc aggtcagcct gacctgcctg | 3300 |
| gtcaaaggct | tctatcccag | cgacatcgcc gtggagtggg agagcaatgg gcagccggag | 3360 |
| aacaactaca | agaccacgcc | tcccgtgctg gactccgacg gctccttctt cctctacagc | 3420 |
| aagctcaccg | tggacaagag | caggtggcag caggggaacg tcttctcatg ctccgtgatg | 3480 |
| cacgaggctc | tgcacaacca | ctacacgcag aagagcctct ccctgtctcc gggtaaatga | 3540 |

<210> SEQ ID NO 18
<211> LENGTH: 1179
<212> TYPE: PRT

<213> ORGANISM: Artificial Sequence
<220> FEATURE:
<223> OTHER INFORMATION: Modified human Trap H protein

<400> SEQUENCE: 18

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                    85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
```

```
                385                 390                 395                 400
            Phe Leu Lys Asn Leu Arg Leu Ile Leu Gly Glu Glu Gln Leu Glu Gly
                            405                 410                 415

Asn Tyr Ser Phe Tyr Val Leu Asp Asn Gln Asn Leu Gln Gln Leu Trp
                            420                 425                 430

Asp Trp Asp His Arg Asn Leu Thr Ile Lys Ala Gly Lys Met Tyr Phe
                            435                 440                 445

Ala Phe Asn Pro Lys Leu Cys Val Ser Glu Ile Tyr Arg Met Glu Glu
                450                 455                 460

Val Thr Gly Thr Lys Gly Arg Gln Ser Lys Gly Asp Ile Asn Thr Arg
            465                 470                 475                 480

Asn Asn Gly Glu Arg Ala Ser Cys Glu Ser Asp Val Leu His Phe Thr
                            485                 490                 495

Ser Thr Thr Thr Ser Lys Asn Arg Ile Ile Ile Thr Trp His Arg Tyr
                            500                 505                 510

Arg Pro Pro Asp Tyr Arg Asp Leu Ile Ser Phe Thr Val Tyr Tyr Lys
                            515                 520                 525

Glu Ala Pro Phe Lys Asn Val Thr Glu Tyr Asp Gly Gln Asp Ala Cys
                530                 535                 540

Gly Ser Asn Ser Trp Asn Met Val Asp Val Asp Leu Pro Pro Asn Lys
            545                 550                 555                 560

Asp Val Glu Pro Gly Ile Leu Leu His Gly Leu Lys Pro Trp Thr Gln
                            565                 570                 575

Tyr Ala Val Tyr Val Lys Ala Val Thr Leu Thr Met Val Glu Asn Asp
                            580                 585                 590

His Ile Arg Gly Ala Lys Ser Glu Ile Leu Tyr Ile Arg Thr Asn Ala
                            595                 600                 605

Ser Val Pro Ser Ile Pro Leu Asp Val Leu Ser Ala Ser Asn Ser Ser
                610                 615                 620

Ser Gln Leu Ile Val Lys Trp Asn Pro Pro Ser Leu Pro Asn Gly Asn
            625                 630                 635                 640

Leu Ser Tyr Tyr Ile Val Arg Trp Gln Arg Gln Pro Gln Asp Gly Tyr
                            645                 650                 655

Leu Tyr Arg His Asn Tyr Cys Ser Lys Asp Lys Ile Pro Ile Arg Lys
                            660                 665                 670

Tyr Ala Asp Gly Thr Ile Asp Ile Glu Glu Val Thr Glu Asn Pro Lys
                            675                 680                 685

Thr Glu Val Cys Gly Gly Glu Lys Gly Pro Cys Cys Ala Cys Pro Lys
                            690                 695                 700

Thr Glu Ala Glu Lys Gln Ala Glu Lys Glu Glu Ala Glu Tyr Arg Lys
            705                 710                 715                 720

Val Phe Glu Asn Phe Leu His Asn Ser Ile Phe Val Pro Arg Pro Glu
                            725                 730                 735

Arg Lys Arg Arg Asp Val Met Gln Val Ala Asn Thr Thr Met Ser Ser
                            740                 745                 750

Arg Ser Arg Asn Thr Thr Ala Ala Asp Thr Tyr Asn Ile Thr Asp Pro
                            755                 760                 765

Glu Glu Leu Glu Thr Glu Tyr Pro Phe Phe Glu Ser Arg Val Asp Asn
                            770                 775                 780

Lys Glu Arg Thr Val Ile Ser Asn Leu Arg Pro Phe Thr Leu Tyr Arg
            785                 790                 795                 800

Ile Asp Ile His Ser Cys Asn His Glu Ala Glu Lys Leu Gly Cys Ser
                            805                 810                 815
```

```
Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Gly Gly Gly Ser Gly Gly Gly Ser Gly
    930                 935                 940

Gly Gly Gly Ser Gly Gly Gly Ser Gly Gly Gly Ser Gly Gly
945                 950                 955                 960

Cys Pro Ala Pro Glu Leu Leu Gly Gly Pro Ser Val Phe Leu Phe Pro
                965                 970                 975

Pro Lys Pro Lys Asp Thr Leu Met Ile Ser Arg Thr Pro Glu Val Thr
            980                 985                 990

Cys Val Val Val Asp Val Ser His Glu Asp Pro Glu Val Lys Phe Asn
        995                 1000                1005

Trp Tyr Val Asp Gly Val Glu Val His Asn Ala Lys Thr Lys Pro
        1010                1015                1020

Arg Glu Glu Gln Tyr Asn Ser Thr Tyr Arg Val Val Ser Val Leu
    1025                1030                1035

Thr Val Leu His Gln Asp Trp Leu Asn Gly Lys Glu Tyr Lys Cys
    1040                1045                1050

Lys Val Ser Asn Lys Ala Leu Pro Ala Pro Ile Glu Lys Thr Ile
    1055                1060                1065

Ser Lys Ala Lys Gly Gln Pro Arg Glu Pro Gln Val Tyr Thr Leu
    1070                1075                1080

Pro Pro Ser Arg Glu Glu Met Thr Lys Asn Gln Val Ser Leu Thr
    1085                1090                1095

Cys Leu Val Lys Gly Phe Tyr Pro Ser Asp Ile Ala Val Glu Trp
    1100                1105                1110

Glu Ser Asn Gly Gln Pro Glu Asn Asn Tyr Lys Thr Thr Pro Pro
    1115                1120                1125

Val Leu Asp Ser Asp Gly Ser Phe Phe Leu Tyr Ser Lys Leu Thr
    1130                1135                1140

Val Asp Lys Ser Arg Trp Gln Gln Gly Asn Val Phe Ser Cys Ser
    1145                1150                1155

Val Met His Glu Ala Leu His Asn His Tyr Thr Gln Lys Ser Leu
    1160                1165                1170

Ser Leu Ser Pro Gly Lys
    1175
```

SOLUBLE IGF RECEPTOR FC FUSION PROTEINS AND USES THEREOF

RELATED APPLICATIONS

This application claims priority to U.S. Provisional Application No. 61/576,034, filed Dec. 15, 2011, the entire contents of which are hereby incorporated by reference.

TECHNICAL FIELD

The present invention relates to novel soluble IGF receptor Fc fusion proteins and compositions and methods of use thereof for treating cancer and metastasis.

BACKGROUND OF THE INVENTION

The receptor for the type I insulin like growth factor (IGF-IR) plays a critical role in progression of malignant disease. Increased expression of IGF-IR and/or its ligands has been documented in many human malignancies and high plasma IGF-I levels were identified as a potential risk factor for malignancies such as breast, prostate and colon carcinomas (Samani et al., 2007, Endocr Rev, 28: 20-47). Recent data have shown that the IGF axis promotes tumor invasion and metastasis through several mechanisms, and it has been identified as a determinant of metastasis to several organ sites, particularly the lymph nodes and the liver (Long et al., 1998, Exp Cell Res, 238: 116-121; Wei, et al., 2006, Ann Surg Oncol, 13: 668-676; Samani et al., 2007, Endocr Rev, 28: 20-47; Reinmuth et al., 2002, Clin Cancer Res, 8: 3259-3269). The IGF receptor can affect metastasis by regulating tumor cell survival and proliferation in secondary sites and also by promoting angiogenesis and lymphangiogenesis either through direct action on the endothelial cells or by transcriptional regulation of vascular endothelial growth factors (VEGF) A and C (reviewed in Li, S. et al., In: Liver metastasis:Biology and Clinical Management 2011; Brodt P., Editor: 233-72)).

The IGF-IR ligands include three structurally homologous peptides IGF-I, IGF-II and insulin, but the receptor binds IGF-I with the highest affinity. The major site of endocrine production for IGF-I and IGF-II is the liver (Werner & Le Roith, 2000, Cell Mol Life Sci 57: 932-942), but autocrine/paracrine IGF-I production has been documented in extra-hepatic sites such as heart, muscle, fat, spleen and kidney. The physiological activities and bioavailability of IGF-I and IGF-II are modulated through their association with 6 secreted, high-affinity binding proteins (IGFBP1-6).

IGF-IR has been validated as a target for anti-cancer therapy in various tumor types. A number of IGF-IR inhibitors are in clinical or preclinical development (see, for example, Zha, J. and Lackner, M. R., Clinical Cancer Research 2010; 16: 2512-7; Gualberto, A. and Pollak, M., Oncogene 2009; 28: 3009-21; and Li, S. et al., In: Liver metastasis: Biology and Clinical Management 2011; Brodt P., Editor: 233-72). However, targeting the IGF-I system in vivo poses several challenges: First, due to the high degree of homology between the IGF-I and insulin receptors, drugs that target the IGF axis may also affect the insulin receptor/insulin axis with undesirable effects on glucose and lipid metabolism. Hyperglycemia has, in fact, been observed as one of the undesirable effects of anti-IGF-IR therapy (Karp, D. D. et al., J. Thorac. Oncol. 2009; 4: 1397-403; Bruchim, I., et al., Expert Opinion on Therapeutic Targets 2009; 13: 1179-92; Sachdev, D. and Yee, D., Mol. Cancer Ther. 2007; 6: 1-12; Rodon, J. et al., Mol. Cancer Ther. 2008; 7: 2575-88). Moreover, inhibition of IGF-I signaling may result in altered serum growth hormone levels leading to insulin insensitivity and could potentially cause a reduction in pancreatic insulin production and diabetes (Zha, J. and Lackner, M. R., Clinical Cancer Research 2010; 16: 2512-7). Second, the use of antibody-based therapy may result in ADCC reactions leading to hematological toxicity as observed in some trials (Reidy, D. L., et al., Journal of Clinical Oncology; 28: 4240-6; Zha, J. and Lackner, M. R., Clinical Cancer Research 2010; 16: 2512-7). Furthermore, some tumors also express isoform A of the insulin receptor (IR-A) that can bind IGF-II with high affinity and this may provide an alternate survival mechanism for cancer cells whose IGF-IR has been neutralized by antibody treatment or kinase inhibitors (Zha, J. and Lackner, M. R., Clinical Cancer Research 2010; 16: 2512-7).

The use of soluble receptors (decoys) to antagonize the activity of soluble ligands for treatment of malignant disease has been taught as a potential therapeutic treatment and has become an accepted form of therapy for some conditions. Decoy receptors can inhibit the biological activity of the cognate, membrane-bound receptors by binding and decreasing ligand bioavailability for the latter receptor (Rudge, et al., 2007, Proc Natl Acad Sci USA, 104: 18363-18370). Current examples include a soluble TNF receptor (Enbrel) that is in routine clinical use for the treatment of inflammatory conditions (Richard-Miceli, C. and Dougados, M., BioDrugs 2001; 15: 251-9), as well as a VEGF-Trap (Aflibercept) that is in clinical trials for the treatment of cancer and other conditions (Rudge, J. S. et al., Cold Spring Harbor Symposia on Quantitative Biology 2005; 70: 411-8). These reagents are advantageous over antibody-based therapy because they are highly specific, bind to the ligand with high affinity, and bypass some of the undesirable effects of reagents with off-target activity.

Thus, a soluble IGF-I receptor could potentially overcome some of the shortcomings of current IGF-targeting drugs, such as, for example, cross-reaction with the insulin system, ADCC-related hematological toxicity, and the compensatory effects of insulin receptor isoform A (IR-A).

It would be highly desirable therefore to be provided with a soluble IGF-1 receptor for treatment of angiogenic-associated disorders and malignant disease, including cancer and metastasis.

SUMMARY OF THE INVENTION

In accordance with a broad aspect of the invention, there are provided fusion proteins comprising an Fc portion of an antibody and a soluble IGF-IR protein. The Fc portion may be derived from, for example, a human IgG antibody, such as an IgG1 or IgG2 antibody.

In an aspect, fusion proteins provided herein bind specifically to IGF-1 and IGF-2. In some embodiments, fusion proteins bind to IGF-1 and IGF-2 with at least about the same affinity. In some embodiments, the affinity of the fusion proteins for insulin is at least about 1000-fold lower than for IGF-1 or IGF-2. In some embodiments the fusion proteins do not bind detectably to insulin.

In some embodiments, the Fc portion of a fusion protein of the invention comprises a modified Fc portion. In one embodiment, a fusion protein comprises an Fc domain modified to remove one or more Cys residues, e.g., to replace one or more Cys residues with Ser residues. In another embodiment, a fusion protein comprises an Fc domain modified to replace an 11 aa linker with a longer, more flexible linker, e.g., a 22aa or a 37aa flexible GS linker. In an embodiment, a fusion protein comprises an Fc domain modified both to remove one or more Cys residues, e.g., to replace one or more Cys residues with Ser residues, and to replace an 11 aa linker with a longer, more flexible linker, e.g., a 22aa or a 37aa flexible GS linker. In some embodiments, fusion proteins having modified Fc domains do not produce HMW species or produce a reduced amount of HMW species compared to unmodified Fc domains.

In some embodiments, a soluble IGF-IR protein comprises or consists of the extracellular domain of IGF-IR having the amino acid sequence of SEQ ID NO: 1 or 6, or a biologically active fragment or analog thereof. In other embodiments, a soluble IGF-IR protein comprises or consists of the amino acid sequence of the extracellular domain of full-length IGF-IR having the amino acid sequence of SEQ ID NO: 4, or a biologically active fragment or analog thereof. A soluble IGF-IR protein may form the tetrameric structure of SEQ ID NO: 1, 4, or 6.

In some embodiments, a fusion protein comprises or consists of the sequence set forth in SEQ ID NO: 8 (Fc-sIGFIR, IgG1) or SEQ ID NO: 10 (Fc-sIGFIR, IgG2), or a biologically active fragment or analog thereof. The biologically active fragment or analog of the fusion protein may have, for example, at least 70%, at least 80%, at least 90%, at least 95%, or at least 98% sequence identity to the fusion protein. The biologically active fragment or analog may also retain the binding specificity of the fusion protein.

In some embodiments, a fusion protein comprises or consists of the sequence set forth in SEQ ID NO: 12 (sIGF1R-hFc-IgG1 Mod#1), SEQ ID NO: 14 (sIGF1R-hFc-IgG1 Mod#2), SEQ ID NO: 16 (sIGF1R-hFc-IgG1 Mod#3), SEQ ID NO: 18 (sIGF1R-hFc-IgG1 Mod#4), or a biologically active fragment or analog thereof. The biologically active fragment or analog of the fusion protein may have, for example, at least 70%, at least 80%, at least 90%, at least 95%, or at least 98% sequence identity to the fusion protein. The biologically active fragment or analog may also retain the binding specificity of the fusion protein.

Nucleic acids encoding the fusion proteins or biologically active fragments or analogs thereof are also provided. For example, the fusion proteins or biologically active fragments or analogs thereof may be encoded by a nucleic acid having the sequence set forth in SEQ ID NO: 5, 7, or 9, or a degenerate variant thereof. In an embodiment, fusion proteins are encoded by a nucleic acid having the sequence set forth in SEQ ID NO: 11, 13, 15, or 17, or a degenerate variant thereof. In an embodiment, nucleic acids having at least 70%, at least 80%, at least 90%, at least 95%, or at least 98% sequence identity to the sequence set forth in SEQ ID NO: 5, 7, 9, 11, 13, 15, or 17 are provided herein. Vectors comprising nucleic acids described herein are also provided.

In other aspects, pharmaceutical compositions comprising fusion proteins or biologically active fragments or analogs thereof, and a pharmaceutically acceptable carrier, are provided.

In yet other aspects, there are provided uses of fusion proteins or biologically active fragments or analogs thereof, or compositions thereof, for treating an angiogenic associated disorder or a malignant disease, such as cancer or metastasis, in a subject. For example, fusion proteins or compositions of the invention may be used to treat tumor metastasis, colorectal carcinoma, lung carcinoma, breast cancer, liver cancer, bladder cancer, lung cancer, pancreatic cancer, multiple myeloma, glioblastoma multiforme, or liver metastasis. Methods of inhibiting angiogenesis in a subject having an angiogenic associated disorder, such as tumor metastasis, colorectal carcinoma, lung carcinoma, breast cancer, liver cancer, bladder cancer, lung cancer, pancreatic cancer, multiple myeloma, glioblastoma multiforme, or liver metastasis, are also provided herein. Methods and compositions for preventing or treating cancer or tumor metastasis are provided herein as well.

In further aspects, there are provided methods of inhibiting angiogenesis in a subject having an angiogenic associated disorder comprising administering to said subject an autologous cell, e.g., a dendritic cell, a hepatocyte, or a stromal cell, genetically modified to express fusion proteins or biologically active fragments or analog thereofs. The autologous cell may be, e.g., a stromal cell, e.g., a bone marrow derived mesenchymal stromal cell.

In a still further aspect, the methods provided herein further comprise administering a fusion protein or biologically active fragment or analog thereof, or compositions thereof, in combination with another angiogenesis inhibitor and/or in combination with one or more other anti-cancer agents. The two or more agents may be administered concomitantly or sequentially.

In yet another aspect, fusion proteins or biologically active fragments or analogs, or compositions thereof, are administered via injection, e.g., intravenous or intraperitoneal injection. In another aspect, fusion proteins or biologically active fragments or analogs, or compositions thereof, are administered orally.

In an embodiment, there is provided herein a fusion protein comprising an Fc portion of an antibody and a soluble IGF-IR protein. In one embodiment, the fusion protein comprises an antibody, which is a human IgG antibody. In an embodiment, the antibody is an IgG1 or an IgG2 antibody. In an embodiment, the fusion protein binds specifically to IGF-1 and IGF-2. In one embodiment, the fusion protein binds to IGF-1 and IGF-2 with at least about the same affinity. In another embodiment, the affinity of the fusion protein for IGF-2 is higher than the affinity of the fusion protein for IGF-1. In yet another embodiment, the affinity of the fusion protein for insulin is at least about 1000-fold lower than the fusion protein's affinity for IGF-1 or IGF-2. In an embodiment, the fusion protein does not bind detectably to insulin.

In one embodiment, a fusion protein comprises a soluble IGF-IR protein comprising the extracellular domain of IGF-IR having the amino acid sequence of SEQ ID NO: 1 or 6, or a biologically active fragment or analog thereof. In an embodiment, a soluble IGF-IR protein forms the tetrameric structure of SEQ ID NO: 1 or 6. In another embodiment, a soluble IGF-IR protein consists of SEQ ID NO: 1 or 6 or a biologically active fragment or analog thereof. In yet another embodiment, a soluble IGF-IR protein comprises the extracellular domain of IGF-IR having the amino acid sequence of SEQ ID NO: 4, or a biologically active fragment or analog thereof.

In one embodiment, a fusion protein comprises an Fc portion of an antibody and a soluble IGF-IR protein, wherein the soluble IGF-IR protein consists of SEQ ID NO: 1 or 6 or a biologically active fragment or analog thereof.

In an embodiment, a fusion protein comprises the sequence set forth in SEQ ID NO: 8 or SEQ ID NO: 10. In another embodiment, a fusion protein comprises the sequence set forth in SEQ ID NO: 12, 14, 16 or 18. In yet another embodiment, there is provided herein a fusion protein consisting of the sequence set forth in SEQ ID NO: 8, 10, 12, 14, 16 or 18. In a further embodiment, there is provided herein a fusion protein comprising the amino acid sequence encoded by the nucleic acid set forth in SEQ ID NO: 7, 9, 11, 13, 15 or 17, or a degenerate variant thereof. In a still further embodiment, there is provided herein a fusion protein consisting of the amino acid sequence encoded by the nucleic acid set forth in SEQ ID NO: 7, 9, 11, 13, 15 or 17, or a degenerate variant thereof.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
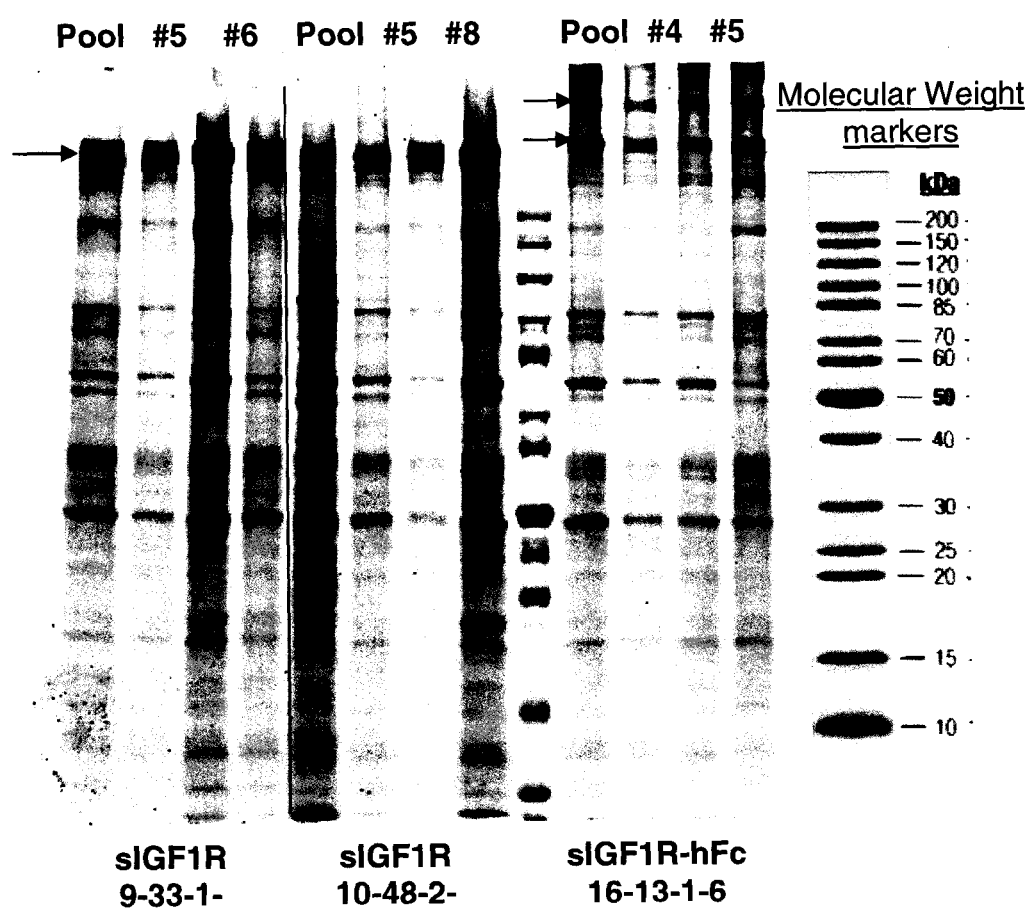
FIG. 1 shows subcloning of CHO pools of stably-transduced cell lines to identify best producers of sIGF1R (Trap D) and Fc-sIGF1R (Trap E). Three subclones of CHO cell pools were isolated: CHO-Cum2-CR5-IGF1R-9-33-1-6; CHO-Cum2-CR5-IGF1R-10-48-2-5, and CHO-Cum2-CR5-IGF1R-hFc-16-13-1-6. For each subclone, 600,000 cells/ml were cultured for 2 days at 37° C. and 7 days at 300° C. Samples analyzed by denaturing, non-reducing SDS-PAGE, 12 µl/lane, Novex® Tris-Glycine 10% TG 1.5. The lanes shown are as follows: 1: IGF1R-9-33-1-6 pool; 2: IGF1R-9-33-1-6 clone #5; 3: IGF1R-9-33-1-6 clone #6; 4: IGF1R-9-33-1-6 clone #10; 5: IGF1R-10-48-2-5 pool; 6: IGF1R-10-48-2-5 clone #5; 7: IGF1R-10-48-2-5 clone #8; 8: IGF1R-10-48-2-5 clone #12; 9: IGF1R-hFc-16-13-1-6 pool; 10: IGF1R-hFc-16-13-1-6 clone #4; 11: IGF1R-hFc-16-13-1-6 clone #5; 12: IGF1R-hFc-16-13-1-6 clone #7.

The present invention provides novel soluble IGF receptor Fc fusion proteins (Fc-sIGFR) and compositions and methods of use thereof for treating angiogenic-associated disorders and malignant disease, including cancer and metastasis.

We have previously described a 933 amino acid soluble form of the IGF-IR that exhibits a potent anti-tumorigenic/anti-metastatic activity against three different tumor types as well as anti-angiogenic properties (Wang, N., et al., Mol. Ther. 2009; 17: 1241-9; WO 2010/012088). Here, we report a novel recombinant fusion protein including the 933 amino acid soluble form of IGF-IR and the Fc portion of a human IgG antibody (Fc-sIGF-IR fusion protein).

We report also the finding that the Fc-sIGF-IR fusion proteins described herein may bind, in some cases, with high specificity and affinity to both IGF-1 and IGF-2. In some cases, the affinity of the sIGFIR-Fc fusion for IGF-2 may be unexpectedly about the same as its affinity for IGF-1. In some cases, the sIGFIR-Fc fusion may unexpectedly have higher affinity for IGF-2 than IGF-1. In some cases, the affinity of the sIGFIR-Fc fusion for IGF-1 is also increased compared to the affinity of the soluble sIGF-IR alone. Thus, we report the finding that Fc-sIGF-IR fusion proteins may, in some embodiments, bind with high affinity and with at least about the same affinity to both IGF-1 and IGF-2, in contrast to reports in the literature that IGF-IR binds IGF-2 with about 6-10 fold lower affinity than it binds IGF-1 (see, for example, Surinya et al JBC, 2008, 283: 5355-5363; Forbes, B. E., et al., Eur. J. Biochem. 2002; 269: 961-8; and Jansson, M., et al., J. Biol. Chem. 1997; 272: 8189-97). In some embodiments, however, Fc-sIGF-IR fusion proteins bind with high affinity to IGF-1 and, as expected based on reports in the literature, bind to IGF-2 with an affinity approx. 6-7 fold lower than affinity for IGF-1.

In addition, we report herein that Fc-sIGF-IR fusion proteins bind, in some embodiments, with unexpectedly high specificity to IGF-1 and IGF-2 as compared to insulin. As reported herein, sIGFIR-Fc fusion's binding affinity, as determined using surface plasmon resonance, is about 1-2000 fold lower for insulin than for the IGF-1 and IGF-2 ligands.

The Fc-sIGF-IR proteins provided herein also have an in vivo stability (half-life) in mice of between 35 and 48 hours, which would be expected to provide a half-life in humans that is amply sufficient for therapeutic applications.

It is further reported herein that the Fc-sIGF-IR proteins show enhanced potency in vitro, compared to the sIGF-IR protein, in assays for anti-cancer effects, and this in vitro activity was improved with purification. Although an increase in stability in vivo is expected with addition of the Fc portion, it was not expected that this would lead also to increased activity in vitro in anti-cancer assays.

The Fc-sIGF-IR proteins of the invention may therefore present significant therapeutic advantages compared to the sIGF-IR protein alone. Unexpectedly, the Fc portion increased the affinity of the protein for ligand (i.e., IGF-1 and IGF-2). Not only is the binding affinity of Fc-sIGF-IR for IGF-2 significantly higher than expected in some embodiments (e.g., similar to or higher than binding affinity to IGF-1, in some embodiments), but in addition the binding affinity of Fc-sIGF-IR for IGF-1 is in some cases about 2-fold higher than that of native sIGFIR alone. Without wishing to be bound by theory, it is believed that the high affinity of Fc-sIGF-IR protein to both ligands (IGF-1 and IGF-2) in some embodiments will provide significant therapeutic benefit. For example, it has been reported that tumors can develop resistance to monoclonal antibodies against IGFIR by increasing expression of IGF-1, IGF-2 and IR-A (see, for example, BioCentury, The Bernstein Report on BioBusiness, Apr. 11, 2011, page A5). Similarly, if an agent binds and inhibits only one of IGF-1 and IGF-2, then tumors can develop resistance. Higher binding specificity would also be expected to increase therapeutic benefit by limiting off-target effects. Finally, the high specificity of binding of some Fc-sIGF-IR proteins to ligand (IGF-1/2) compared to insulin may eliminate or reduce many of the unwanted side effects of other agents (e.g., antibodies, kinase inhibitors), such as undesirable effects on glucose and lipid metabolism through interaction with insulin. Further, fusion proteins having modified Fc domains may present further advantages, as discussed herein.

As used herein, the term "angiogenesis" means the proliferation of new blood vessels that penetrate into tissues or organs or into cancerous growths. Under normal physiological conditions, humans or animals undergo angiogenesis only in very restricted situations. For example, angiogenesis is normally observed in wound healing, fetal and embryonic development and formation of the corpus luteum, endometrium and placenta.

Pathological angiogenesis occurs in a number of disease states, for example, tumor metastasis and abnormal growth by endothelial cells, and supports the pathological damages seen in these conditions. The diverse pathological disease states in which abnormal angiogenesis is present have been grouped together as "angiogenic dependent" or "angiogenic associated" disorders.

Angiogenesis is tightly regulated by both positive and negative signals. Angiogenic stimulators, such as fibroblast growth factor (FGF) and vascular endothelial growth factor (VEGF), are potent mitogens for endothelial cell proliferation and strong chemoattractants for endothelial cell migration. These positive regulators can promote neovascularization to sustain the expansion of both primary and metastatic tumors. Among the negative regulators described to date, angiostatin ranks as one of the most effective endogenous inhibitors of angiogenesis.

The receptor for the type 1 insulin-like growth factor (IGF-IR) has been identified as a target for anti-cancer therapy. IGF-IR is a heterotetrameric receptor tyrosine kinase (RTK) consisting of two 130-135 kDa α and two 90-95 kDa β chains, with several α-α and α-β disulfide bridges. It is synthesized as a polypeptide chain of 1367 amino acids that is glycosylated and proteolytically cleaved into α- and β-subunits that dimerize to form a tetramer. The ligand binding domain is on the extracellular α subunit, while the β subunit consists of an extracellular portion linked to the α subunit through disulfide bonds, a transmembrane domain and a cytoplasmic portion with a kinase domain and several critical tyrosines and serine involved in transmission of ligand-induced signals (Samani et al., 2004, Cancer Research, 64: 3380-3385).

The ability of cancer cells to detach from the primary tumor and establish metastases in secondary organ sites remains the greatest challenge to the management of malignant disease. The liver is a major site of metastasis for some of the most prevalent human malignancies, particularly carcinomas of the upper and lower gastrointestinal (GI) tract. IGF-IR expression and function are critical for liver metastases formation in different tumor types. Tumor cells engineered to express a soluble form of IGF-IR (sIGFIR) lost the ability to metastasize to the liver (Samani et al., 2004, Cancer Res, 64: 3380-3385).

An effective strategy for blocking the action of cellular receptor tyrosine kinases (RTKs) is the use of soluble variants of these receptors that can bind and reduce ligand bioavailability to the cognate receptor in a highly specific manner (Kong & Crystal, 1998, J Natl Cancer Inst, 90: 273-286; Tseng et al., 2002, Surgery, 132: 857-865; Trieu et al., 2004, Cancer Res, 64: 3271-3275). One example for successful application of this strategy is the production of the VEGFR1/VEGFR2-Fc decoy receptor (the VEGF Trap) that is currently in clinical trials as a new type of anti-angiogenic, anti-cancer drug (Rudge et al., 2005, Cold Spring Harb Symp Quant Biol, 70: 411-418).

Such soluble variants of cellular receptor tyrosine kinases that bind and reduce ligand bioavailability to the cognate receptor in a highly specific manner are referred to herein as "decoy" receptors or "Trap" proteins (because they "trap" the ligand). The terms "decoy receptor", "Trap protein" (or simply "Trap") and "soluble receptor" are used interchangeably herein.

U.S. Pat. No. 6,084,085 discloses the use of soluble IGF-IR proteins for inducing apoptosis and inhibiting tumorigenesis. The soluble IGF-IR proteins disclosed in U.S. Pat. No. 6,084,085 comprise up to about 800 amino acids of the N-terminus of IGF-IR, such that the C-terminus transmembrane domain is completely deleted or is present to the extent that the protein comprising a portion of the transmembrane domain is not able to be anchored in the cell membrane. U.S. Pat. No. 6,084,085 disclosed the preferred use of a protein comprising the N-terminal 486 amino acids of IGF-IR without a signal peptide (amino acids 1 to 486), or comprising 516 amino acids with a signal peptide (amino acids −30 to 486). The proteins disclosed in U.S. Pat. No. 6,084,085 do not include the regions of the IGF-IR required for dimerization and multimerization.

International patent application No. WO/2010/012088 describes a 933 amino acid soluble form of the IGF-IR that exhibits a potent anti-tumorigenic/anti-metastatic activity against three different tumor types, both in a gene therapy setting and when injected directly into mice (see also Wang, N., et al., Mol. Ther. 2009; 17: 1241-9). This 933 amino acid soluble form of the IGF-IR is referred to herein as soluble IGF-IR, sIGFIR, sIGF-IR, sIGFIR933 or sIGFR; these terms are used interchangeably throughout. It was shown previously that sIGFR forms a complex with circulating mouse IGF-I, that bone marrow stromal cells producing a soluble IGF-I receptor inhibit the development of experimental hepatic metastases and associated angiogenesis and apoptosis; and that liver metastasis is reduced in sIGFIR injected mice. These experiments represented the first demonstration that administration of a purified sIGFR reduced metastasis and induced apoptosis of tumor cells.

However, it should be noted that in studies described previously, the treatment was prophylactic only, as sIGFIR was injected before tumor cell injection. In contrast, we report herein for the first time a therapeutic use of fusion proteins of the invention. As reported herein, fusion proteins of the invention, e.g., Fc-sIGFIR proteins, can be used therapeutically to treat tumors. For the first time, fusion proteins injected after tumor cell injection are shown to have a therapeutic effect.

We also report herein for the first time that a fusion protein including a soluble IGF-IR receptor and the Fc portion of a human IgG antibody has high binding specificity for ligand (e.g., IGF-1, IGF-2) compared to insulin, and therefore has significant potential therapeutic advantages compared to soluble IGF-IR receptor alone.

In addition, we report herein for the first time novel Fc fusion proteins having modified Fc domains. In order to avoid production of undesirable high molecular weight species (HMW) of Fc fusion proteins, novel Fc-modified fusion proteins (also referred to herein as variant proteins) were designed and produced. For example, in some modified Fc domains, cysteines in the hinge region of the Fc were replaced with serine residues. In other modified Fc domains, an 11aa linker was replaced with a 22aa flexible (GS) linker. In some modified Fc domains, both of these approaches (mutation of Fc hinge Cys residues, and utilization of a longer flexible linker) were combined. In further modified Fc domains, the Fc hinge region was truncated to retain only the lower Cys residue and the length of the flexible linker was increased to 27aa. As reported herein, these novel Fc domains reduce HMW species in fusion proteins of the invention. Further, in some embodiments, modified Fc linkers and fusion proteins may have the advantage of being sufficiently long and flexible to allow not only binding to the FcRn receptor for improved pharmacokinetic properties (half-life), but also to allow simultaneous binding of the Fc portions to the FcRγIII receptor ectodomain that may confer other beneficial properties (e.g., complement function). Our results indicate that hinge Cys residues are involved in promoting inter-molecular oligomerization, and that in some cases, a longer linker promotes intra-molecular dimerization, which may protect a Fc fragment from proteolytic degradation. In some embodiments, Fc fusion proteins of the inventions have some or all of these advantages.

Thus, in some embodiments there are provided herein fusion proteins including a soluble IGF-IR receptor and the Fc portion of a human IgG antibody, wherein the Fc portion is modified. For example, the Fc portion may be modified to remove one or more Cys residues, e.g., to replace one or more Cys residues with Ser residues, and/or to replace an 11 aa linker with a longer, more flexible linker, e.g., a 22aa or a 37aa flexible GS linker. In an embodiment, fusion proteins having a modified Fc portion do not produce HMW species or produce reduced HMW species compared to fusion proteins having an unmodified Fc portion.

Accordingly, there are provided herein Fc-sIGF-IR fusion proteins having anti-tumorigenic, anti-metastatic and/or anti-angiogenic properties.

Soluble IGF-IR receptor is referred to herein as sIGFIR, sIGF-IR, soluble IGFIR, soluble IGF-IR, sIGFR, or sIG-FIR933 and these terms are used interchangeably. The fusion protein including the soluble IGF-IR receptor is referred to herein as Fc-sIGFIR, Fc-sIGF-IR, soluble Fc-IGFIR, soluble Fc-IGF-IR, Fc-sIGFR, sIGFIR-Fc, sIGFR-Fc, Fc-sIGFIR933, etc.; these terms are used interchangeably herein.

In some embodiments, the term "about the same" as in, e.g., "about the same binding affinity", refers to two values that are approximately the same within the limits of error of experimental measurement or determination. For example, two values which are about 5%, about 10%, about 15%, about 20%, about 25%, or about 30% apart from each other, after correcting for standard error, are considered to be "about the same". Two values that are "about the same" may also be referred to as "similar" herein, as in, e.g., two proteins having similar binding affinity. In one embodiment, "about the same" or "similar" binding affinity refers to binding affinities where one affinity is not more than 2- or 3-fold greater than the other. In another embodiment, a difference in binding affinity of at least about 6-fold or at least about 10-fold means that the two binding affinities are not "about the same" or "similar".

The term "genetically-engineered stromal cell" or "transgenic stromal cells" as used herein is intended to mean a stromal cell into which an exogenous gene has been introduced by retroviral infection or other means well known to those of ordinary skill in the art. The term "genetically-engineered" may also be intended to mean transfected, transformed, transgenic, infected, or transduced. Other autologous cells may also be genetically-engineered or transgenic, e.g., dendritic cells or hepatocytes may also be used in methods and compositions of the invention.

The term "ex vivo gene therapy" is intended to mean the in vitro transfection or retroviral infection of cells, e.g., stromal cells, to form transfected cells, e.g., transfected stromal cells, prior to implantation into a mammal.

The expression "transduction of bone marrow stromal cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced bone marrow stromal cell. A bone marrow stromal cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

The term "stromal cells" as used herein is intended to mean marrow-derived fibroblast-like cells defined by their ability to adhere and proliferate in tissue-culture treated petri dishes with or without other cells and/or elements found in loose connective tissue, including but not limited to, endothelial cells, pericytes, macrophages, monocytes, plasma cells, mast cells, adipocytes, etc. Other cell types, e.g., dendritic cells, hepatocytes, may also be used in methods and compositions of the invention, and are intended to be encompassed herein. The term "autologous cells" is used herein to refer to such cells and includes, for example, stromal cells, dendritic cells, and hepatocytes.

The use of autologous cells that have a regenerative capacity and can be genetically engineered to produce effective concentrations of the desired protein is a promising therapeutic strategy (Buckley, 2000, Nat Med, 6: 623-624; Cavazzana-Calvo et al., 2000, Science, 288: 669-672; Dobson, 2000, Bmj, 320: 1225; Stephenson, 2000, Jama, 283: 589-590). Bone marrow derived mesenchymal stromal cells (BMSC) have been used to this end and have several advantages as delivery vehicles: they are abundant and available in humans of all age groups, can be harvested with minimal morbidity and discomfort, have a proliferative capacity, can be genetically engineered with reasonable efficiency and are easy to re-implant in the donor without "toxic" conditioning regimen such as radiotherapy, chemotherapy or immunosuppression. BMSCs have been validated as an efficient autologous cellular vehicle for the secretion of various beneficial proteins in vivo in both immunodeficient and immunocompetent hosts and could become an effective tool for protein delivery in clinical practice (Stagg & Galipeau, 2007, Handb Exp Pharmacol, 45-66). Thus, BMSCs autologous cells can be used as vehicles for the secretion of Fc-sIGFIR933. Any other vehicle for expressing protein known in the art is also encompassed herein, and thus BMSCs represent one embodiment of the present invention, which is not restricted to BMSCs.

We have previously shown that genetically altered stromal cells produced and secreted high levels of the soluble receptor that were detectable in the serum for up to several weeks post implantation (WO10/012088). In mice implanted with these cells, but not with control stromal cells, marked reductions in the number of hepatic metastases were seen following the injection of murine colorectal carcinoma MC-38 (up to 82% reduced) and lung carcinoma H-59 (up to 95%) cells, as well as human colorectal carcinoma KM12SM cells (up to 64%) that were inoculated into athymic nude mice. These results identified sIGFIR as a potent anti-angiogenic agent and also as a therapeutic, anti-metastatic agent.

Also encompassed within the scope of the present invention are Fc-sIGFIR933 variations and fragments, including biologically active fragments, and biologically active analogs involving amino acid deletions, additions and/or substitutions. "Biologically active fragment" includes fragments of Fc-sIGFIR933 that maintain essentially the same biological activity of the Fc-sIGFIR933 from which the fragment is derived. "Biologically active analogs" includes variations of Fc-sIGFIR933 region(s) that do not materially alter the biological activity (i.e., anti-angiogenic or anti-metastatic activity or binding specificity) of the Fc-sIGFIR933 from which the analog is derived. Included within the scope of the invention are changes made to the Fc-sIGFIR933 and Fc-sIGFIR933 fragment(s) that increase anti-angiogenic activity and/or anti-metastatic activity and/or binding specificity.

In one embodiment, an Fc-sIGFIR fusion protein of the invention includes a biologically active fragment of sIGFIR, which retains the ability to form $\alpha$-$\alpha$ and $\alpha$-$\beta$ disulfide bridges. Particularly, a biologically active fragment of sIGFIR may comprise $\alpha$- and $\beta$-subunits that dimerize to form a tetramer. In another embodiment, the invention encompasses a Fc-sIGFIR fusion protein comprising a biologically active fragment of sIGFIR which retains the disulfide bonds in the extracellular domain of the native (wild-type) receptor and/or mimics the 3D conformation of the native (wild-type) receptor. In another embodiment, a biologically active fragment of Fc-sIGFIR retains high affinity ligand binding specificity. In a further embodiment, a biologically active fragment of Fc-sIGFIR retains binding specificity for IGF-1 and/or IGF-2 as compare to insulin. For example, in an embodiment, a biologfically active fragment of Fc-sIGFIR binds IGF-1 and/or IGF-2 with an affinity at least about 100-fold or at least about 1000-fold higher than its affinity for binding insulin.

Some embodiments include analogs that incorporate modifications to the sIGFIR933 region(s) and/or fragment(s). The resulting sequences differ from the wild-type sequence of sIGFIR933 by one or more conservative amino acid substitutions or by one or more non-conservative amino acid substitutions, deletions or insertions, wherein the substitutions, deletions or insertions do not abolish the biological activity of the wild-type sequence. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

Fc-sIGFR fusion proteins having a variety of configurations are also included. For example, the N-terminus of sIGFIR may be linked by a polypeptide bond to the C-terminus of the immunoglobulin heavy chain constant region. Alternatively, the C-terminus of sIGFIR may be linked by a polypeptide bond to the N-terminus of the immunoglobulin heavy chain constant region.

As used herein, the term "immunoglobulin heavy chain constant region" is used interchangeably with the terms "Fc", "Fc region" and "Fc domain" and is understood to mean the carboxyl-terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(—CH4). CH4 is present in IgM, which has no hinge region. The immunoglobulin heavy chain constant region useful in the fusion proteins of the invention may comprise an immunoglobulin hinge region, a CH2 domain and a CH3 domain. As used herein, the term immunoglobulin "hinge region" is understood to mean an entire immunoglobulin hinge region or at least a portion of the immunoglobulin hinge region sufficient to form one or more disulfide bonds with a second immunoglobulin hinge region.

As used herein, in some embodiments "Fc" includes modified Fc domains, e.g., Fc domains which are modified to remove one or more Cys residues, e.g., to replace one or more Cys residues with Ser residues, and/or to replace an 11 aa linker with a longer, more flexible linker, e.g., a 22aa or a 37aa flexible GS linker. In an embodiment, fusion proteins having modified Fc domains do not produce HMW species or produce a reduced amount of HMW species compared to fusion proteins having unmodified Fc domains.

It is contemplated that suitable immunoglobulin heavy chain constant regions may be derived from antibodies belonging to each of the immunoglobulin classes referred to as IgA, IgD, IgE, IgG, and IgM, however, immunoglobulin heavy chain constant regions from the IgG class are preferred. Furthermore, it is contemplated that immunoglobulin heavy chain constant regions may be derived from any of the IgG antibody subclasses referred to in the art as IgG1, IgG2, IgG3, and IgG4. In one embodiment, an Fc region is derived from IgG1. In another embodiment, an Fc region is derived from IgG2.

Immunoglobulin heavy chain constant region domains have cross-homology among the immunoglobulin classes. For example, the CH2 domain of IgG is homologous to the CH2 domain of IgA and IgD, and to the CH3 domain of IgM and IgE. Preferred immunoglobulin heavy chain constant regions include protein domains corresponding to a CH2 region and a CH3 region of IgG, or functional portions or derivatives thereof. The choice of particular immunoglobulin heavy chain constant region sequences from certain immunoglobulin classes and subclasses to achieve a particular result is considered to be within the level of skill in the art. The Fc regions of the present invention may include the constant region such as, for example, an IgG-Fc, IgG-$C_H$, an Fc or $C_H$ domain from another Ig class, i.e., IgM, IgA, IgE, IgD or a light chain constant domain. Truncations and amino acid variants or substitutions of these domains may also be included.

A variety of nucleic acid sequences encoding Fc fusion proteins may also be used to make the Fc-sIGFR fusion proteins of the invention. For example, the nucleic acid sequences may encode in a 5' to 3' direction, either the immunoglobulin heavy chain constant region and the sIGFR polypeptide, or the sIGFR polypeptide and the immunoglobulin heavy chain constant region. Furthermore, the nucleic acid sequences optionally may also include a "leader" or "signal" sequence based upon, for example, an immunoglobulin light chain sequence fused directly to a hinge region of the immunoglobulin heavy chain constant region. In a particular embodiment, when the Fc region is based upon IgG sequences, the Fc region encodes in a 5' to 3' direction, at least an immunoglobulin hinge region (i.e., a hinge region containing at least one cysteine amino acid capable of forming a disulfide bond with a second immunoglobulin hinge region sequence), an immunoglobulin CH2 domain and a CH3 domain. Furthermore, a nucleic acid sequence encoding the Fc-sIGFR fusion proteins may also be integrated within a replicable expression vector that may express the Fc fusion protein in, for example, a host cell.

In one embodiment, the immunoglobulin heavy chain constant region component of the Fc-sIGFIR fusion proteins is non-immunogenic or is weakly immunogenic in the subject. The Fc region is considered non- or weakly immunogenic if the immunoglobulin heavy chain constant region fails to generate a detectable antibody response directed against the immunoglobulin heavy chain constant region. Accordingly, the immunoglobulin heavy chain constant region should be derived from immunoglobulins present, or based on amino acid sequences corresponding to immunoglobulins present in the same species as the intended recipient of the fusion protein. In some embodiments, human immunoglobulin constant heavy region sequences are used for the Fc-sIGFIR fusion protein, which is to be administered to a human. Nucleotide and amino acid sequences of human Fc IgG are known in the art and are disclosed, for example, in Ellison et al., Nucleic Acids Res. 10:4071-4079 (1982).

The Fc-sIGFR fusion proteins of the invention may be made using conventional methodologies known in the art. For example, Fc-sIGFIR fusion constructs may be generated at the DNA level using recombinant DNA techniques, and the resulting DNAs integrated into expression vectors, and expressed to produce the Fc-sIGFIR fusion proteins of the invention. As used herein, the term "vector" is understood to mean any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of an Fc-sIGFIR" fusion protein, is understood to mean the transcription of a DNA sequence, translation of the mRNA transcript, and secretion of an Fc fusion protein product. As an alternative to fusion of proteins by genetic engineering techniques, chemical conjugation using conventional chemical cross-linkers may be used to fuse protein moieties.

In an embodiment, Fc-sIGFIR fusion proteins of the invention comprise an amino acid sequence comprising the sequence set forth in SEQ ID NO: 8, 10, 12, 14, 16, or 18, and/or are encoded by a nucleic acid comprising the sequence set forth in SEQ ID NO: 5, 7, 9, 11, 13, 15, or 17. In one embodiment, the Fc region is an IgG1 Fc. In another embodiment, the Fc region is an IgG2 Fc. Intron sequences, e.g., introns in the Fc regions, may or may not be included in fusion proteins. Linker sequences between the sIGFIR and the Fc may or may not be included.

In other embodiments, Fc-sIGFIR fusion proteins of the invention consist of the amino acid sequence set forth in SEQ ID NO: 8 or 10. In other embodiments, Fc-sIGFIR fusion proteins of the invention consist of the amino acid sequence set forth in SEQ ID NO: 12, 14, 16, or 18.

In one aspect, there is provided herein a therapeutic approach for the prevention and/or treatment of angiogenic dependent or angiogenic associated disorders and/or metastatic disease, e.g. hepatic metastases, based on the sustained in vivo delivery of soluble Fc-IGFR fusion protein.

In an embodiment, compositions comprising the Fc-sIGFIR933 fusion protein described herein, or a biologically active fragment or analog thereof, which are useful to treat angiogenic-dependent or angiogenic-associated disorders and/or metastasis are provided herein. Such compositions may also include a pharmaceutically acceptable carrier, adjuvant or vehicle.

In an aspect, the compositions and methods of the invention are used to inhibit angiogenesis in a subject in need thereof, e.g. in a subject having an angiogenic dependent or angiogenic associated disorder. In one aspect, the angiogenic associated disorder is tumor metastasis, colorectal carcinoma, lung carcinoma or hepatic cancer or hepatic metastases. In another aspect, the compositions and methods of the invention are used to treat metastasis in a subject in need thereof.

The present invention includes methods of treating an angiogenic-dependent or angiogenic-associated disorder with an effective amount of a Fc-sIGFIR fusion protein or composition thereof. The present invention also includes methods of treating metastatic disease with an effective amount of a Fc-sIGFIR fusion protein or composition thereof.

Angiogenic dependent and/or angiogenic associated disorders include, but are not limited to, solid tumors, blood born tumors such as leukemias; tumor metastasis; benign tumors, for example, hemangiomas, acoustic acuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The compositions of the present invention are useful in treatment of disease of excessive or abnormal stimulation of endothelial cells. These disorders include, but are not limited to, intestinal adhesions, atherosclerosis, scleroderma, and hypertrophic scars, i.e., keloids. The compositions can also be used as birth control agents by preventing vascularization required for embryo implantation.

Additional embodiments include methods of treating a malignant tumor or a metastasis in a mammal. These methods can include selecting a mammal in need of treatment for a malignant tumor or metastasis; and administering to the mammal a therapeutically effective amount of a Fc-sIGF-IR fusion protein or composition thereof. In some aspects, the animal is human. In some aspects, the fusion protein has the sequence set forth in SEQ ID NO: 8, 10, 12, 14, 16, or 18, or is a biologically active fragment or analog thereof.

Non-limiting examples of treatable diseases include melanoma, non-small cell lung cancer, glioma, hepatocellular (liver) carcinoma, thyroid tumor, gastric (stomach) cancer, prostrate cancer, breast cancer, ovarian cancer, bladder cancer, lung cancer, glioblastoma, endometrial cancer, kidney cancer, colon cancer, pancreatic cancer, Ewing sarcoma, osteosarcoma, pancreatic carcinoma and epidermoid carcinoma. In an aspect, there are provided methods of treating colon cancer, breast cancer, liver metastasis, glioblastoma multiforme, and/or multiple myeloma comprising administering a Fc-sIGFIR fusion protein or composition thereof to a subject. In another aspect, there are provided methods of treating breast, liver, bladder, lung and/or pancreatic cancer.

The compositions and methods of the present invention may be used in combination with other compositions, methods and/or procedures for the treatment of angiogenic-dependent or angiogenic-associated disorders and/or metastasis. For example, a tumor may be treated conventionally with surgery, radiation, chemotherapy, or targeted (biological) therapy (e.g., monoclonal antibody, TKI, etc.), and then compositions comprising a Fc-sIGFIR933 fusion protein as disclosed herein may be subsequently administered to the patient to extend the dormancy of micrometastases and to stabilize any residual primary tumor.

The present invention also provides pharmaceutical (i.e., therapeutic) compositions comprising Fc-sIGFIR, or a biologically active fragment or analog thereof, optionally in combination with at least one additional active compound, and/or any pharmaceutically acceptable carrier, adjuvant or vehicle. "Additional active compounds" encompasses, but is not limited to, an agent or agents such as an immunosuppressant or an anti-cancer agent.

Non-limiting examples of anti-cancer agents which may be used in combination with compositions and methods of the invention include targeted cancer therapies and treatments, which interfere with specific mechanisms involved in carcinogenesis and tumour growth. Non-limiting examples of targeted cancer therapies include therapies that inhibit tyrosine kinase associated targets (such as Iressa®, Tarceva® and Gleevec®), inhibitors of extracellular receptor binding sites for hormones, cytokines, and growth factors (Herceptin®, Erbitux®), proteasome inhibitors (Velcade®) and stimulators of apoptosis (Genasense®). Such targeted therapies can be achieved, for example, via small molecules, monoclonal antibodies, antisense, siRNA, aptamers, gene therapy and/or cancer vaccines.

Non-limiting examples of anti-cancer treatments and procedures which may be used in combination with compositions and methods of the invention include surgery, radiology, chemotherapy, or a targeted cancer treatment. More specifically, the targeted cancer treatment is selected from the group consisting of small molecules, monoclonal antibodies, cancer vaccines, antisense, siRNA, aptamers and gene therapy. A subject may also receive a combination of treatments, procedures or therapeutic regimens. Any other treatment, procedure or therapeutic regimen known in the art can be used in the methods described herein, alone or in combination with other treatments or therapeutic regimens.

The term "pharmaceutically acceptable carrier, adjuvant or vehicle" refers to a carrier, adjuvant or vehicle that may be administered to a subject, incorporated into a composition of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS"), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compositions of the present invention.

The compositions of the present invention may contain other therapeutic agents as described herein and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compositions of the present invention may be administered by any suitable means, for example, orally, such as in the form of tablets, capsules, granules or powders; sublingually; buccally; parenterally, such as by subcutaneous, intravenous, intramuscular, intraperitoneal or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition. Preferred subjects for treatment include animals, most preferably mammalian species such as humans, and domestic animals such as dogs, cats and the like, subject to angiogenic dependent or angiogenic associated disorders.

The compositions of the present invention may be employed alone or in combination with other suitable therapeutic agents useful in the treatment of angiogenic dependent or angiogenic associated disorders, such as angiogenesis inhibitors other than those of the present invention.

The present invention will be more readily understood by referring to the following examples which are given to illustrate the invention rather than to limit its scope.

EXAMPLES

Table I shows purified sIGFIR and Fc-sIGFIR Trap proteins, which were prepared and tested as described in the Examples.

TABLE I

Figure 28:
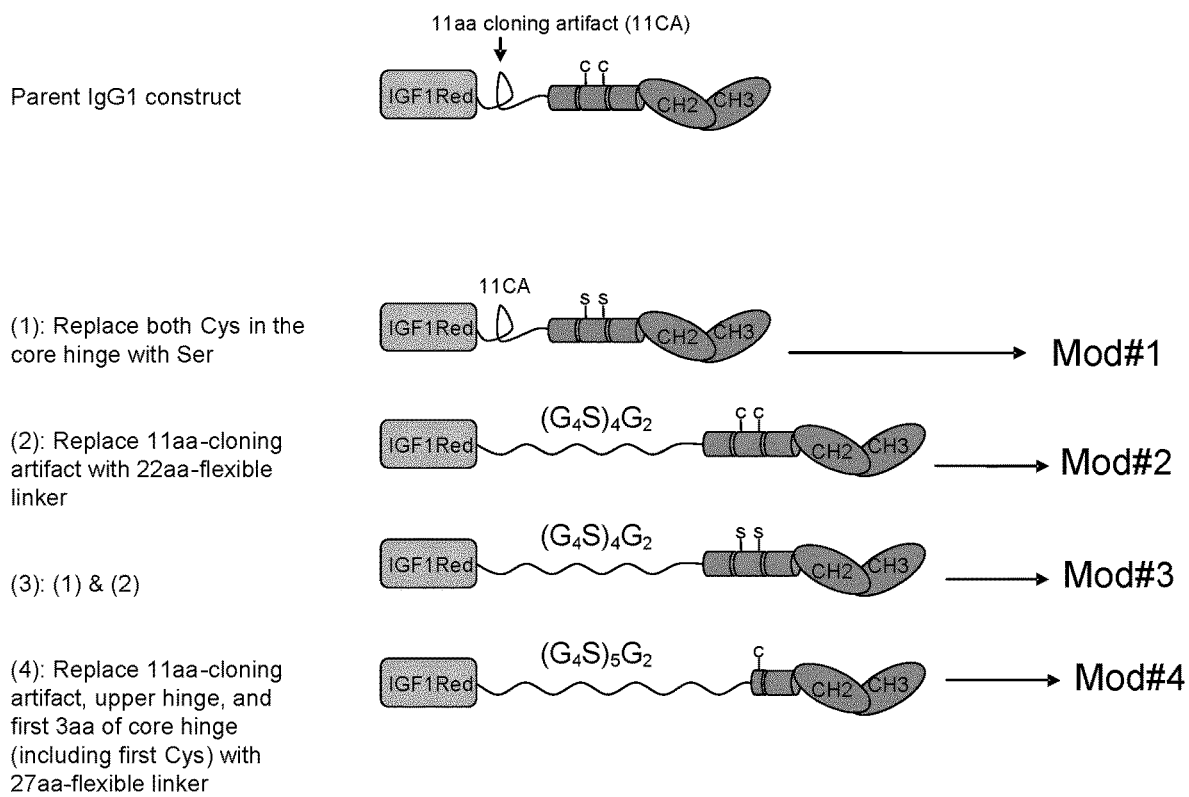
FIG. 28 shows schematic depictions of the designed sIGF1R-ed-Fc modified variant proteins. On the basis of sequence modeling of Insulin growth hormone fused to human IgG Fc fragment, we designed and generated 4 new constructs with different modifications in the junction of the sIGF1R and IgG1 sequences. The modifications are as follows: (1): Both cysteines in the core hinge were substituted with serines (referred to as sIGF1R-hFc-IgG1-Mod#1); (2): The 11 aa-cloning artifact was replaced with a 22aa-flexible linker (referred to as sIGF1R-hFc-IgG1-Mod#2); (3): A combination of 1 & 2 (referred to as sIGF1R-hFc-IgG1-Mod#3); and (4): The 11aa-cloning artifact, upper hinge, and first 3aa of core hinge (including first Cysteine) were replaced with a 27aa-flexible linker (referred to as sIGF1R-hFc-IgG1-Mod#4).

| Trap protein | Description |
|---|---|
| | Description of purified Trap proteins. |
| A | His-tagged Human- (h-) sIGF1R purified from 293 cells[1] |
| B | His-tagged h-sIGF1R purified from 293 cells[1] |
| C | His-tagged h-sIGF1R purified from 293 cells[1] |
| D | h-sIGF1R, purified from CHO cells by calcium hydroxyapatite (CHT) column followed by gel filtration (GF) |
| E | h-sIGF1R-Fc, purified from CHO cells by CHT and GF[2] (SEQ ID NO: 8) |
| F | h-sIGF1R-Fc, purified from CHO cells using protein A, pH 4.0 elution[2] (SEQ ID NO: 8) |
| G | h-sIGF1R-Fc, purified from CHO cells using protein A, pH 3.5 elution[2] (SEQ ID NO: 8) |
| H | h-sIGF1R-Fc, purified from CHO cells using protein A, pH 4.0 elution, endotoxin-free[2] (SEQ ID NO: 8) |
| I | h-sIGF1R-Fc, purified from CHO cells using protein A, pH 3.5 elution, endotoxin-free[2] (SEQ ID NO: 8) |
| Mod#1 | Modified Trap H protein, in which the cysteines in the hinge region of the Fc are replaced with serine residues (see FIG. 28; SEQ ID NO: 12) |

TABLE I-continued

Description of purified Trap proteins.

| Trap protein | Description |
|---|---|
| Mod#2 | Modified Trap H protein, in which the 11aa linker is replaced with a 22aa flexible (GS) linker (see FIG. 28; SEQ ID NO: 14) |
| Mod#3 | Modified Trap H protein, in which the cysteines in the hinge region of the Fc are replaced with serine residues, and the 11 aa linker is replaced with a 22aa flexible (GS) linker (see FIG. 28; SEQ ID NO: 16) |
| Mod#4 | Modified Trap H protein, in which the Fc hinge region is truncated to retain only the lower Cys residue, and the length of the flexible linker is increased to 27aa (see FIG. 28; SEQ ID NO: 18) |

[1]Traps A-C are different batches of the same trap protein.
[2]Traps E, F, G, H and I are the same trap protein (SEQ ID NO: 8), produced using different purification conditions.

Mod#1, Mod#2, Mod#3, and Mod#4 are modified sIGF1R-hFc-IgG1 proteins (also referred to herein as h-sIGF1R-Fc and h-sIGF1R-Fc IgG1 proteins), created by modifying a parent sIGF1R-hFc-IgG1 protein (Trap H; SEQ ID NO: 8, encoded by the DNA sequence set forth in SEQ ID NO: 7), as described in Table I and in FIGS. 27 and 28. The four modified proteins are encoded by the DNA sequences set forth in SEQ ID NOs: 11, 13, 15 and 17, respectively.

The sequence for an exemplary sIGF1R-hFc-IgG2 protein is set forth in SEQ ID NO: 10, which is encoded by the DNA sequence set forth in SEQ ID NO: 9.

Example 1

Production and Purification of Trap Proteins

We first developed and optimized a purification method for His-tagged sIGFIR. Thirteen liters of 293 cells expressing sIGF1R were produced and concentrated. The His-tagged sIGFIR was purified from the concentrated stock using IMAC-chromatography. The purified protein was used as control for developing an affinity chromatography purification protocol using insulin for sIGF1R capture. After unsuccessful attempts to capture sIGF1R on insulin columns, a new 2-step purification method was developed: a capture step on a hydroxyapatite column followed by gel filtration. Purified protein was obtained ("Traps A, B, C"; Table I) for testing. After developing the method with His-tagged sIGFIR produced in 293 cells, it was validated using tag-free sIGFIR that was produced from pooled CHO cells expressing sIGFIR and Fc-sIGFIR (i.e., without and with Fc, respectively) as described below.

Figure 2:
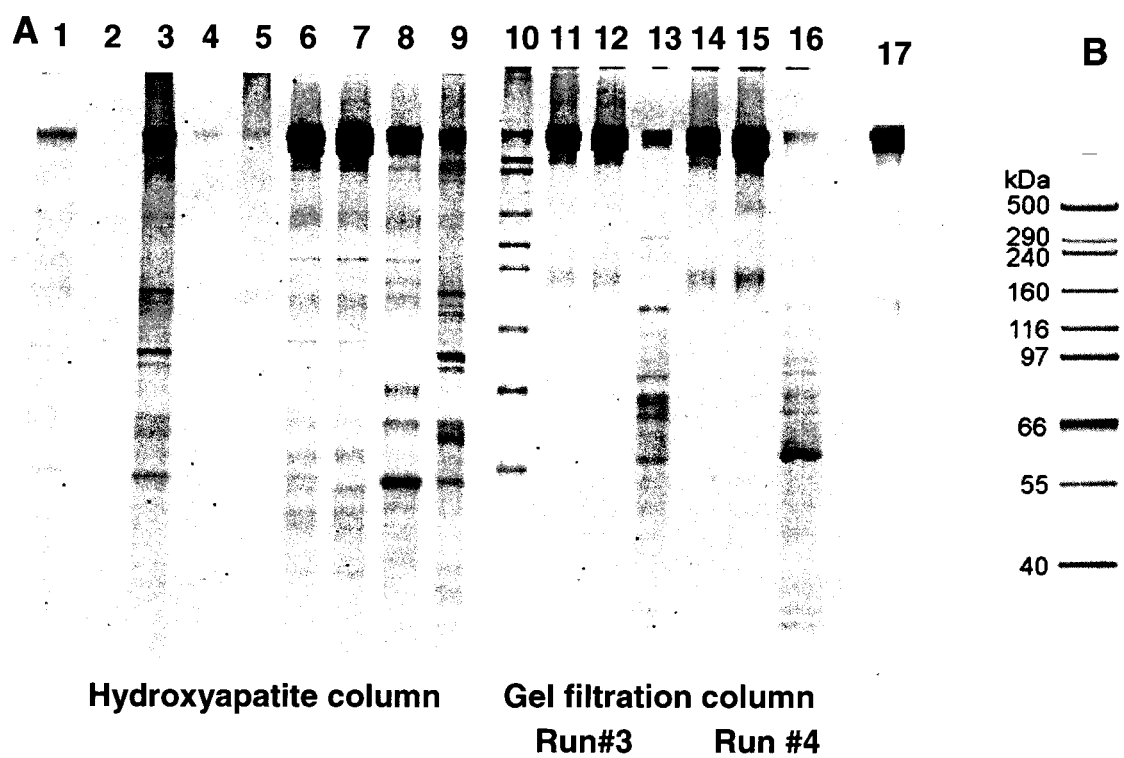
FIG. 2 shows purification of sIGF1R (Trap D) using a calcium hydroxyapatite (CHT) column followed by gel filtration. For the hydroxyapatite column, 170 ml of 400-fold concentrated & diafiltrated sIGF1R was loaded onto 25 ml of CHT column. Samples were analyzed by denaturing, non-reducing SDS-PAGE, Novex® Tris-Glycine 10% TG 1.5. SDS-PAGE is shown in (A). Samples in lanes 1-9 are from the CHT column and in lanes 10-17 are from the gel filtration column, runs #3 to 4 as indicated. The lanes shown are as follows: 1: Feed (non-concentrated), 5 µg/lane, 2: Permeate; 3: Feed (concentrated); 4: Flow-through, 0 to 115 ml; 5: Flow-through+chase; 6: Pool A2-A7, 15% B1, 7: Pool A3-A5, 15% B1, 8: Pool A10-B1, 20% B1, 9: Pool B3-B7, 100% B2 (CIP); 10: High Molecular Weight markers (details are shown in part B of the figure); 11: Run#3 A6 (5 µg); 12: Run#3 A7 (5 µg); 13: Run#3 A10 (out of range); 14: Run#4 A6 (5 µg); 15: Run#4 A7 (5 µg); 16: Run#4 A11 (out of range); 17: Purified IGF1R-CHT-GF, 2.6 µg. Molecular weight markers are shown in detail in (B). Letters and numbers (A2-A7, B1, A3-A5, A10-B1, B3-B7, B2) refer to fractions collected from columns; letters and numbers indicate position of tube on rack of fraction collector.

For purification of sIGFIR from a CHO cell pool, two independent lentivirus vectors expressing sIGF1R were generated by transient transfection of 293-PacLV cells and by producer pools as described and detailed elsewhere (Gaillet, B. et al., Biotechnol. Bioeng.; 106: 203-15). The CHO cell lines were transduced up to 6 times with lentiviruses harboring the sIGFIR gene. The CHO pools of stable cell lines were subcloned to isolate the best producer clone (FIG. 1). Production was scaled up, CHO supernatants were concentrated, and sIGFIR was purified using hydroxyapatite columns followed by gel filtration (as noted above). Purified sIGFIR ("Trap D") was obtained for testing; representative results are shown in FIG. 2.

Figure 3:
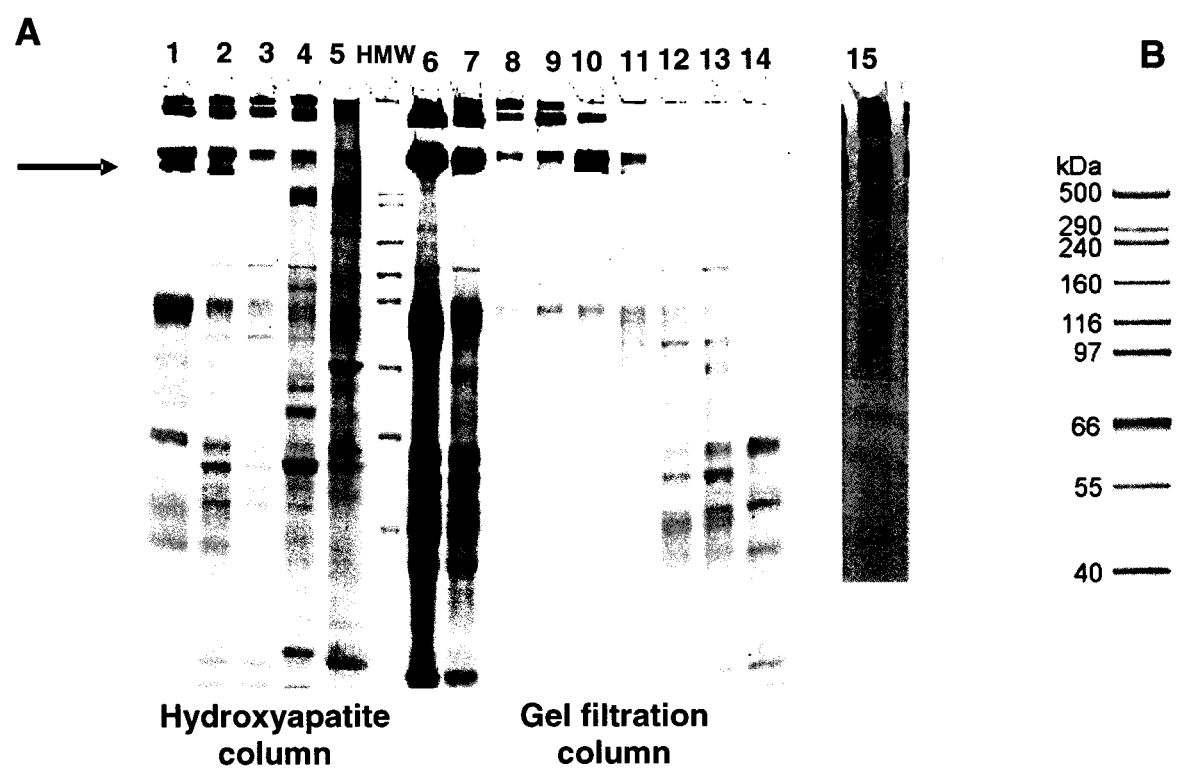
FIG. 3 shows purification of Fc(IgG1)-sIGF1R (Trap E) using a calcium hydroxyapatite (CHT) column followed by gel filtration. Samples were analyzed by denaturing, non-reducing SDS-PAGE, Novex® Tris-Glycine 10% TG 1.5. SDS-PAGE is shown in (A). Samples in lanes 1-5 are from the CHT column and in lanes 6-15 are from the gel filtration column. The lanes shown are as follows: 1: A9-A12; 2: B1-B6; B7-C1; 4: C10-D3; 5: E5-E8; 6: Feed (5 µl); 7: Feed (2 µl); 8: A9-A10, 9: A11-A12; 10: B1-B3; 11: B6; 12: B8-B9; 13: 610-B11; 14: B12-C1, and 15: Purified IGF1R-CHT-hFc-GF, 2.6 µg. The Red arrow indicates the expected position of the Fc-sIGFIR tetramer; HMW: High molecular weight markers. Molecular weight markers are shown in detail in (B). Letters and numbers (A9-A12, B1-B6, B7-C1, C10-D3, E5-E8, etc.) refer to fractions collected from columns; letters and numbers indicate position of tube on rack of fraction collector.

For purification of Fc-sIGFIR from a CHO pool, two independent lentivirus vectors expressing Fc-sIGFIR (Fc of human IgG1) were generated by transient transfection of 293-PacLV cells and by producer clones as described and detailed elsewhere (Gaillet, B. et al., Biotechnol. Bioeng.; 106: 203-15). The CHO cell lines were subsequently transduced up to six times with lentivirus vectors harboring the Fc-sIGFIR gene. The pools of stably transduced CHO cell lines were subcloned to select the best producer clones (FIG. 1). Large-scale production of Fc-sIGFIR was then initiated, CHO supernatants harvested and concentrated, and Fc-sIGFIR purified using hydroxyapatite columns followed by gel filtration. Purified Fc-sIGFIR ("Trap E") was obtained for testing; representative results are shown in FIG. 3.

Figure 4:
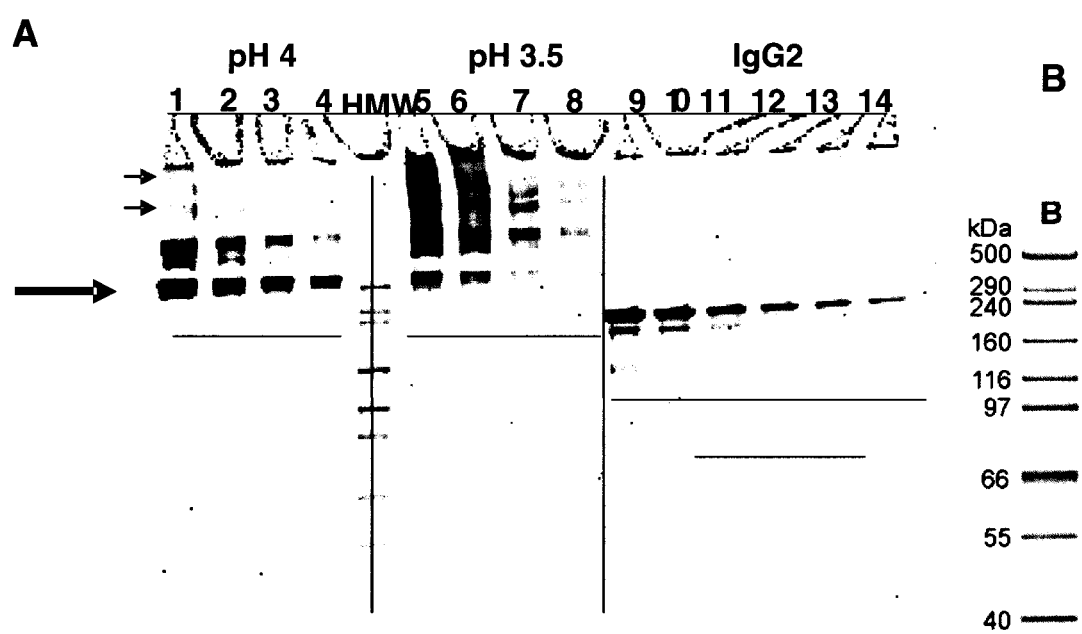
FIG. 4 shows purification of Fc(IgG1)-sIGF1R (Traps F and G) using protein A chromatography. Samples were analyzed by denaturing, non-reducing SDS-PAGE, Novex® Tris-Glycine 4-20% TG 1.5. SDS-PAGE is shown in (A). Samples in lanes 1 to 4 are from purification of Trap F (eluted at pH 4); lane 1: 2 µl; lane 2: 1 µl; lane 3: 0.5 µl; lane 4: 0.25 µl/lane; lane HMW: High molecular weight markers. Samples in lanes 5 to 8 are from purification of Trap G (eluted at pH 3.5); lane 5: 1 µl; lane 6: 0.5 µl; lane 7: 0.25 µl; lane 8: 0.125 µl/lane. Samples in lanes 9 to 14 show IgG2 (purchased from Sigma), lane 9: 3 µg; lane 10:2 µg; lane 11: 1 µg; lane 12: 0.5 µg; lane 13: 0.25 µg; lane 14: 0.125 µg. The Red arrow indicates the expected position of the Fc-sIGFIR tetramer; the Black arrows indicate high molecular weight (HMVV) species.
Figure 5:
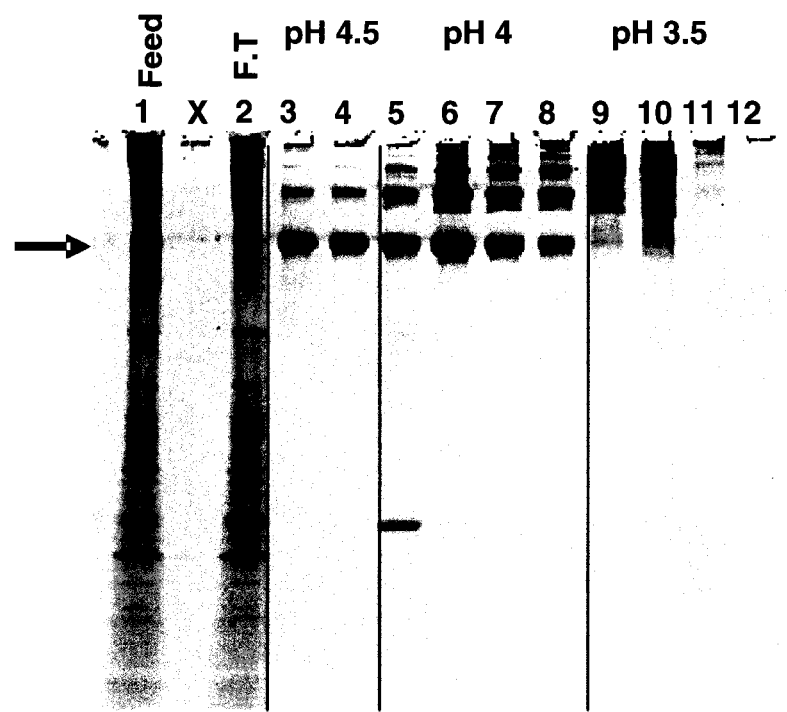
FIG. 5 shows purification of endotoxin-free Fc(IgG1)-sIGF1R (Traps H and I) using protein A chromatography. Samples were analyzed by denaturing, non-reducing SDS-PAGE, Novex® Tris-Glycine 4-20% TG 1.5. SDS-PAGE is shown in (A). 14 µl/lane was loaded. Samples in lanes 5 to 8 are from purification of Trap H (eluted at pH 4). Samples in lanes 9 to 12 are from purification of Trap I (eluted at pH 3.5). Lane 1: Feed; lane X: nothing loaded; lane 2: Flow-through (F.T.); lane 3: A1-A2; lane 4: A3-A4; lane 5: A6-A7; lane 6: A8-A10; lane 7: A11-A12; lane 8: B1-B2; lane 9: B3-B4; lane 10: B5-B6; lane 11: B7-B10; lane 12: B11-B12. The Red arrow indicates the expected position of the Fc-sIGFIR tetramer. Letters and numbers (A1-A2, A3-A4, A6-A7, A8-A10, A11-A12, B1-B2, etc.) refer to fractions collected from columns; letters and numbers indicate position of tube on rack of fraction collector.

A fraction of Fc-sIGF1R was also purified using protein A chromatography. High molecular weight (HMVV) species were detected in the crude and purified preparations, but elution at low pH (4.0-4.5) partially reduced the HMW protein fraction in the preparations (FIGS. 4 & 5). It is noted that by using a pH step elution of IGF1R-hFc bound to protein A, approximately half of the high molecular weigh (HMVV) species could be removed.

Purified Fc-sIGF1R was eluted at pH 4.0 ("Trap F") and pH 3.5 ("Trap G") for testing; representative results are shown in FIG. 4. For purified Trap F (pH 4), the Bio-Rad DC Protein micro-assay indicated 2.7 mg/ml (2.27 ml total); Gel scanning results showed 3 to 3.2 mg/ml with a purity of 100%.

Endotoxin-free batches of these Fc-sIGF1R preparations were also produced and eluted at pH 4.0 ("Trap H") and pH 3.5 ("Trap I") for additional in vivo studies; representative results are shown in FIG. 5. For endotoxin-free Trap H (pH 4.0) and Trap I (pH 3.5) in FIG. 5, 304 ml of production CHO-cum2-CR5-IGF1R-hFc-(IgG1)-16-13-1-6#7 was loaded into mabSelect SuRe 2.08 ml, 10.75 cm H, lot #10029791. Sanitization was in 0.5M NaOH, A11 to A14, Pump 690, F2, F8 ON; A15 and column, 1 h30 with 0.5M NaOH+overnight with 0.1M NaOH; binding buffer was 20 mM sodium phosphate pH 7; and elution was with sodium citrate 0.1 M, pH 4.5, 4, 3.5 & 2.5. (Letters and numbers, such as A1 to A15, B1 to B15, C1, D1, E1, and so on, refer to fractions collected from columns; letters and numbers indicate position of tube on rack of fraction collector. Two types of fraction collectors were used; for small tubes, the positions were A1 to A15, B1 to B15 and so on, and for large tubes the positions were A1 to A12, B1 to B12, and so on).

We also generated an alternative Fc-sIGFIR fusion protein using the Fc region of human IgG$_2$. The production of HMW species with this fusion protein could be reduced due to increased stability in the hinge region, thereby eliminating concerns regarding potential secondary effects of HMW species.

It will be appreciated that stable CHO lines capable of industry grade production of Trap proteins can also be produced using standard methods known in the art.

Example 2

Analytical Assays for Quality Control of Trap Proteins

For characterization of Trap proteins, analytical assays to determine, for example, purity, integrity, aggregation and glycosylation of the proteins, were developed. Both sIGFIR and Fc-sIGFIR proteins appeared to be significantly pure, except for the presence of HMW species in the Fc-sIGFIR preparations, based on gel scanning (See FIG. 2, for which gel scanning indicated purity of 95 to 97% for sIGFR for lane 17; and FIG. 3, for which gel scanning indicated purity of 94% for Fc(IgG$_1$)-sIGF1R for lane 15). No aggregation of either protein was observed after several months of storage at 4° C. or −70° C.

Figure 7:
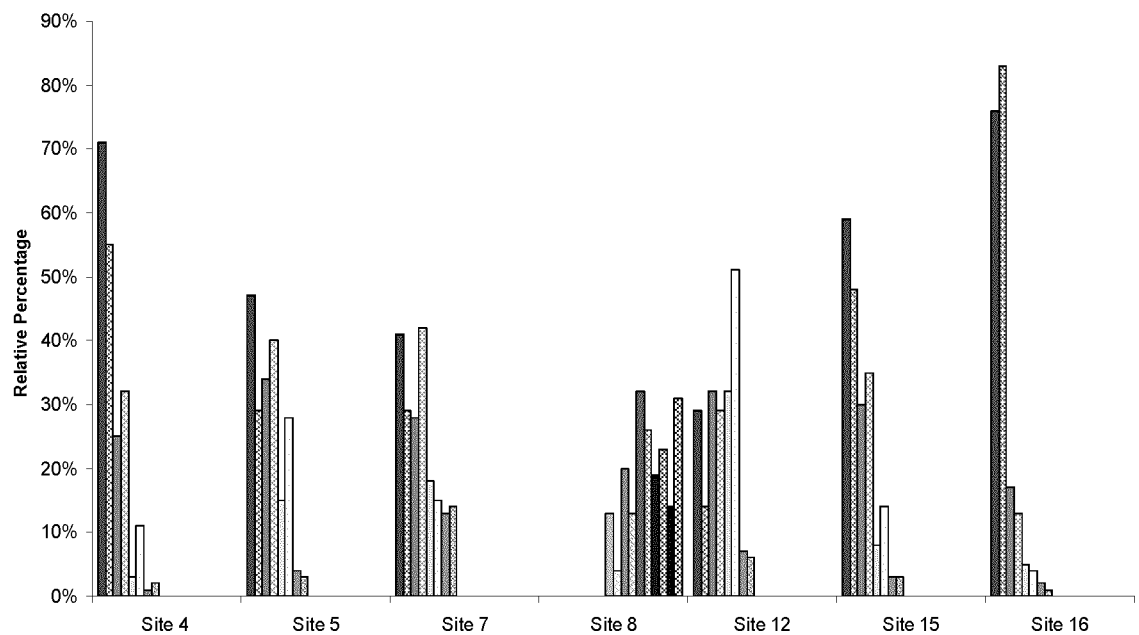
FIG. 7 shows a comparison of the most predominant glycopeptides of sIGF1R and sIGF1R-hFc by mass spectrometry. In (A), relative percentage refers to the types of sugars attached at each glycosylation site; sites 4, 5, 7, 8, 12, 15 and 16 are glycosylation sites in the peptides; solid bars represent sIGF-IR (Trap D); cross-hatched bars represent sIGF-IR-hFc (Trap E); and the colors indicate the nature of the glycosylation, as indicated in the legend shown in (B).
Figure 7:
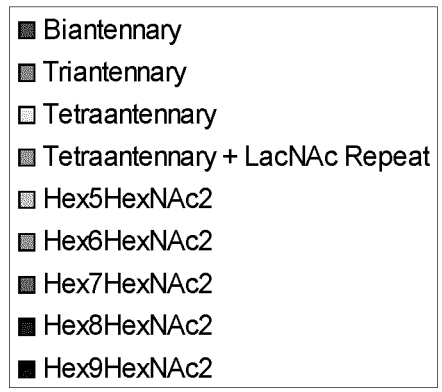

Glycosylation patterns in the two proteins were analyzed by mass spectrometry (FIG. 7). The analysis showed that sIGFIR ("Trap D") and Fc-sIGFIR ("Trap E") have 19 and 20 potential N-linked sites, respectively. Each site is decorated with a variety of glycans differing in size and degree of sialilation. The glycoform distribution varies between sites, but small, bi-antennary glycoforms are most common at most sites. Glycoform distribution and degree of sialilation, but not glycan type, were found to differ between sIGFIR and Fc-sIGFIR. Overall, Fc-sIGF1R was found to contain more complex (larger), less sialilated glycans than sIGFIR.

Example 3

Functional In Vitro Assays for sIGFR and Fc-sIGFR Proteins

In order to select the most sensitive and functional in vitro assays for tesing the decoy proteins of the invention, we first used 4 different in vitro assays to measure the effect of purified Trap proteins on tumor cell properties relevant to malignant progression and metastasis (Table I). Namely, we measured the ability of the Trap proteins to block tumor proliferation, cell survival, anchorage independent growth, and invasion in the presence of IGF-I. For all experiments, we used highly metastatic Lewis lung carcinoma subline H-59 cells. After the initial screening, we selected the anoikis and invasion assays for complete analyses of all Trap proteins because of they are: (i) semi-automated, (ii) less subject to user-dependent variability, (iii) have superior reproducibility, and (iv) are considered better in vitro correlates of the metastatic potential of tumor cells. The results of all functional in vitro assays are summarized below.

Figure 8:
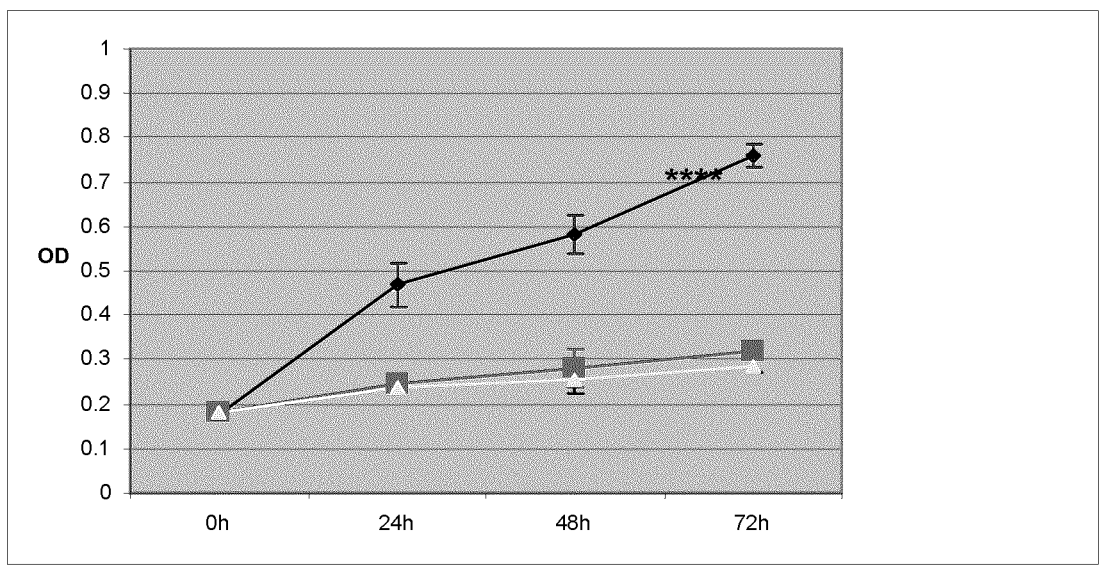
FIG. 8 shows that Traps D and E inhibit tumor cell proliferation in response to hIGF-I equally. (A) shows a plot of OD vs. time where 10 ng/mL IGF-I was used; (B) shows a plot of OD vs. time where 50 ng/mL IGF-I was used. ♦ indicates IGFI; ■ indicates sIGF-IR (Trap D)+IGFI; ▲ indicates sIGF-IR-hFc (Trap E)+IGFI and **** indicates $p<0.001$ at all time points tested.
Figure 8:
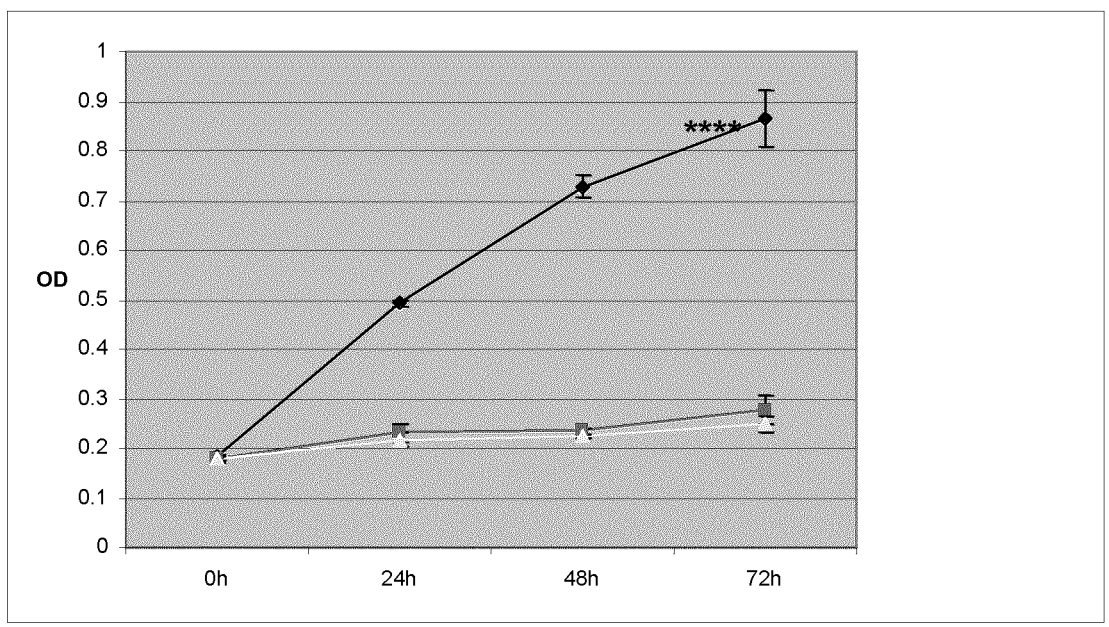

Proliferation was measured using the colorimetric (3-(4, 5-Dimethylthiazol-2-yl)-2,5-diphenyltetrazolium bromide (MTT) assay. After preliminary analyses to optimize the assay conditions, the cells were serum starved overnight and then incubated with 10 or 50 ng/ml IGF-I in the presence or absence of purified Traps D and E at a concentration calculated to deliver an IGF-I:Trap molar ratio of 1:1. The results (FIG. 8) showed a complete inhibition of cell proliferation in the presence of either 10 ng/ml or 50 ng/ml IGF-I ($p<0.001$ at all time points).

Figure 9:
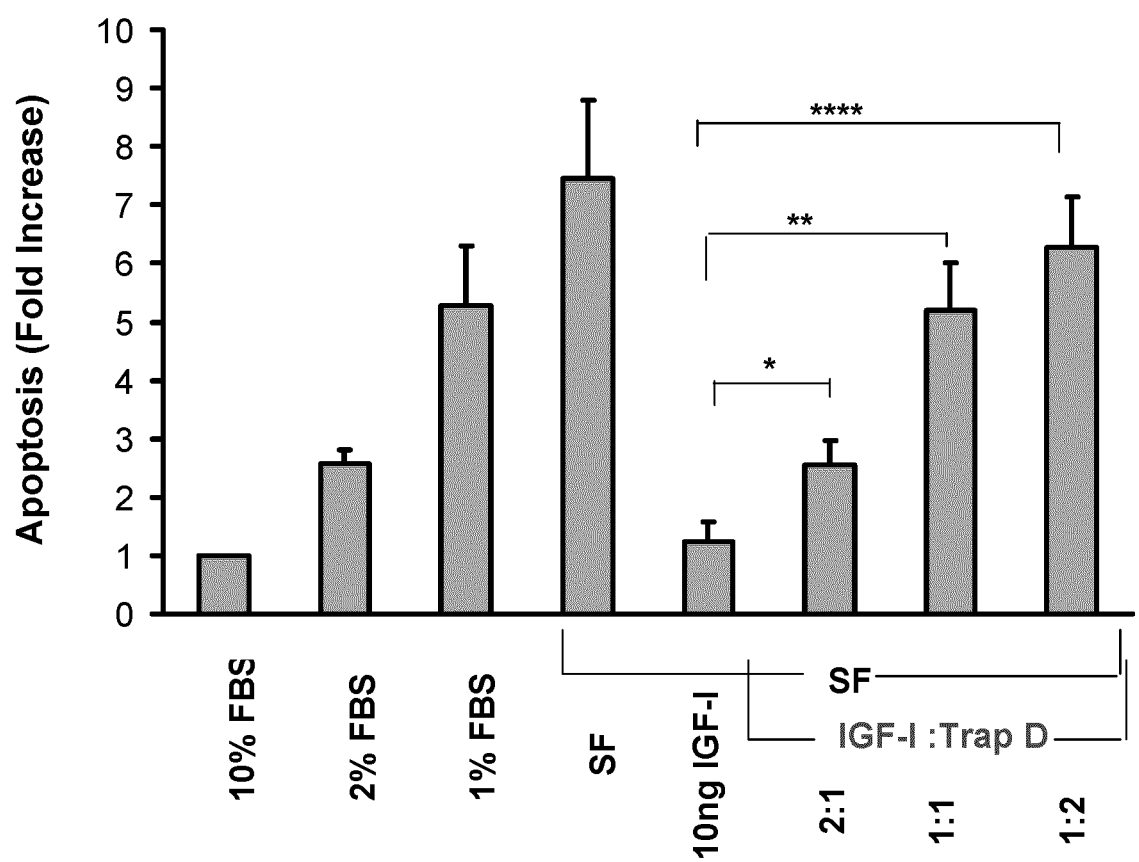
FIG. 9 shows a dose-dependent increase in anoikis (detachment-induced apoptosis) in the presence of Trap D. FBS: Fetal Bovine Serum; SF: Serum-free; "IGF-I: Trap D" is the molar ratio of IGF-I to Trap D, which is 2:1, 1:1 or 1:2 as indicated; * indicates $p<0.05$;  indicates $p<0.01$; and ** indicates $p<0.001$.
Figure 10:
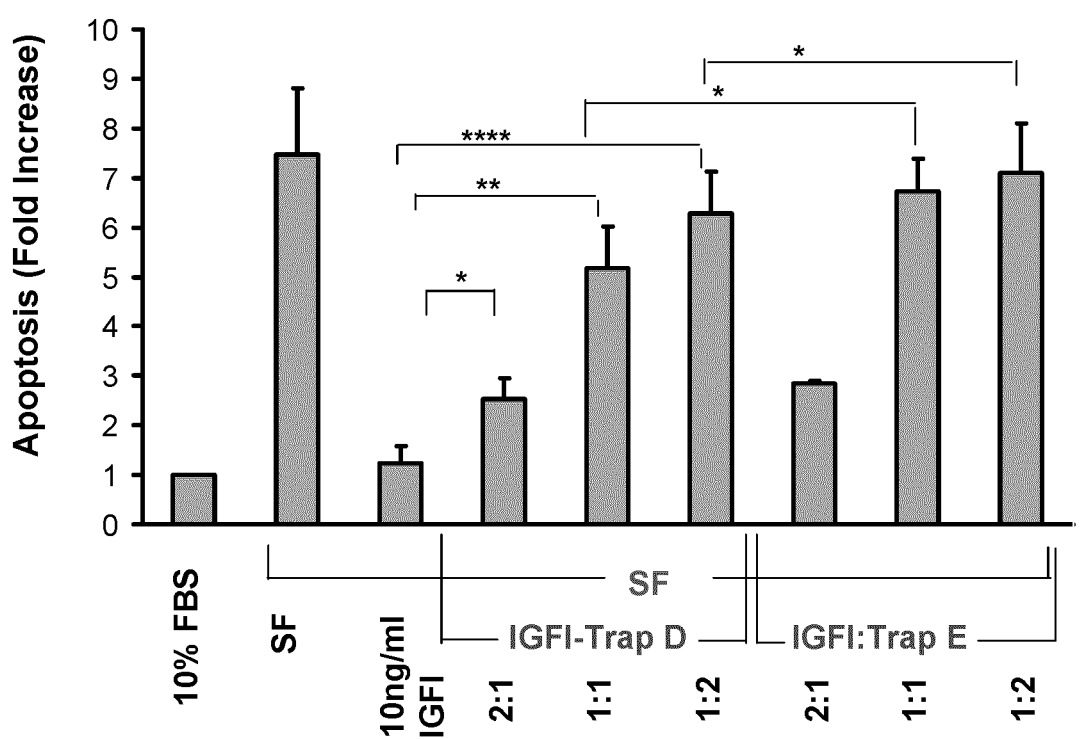
FIG. 10 shows a dose-dependent increase in anoikis (detachment-induced apoptosis) in the presence of Traps D and E and a comparison between Traps D and E. FBS: Fetal Bovine Serum; SF: Serum-free; Ratios are IGF-I:sIGFIR molar ratios (2:1, 1:1 or 1:2 as indicated); * indicates p<0.05;  indicates p<0.01; and ** indicates p<0.001. The data illustrate superior performance of Trap E (Fc-sIGFIR).

Cell survival was analyzed using the anoikis (detachment-induced apoptosis) assay, as previously described (Burnier, J. V., et al., Oncogene, 30: 3766-83, 2011]). Briefly, tumor cells ($2.5\times10^5$/well) were plated in 24-well plates that were pre-coated with 10 mg/ml PolyHEMA (Sigma) to prevent their attachment; they were then incubated at 37° C. for 48 hr in the presence of serum or serum-free medium containing IGF-I, with or without Traps D and E. At the end of the incubation period, apoptosis was analyzed using the In Vivo Cell Death Detection-RED staining kit (Roche Canada) as per the manufacturer's instructions. Results of this analysis clearly identified IGF-I as a survival factor in this assay and showed that dose-dependent increases in anoikis (i.e., blockage of pro-survival/anti-apoptotic effect of IGF-I) with Trap E were more significant compared to Trap D (FIG. 9; $p<0.05$). Furthermore, subsequent Trap purification using protein A columns (i.e., Traps F and G) improved somewhat their ability to block the anti-apoptotic effect of IGF-I, especially at the lower Trap: IGF-I ratio of 1:2 (FIG. 10; $p<0.05$).

Figure 11:
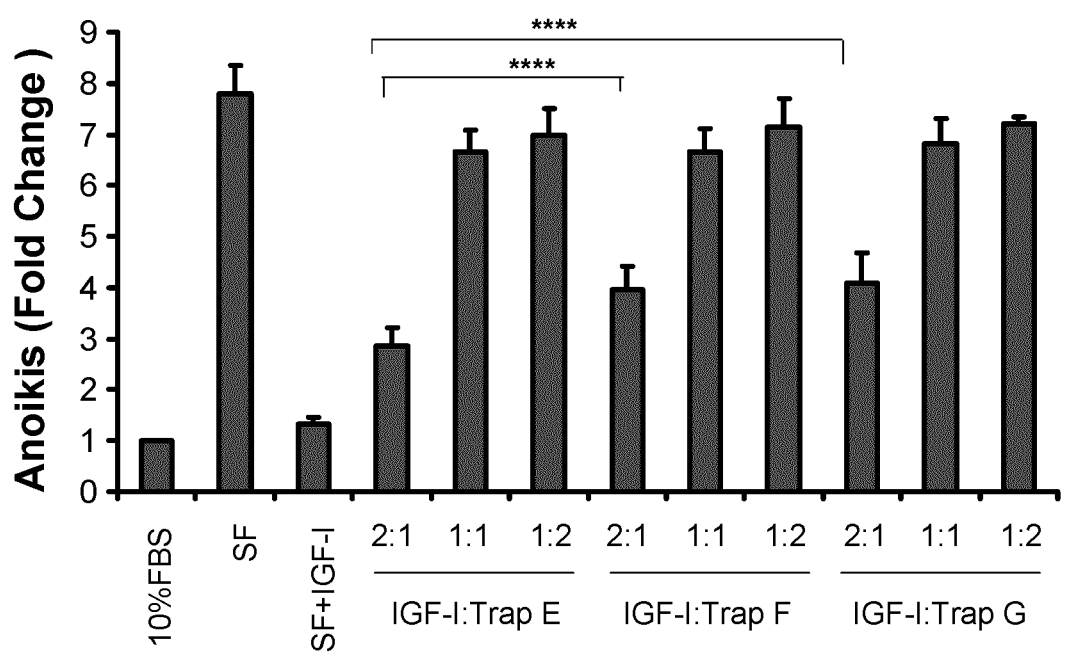
FIG. 11 shows increased anoikis in the presence of the IGF-Traps E, F and G, illustrating the effect of protein A purification. FBS: Fetal Bovine Serum; SF: Serum-free; Molar ratios of IGF-I:Trap protein are as indicated; **** indicates p<0.001.

Anchorage independent tumor cell growth was measured using the semi-solid agar clonogenicity assay, as previously described (Brodt, P. et al., J. Biol. Chem. 2001; 276: 33608-15). Briefly, tumor cells in RPMI medium containing the indicated concentration of FCS, with or without IGF-I, were mixed with a 0.8% agarose solution (at 1:1 ratio) and plated onto 35 mm culture dishes ($2\times10^4$ cells/dish) on a solidified 1% agarose layer. To the overlay, RPMI medium containing the same concentration of FCS was added and the plates incubated at 37° C. for 14 days, at which time the cells were fixed and colonies exceeding 80 µM in diameter scored using a microscope equipped with an ocular grid. Results of this assay (FIG. 11) showed that Trap D and Trap E significantly reduced the ability of the tumor cells to form colonies in semi-solid agar ($p<0.01$ at all conditions) and there was only a minor difference in the activities of the two Traps under these assay conditions ($p<0.05$ only in the presence of 1% FCS).

Figure 6:
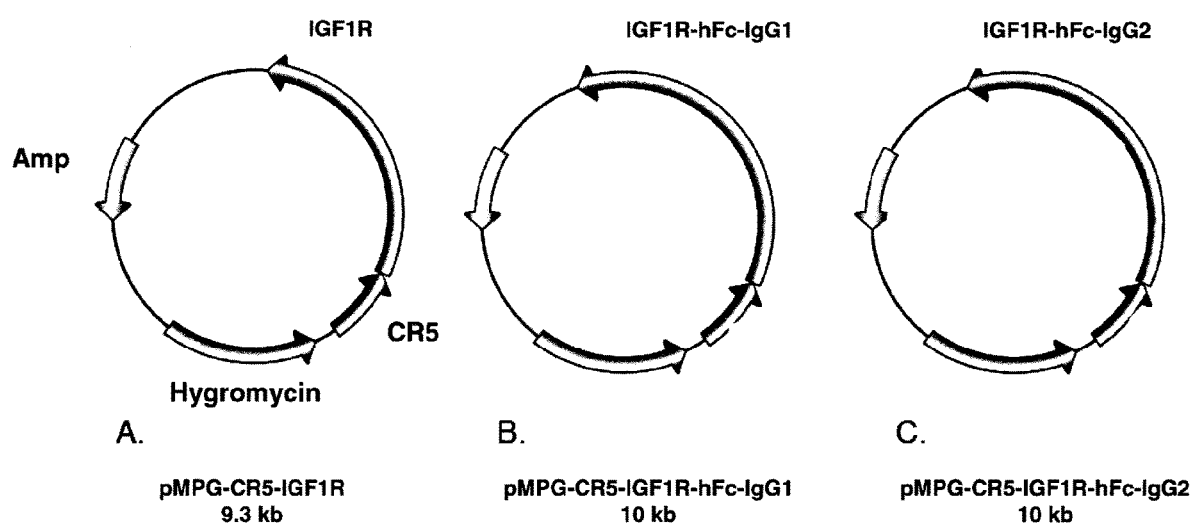
FIG. 6 shows a schematic representation of vectors used to make Trap proteins of the invention. The sIGF1R sequence was inserted into the pMPG-CR5 vector as shown in (A), and the sIGF1R sequence fused to either the human IgG1 Fc or IgG2 Fc was inserted into the pMPG-CR5 vector as shown in (B) and (C), respectively. These vectors were used for transient or stable expression of Trap proteins in CHO cells.
Figure 12:
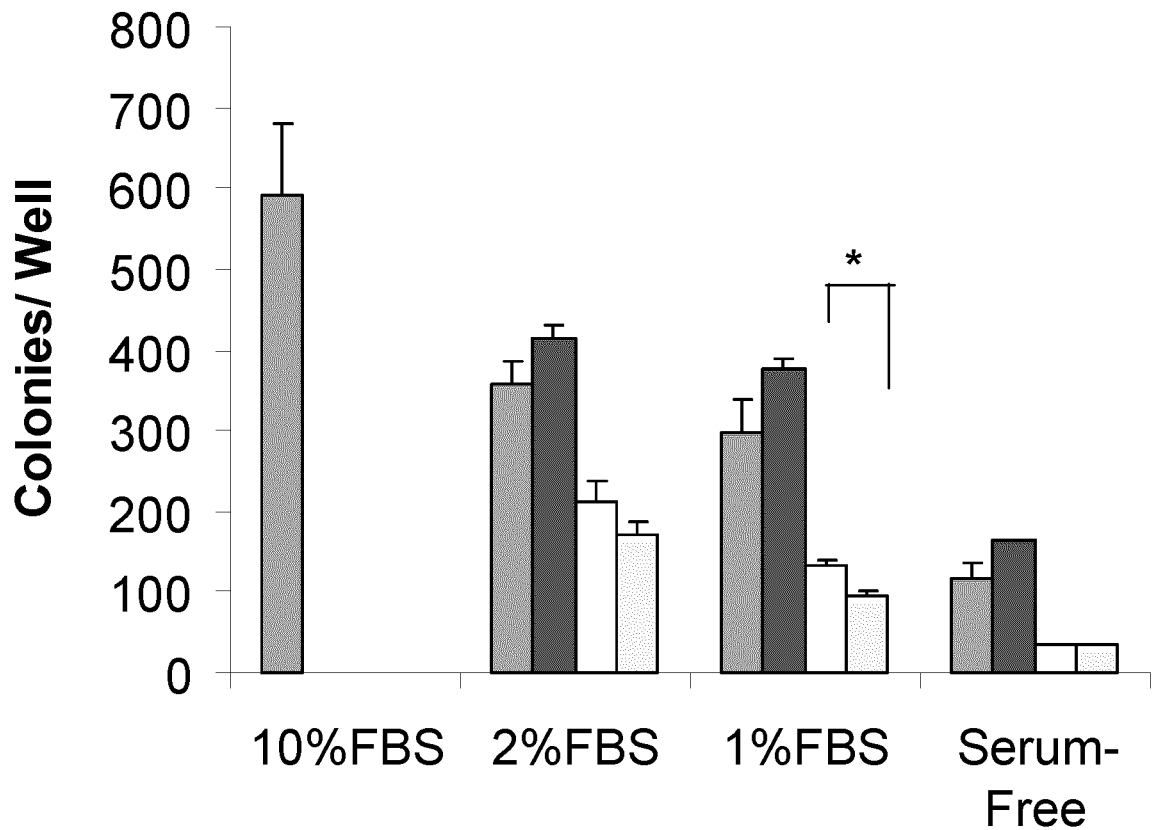
FIG. 12 shows reduced anchorage-independent growth in the presence of Traps D and E, and a comparison between Traps D and E. In (A) it is shown that the number of colonies was significantly reduced in the presence of the Traps; *indicates p<0.05; p was <0.01 under all conditions tested. Colors indicate the proteins tested, as indicated in the legend shown in (B). The data illustrate superior performance of the Fc fusion protein.
Figure 13:
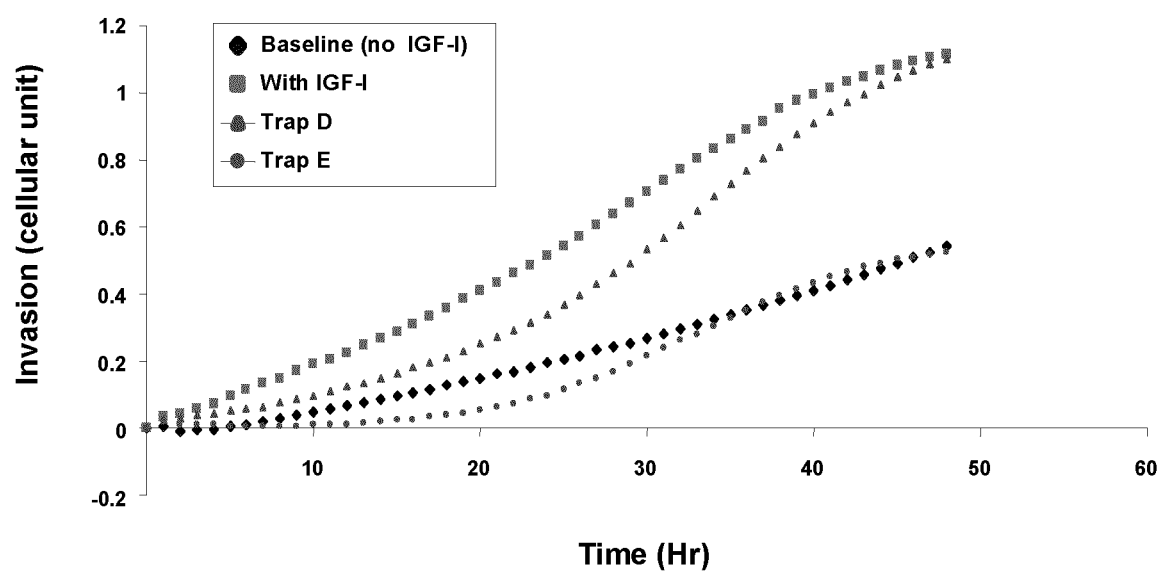
FIG. 13 shows a time course analysis indicating the effect of Traps D and E on tumor cell invasion and a comparison between Traps D and E. Blue line (♦) represents baseline (no IGF-I), Pink line (■) indicates invasion with IGF-I; Green line (▲) indicates Trap ID, and Red line (●) indicates Trap E.

Tumor cell invasion was measured using a real-time, electrical-impedance-based technique using the new, automated xCELLligence™ system (Roche). The xCELLigence™ instrument measures changes in electrical impedance at an electrode/cell interphase, as a population of (malignant) cells invades a Matrigel layer and migrates to a lower chamber of a Boyden-chamber system. The impedance is displayed as a dimensionless parameter termed cell-index (or cellular unit), which is directly proportional to the total area of tissue-culture well that is covered by cells, as described and demonstrated by others (Ungefroren, H. et al., Int. J. Oncol.; 38:797-805; Rahim, S. and Uren, A., J. Vis. Exp., 50: 1-4, 2011). Tumor H-59 cells (in the upper chamber) were plated in wells ($5\times10^4$ cells/well) that were pre-coated with the extracellular matrix mixture Matrigel™ (BD Biosciences) at a concentration pre-determined to allow optimal invasion. They were then placed on top of a lower chamber containing 50 ng/ml IGF-I to which the indicated IGF-Traps were added (or not) at different (approximate) IGF: Trap molar ratios. When the inhibitory effects of Trap D (sIGF1R) and Trap E (Fc-sIGF1R) on cell invasion were compared at a Trap:IGF-I molar ratio of 1:1 (FIG. 13), they demonstrated an apparent increased activity for Trap E ($p<0.05$ at 36 hr). Following protein A purification without (i.e. Traps F and G; FIG. 12) or with (Traps H and I; FIG. 13) endotoxin removal, the enhanced activity of all these preparations indicated that the significant inhibition seen was not related to non-specific effects of endotoxin. It should be noted that in the invasion assays, fractions eluted at pH 3.5 (i.e. enriched for high molecular weight species, see FIGS. 5 and 6) appeared more active than those depleted of high molecular weight species ($p<0.01$), suggesting that the high molecular weight proteins retained an IGF-I "trapping" ability.

It can be seen from the results presented here that, surprisingly, the Fc-sIGFR protein demonstrated increased potency in vitro in these anti-cancer assays compared to the sIGFR protein, and this enhanced potency of the Fc-sIGFR protein was improved with purification.

Example 4

Binding Specificity and Affinity of sIGFR Vs. Fc-sIGFR

Binding between purified Trap receptors ("A" to "I") and IGF-IR ligands (mIGF-1, hIGF-1, hIGF-2, and human insulin) was measured using label-free, real-time Surface Plasmon Resonance (SPR). Experiments were performed at 25°

C. using BIACORE™ 3000 instrumentation (GE Healthcare Bio-Sciences AB, Uppsala, Sweden) as described by others (Forbes, B. E., et al., Eur. J. Biochem. 2002; 269: 961-8; Jansson, M., et al., J. Biol. Chem. 1997; 272: 8189-97; Surinya, K. H., et al., J. Biol. Chem. 2008; 283: 5355-63). Initially, the ligands were immobilized (~125 RU; Biacore Amine Coupling Kit) to dextran-coated sensor chips and the receptors were titrated over reference (i.e., no ligand) and ligand surfaces in tandem. In reciprocal experiments, the ligands were titrated over immobilized Trap surfaces (~8000 RU). Mass transport-independent data were double-referenced (Myszka DG. Improving biosensor analysis. J Mol Recognit 1999; 12: 279-84) and were representative of duplicate injections acquired from two independent trials. For the multi-cycle titrations, equilibrium dissociation constants ($K_D$) were determined by global fitting of the data to a "1:1 kinetic" model (BIAevaluation v4.1 software) or the "steady-state affinity" model (for human insulin titrations only). For the single-cycle titrations, $K_D$ values were determined by local fitting of the data to a "1:1 titration" model (Karlsson, R., et al., Anal. Biochem. 2006; 349: 136-47).

His-tagged sIGFIR variants ("Traps A, B, C") were initially tested and used to standardize assay conditions for Trap binding to amine-coupled ligand surfaces in preparation for subsequent analysis of Trap proteins. Over nanomolar titration ranges, Trap B exhibited the best overall activity and its binding to immobilized mouse or human IGF-I was significant compared to little or no response with human insulin (specificity control; micromolar affinity) or maltose-binding protein (negative control; no affinity). In reciprocal experiments, hIGF-I was titrated and bound to HEK293-purified Trap B and CHO-purified Trap D and E surfaces with nanomolar affinity, whereas human insulin bound with weaker, micromolar affinity in all cases (Table II). On average, Traps B, D, and E exhibited similar association and dissociation rate constants ($k_a$ ~2.6×10$^5$ M$^{-1}$ s$^{-1}$ and $k_d$ ~2×10$^{-3}$ s$^{-1}$, respectively) in these multi-cycle trials. The results confirmed that Traps D and E could specifically bind hIGF-I ligand with high affinity; the interaction of Trap E with hIGF-I was modestly stronger compared to Trap D.

TABLE II

Results of initial SPR screening using multi-cycle analyses (n = 4). Shown are calculated equilibrium dissociation constants ($K_D$ +/− SE) for binding between Trap proteins and ligands. The results clearly demonstrate Trap specificity for hIGF-I compared to insulin. The Fc-sIGF-IR fusion showed an affinity for hIGF-1 approximately 1000-2000 times higher than its affinity for human insulin.

| Trap | hIGF-1 | Human insulin |
|---|---|---|
| B (control) | 8 +/− 0.1 nM | 10 +/− 2 µM |
| D | 13 +/− 0.2 nM | 16 +/− 4 µM |
| E | 6 +/− 0.2 nM | 14 +/− 8 µM |

Figure 14:
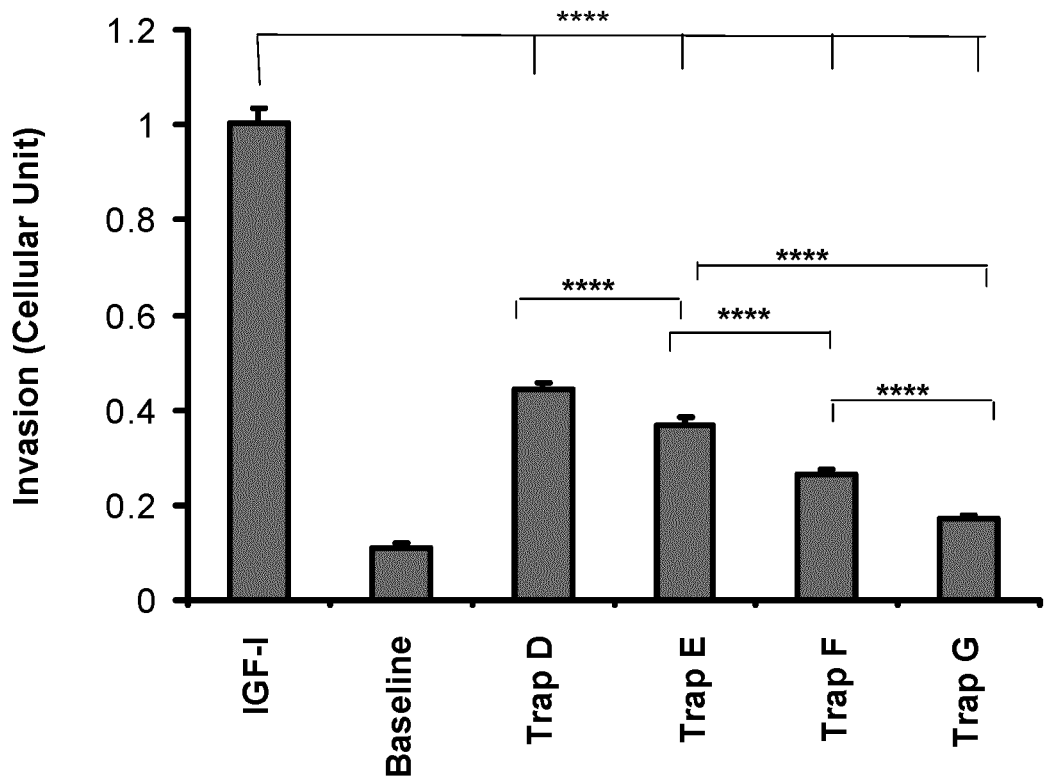
FIG. 14 shows in (A), the effect of Traps D, E, F and G on tumor cell invasion at 48 hours; **** indicates p<0.0005. (B) shows a time course analysis for the effect of Traps D, E, F and G on tumor cell invasion: blue line (♦) is IGF-I, green line (■) is baseline (no IGF-I), light brown line (♦) is Trap ID, dark green line (▲) is Trap E; red line (■) is Trap F; light blue line (●) is Trap G.
Figure 14:
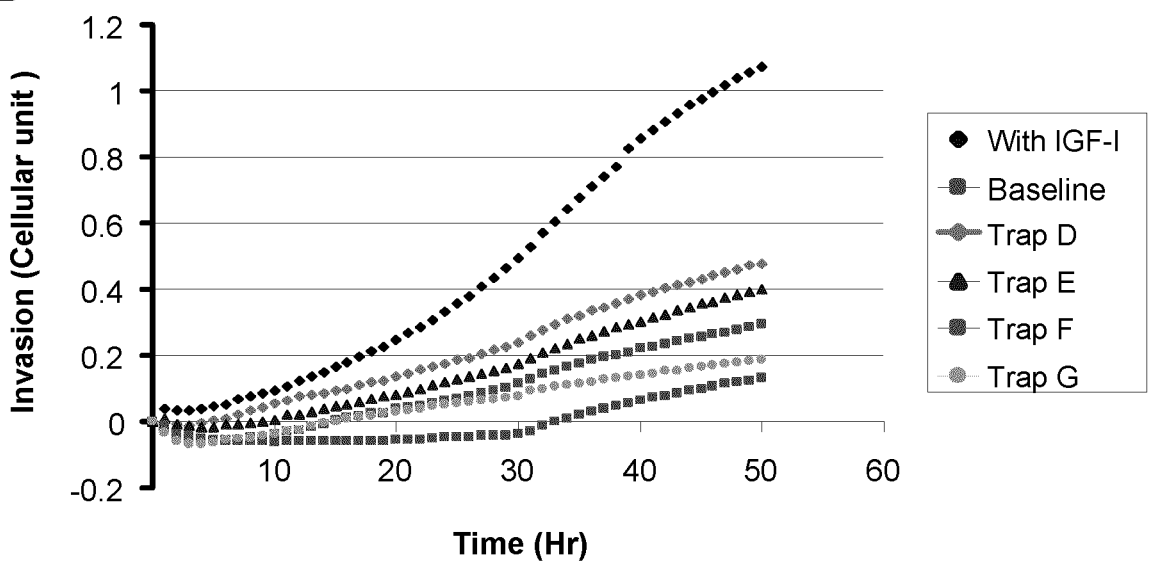

Protein A-purified Traps F and G (with D as control) were flowed over ligand-immobilized surfaces and exhibited low nanomolar affinities for hIGF-I as well as mIGF-I and hIGF-II (Table III). It was also noted in these multi-cycle trials that Trap F had a slower dissociation rate constant ($k_d$ ~4.3×10$^{-4}$ s$^{-1}$) compared to Trap D ($k_d$ ~8×10$^{-4}$ s$^{-1}$), and Trap G was even slower to dissociate ($k_d$ ~1.5×10$^{-4}$ s$^{-1}$) compared to Trap F. Finally, endotoxin-free versions of Traps F and G (i.e. Traps H and I, respectively, with E as control) were immobilized for SPR analysis. While Traps E (FIG. 14), H, and I shared similar association and dissociation kinetics in these single-cycle trials, the nanomolar KD values estimated for Trap I were quite different than those of Traps E and H (Table III). This finding was likely due to the increased sample complexity (i.e. HMW species) of the Trap I preparation, and the very low amount of the desired species in the Trap I preparation (see FIG. 5, lanes 9 to 12; the red arrow indicates the desired species).

In general, it is noted that Traps I and E were contaminated by high molecular weight species. It is believed that this contamination accounts for the differences seen between Traps I and E and Trap H (e.g., in Table III, and elsewhere), and for much of the variability in the results reported herein. In an embodiment, therefore, Trap H represents the preferred preparation.

TABLE III

Affinity of Traps D, E, H and I for IGF-IR ligands. Shown are the calculated equilibrium dissociation constants ($K_D$ +/− SE) for binding between purified Traps and IGF-IR ligands.

| Trap | mIGF-1 | hIGF-1 | hIGF-2 |
|---|---|---|---|
| D *** | 10 −/− 0.1 nM | 11 +/− 0.1 nM | 16 +/− 0.1 nM |
| E (control) | 14 −/− 0.5 nM | 4 +/− 0.1 nM | 26 +/− 0.9 nM |
| H | 18 −/− 0.8 nM | 10 +/− 0.5 nM | 8 −/− 0.4 nM |
| I | 71 +/− 3 nM | 53 +/− 2 nM | 127 −/− 56 nM |

*** n = 4 in multi-cycle SPR.

In summary, the SPR results successfully demonstrated binding between the purified Trap proteins and IGF-IR ligands using two different coupling orientations. Despite variable constructs and purification protocols employed to generate different Trap preparations (i.e. "A"-"I"; see Table I), the traps exhibited mostly similar association and dissociation kinetics. However, the protein A-purified preparations containing the enriched, native tetrameric protein (e.g., Traps F and H, eluted at pH 4.0) generated better quality SPR fits as compared to preparations containing a higher relative proportion of the high molecular weight species (e.g., Traps G and I eluted at pH 3.5).

Overall, the affinity constants for Traps A-I were in agreement with similar published SPR data in which ligand binding to immobilized hIGF-IR have been reported: for example, Forbes et al. (Forbes, B. E., et al., Eur. J. Biochem. 2002; 269: 961-8) reported KD (hIGF-I→hIGF-IR)=4.5 nM and KD (hIGF-II→hIGF-IR)=23 nM; Jansson et al. (Jansson, M., et al., J. Biol. Chem. 1997; 272: 8189-97) reported KD (hIGF-I→hIGF-IR)=3.5 nM and KD (hIGF-II→hIGF-IR)=20 nM. However, surprisingly Traps E, F, H and I demonstrated similar binding affinities for both the IGF-1 and IGF-2 ligands, or in some cases, even higher affinity for IGF-2 than IGF-1. In addition, in some cases the affinity of the Trap Fc-fusion proteins for IGF-1 was higher than that of the soluble sIGFIR alone. It is noted that Trap E did not show similar affinities for both ligands as Traps H and F did; this is likely due to the purification protocol used.

Example 5

In Vitro Stability and Pharmacokinetic Properties of SIGFR Vs. Fc-sIGFR

As indicated above, no aggregation of either protein was observed after several months of storage at 4° C. or −70° C. However, we noted that functional activity of these proteins was optimal within the first 3-6 months of storage at −70° C. This may explain the reduced half life of Traps D and E observed in latter analyses (e.g., after 9 month storage, see Table V) compared to earlier ones (e.g., after 3 months storage, see Table IV).

TABLE IV

Final pharmacokinetic parameters for Traps D and E.

| Final Parameters | Units | Trap D | Trap E |
|---|---|---|---|
| Corr_XY | N/A | −0.9955 | −0.9819 |
| Tmax | hr | 0.0830 | 0.0830 |
| Cmax | µg/mL | 55.4600 | 28.5830 |
| C0 | µg/mL | 65.6995 | 35.5274 |
| Tlast | hr | 240.0000 | 240.0000 |
| Clast | µg/mL | 0.0020 | 0.0050 |
| AUCall | hr*µg/mL | 405.8128 | 98.0906 |
| AUCINF_obs | hr*µg/mL | 405.8649 | 98.2187 |
| MRTINF_obs (Half-Life) | hr | 21.8848 | 47.5156 |

(N/A: not applicable)

TABLE V

Final pharmacokinetic parameters for Traps D, E, I, and H.

| Final Parameters | Units | Trap D | Trap E | Trap I | Trap H |
|---|---|---|---|---|---|
| Corr_XY | N/A | −0.99 | −0.98 | −0.96 | −1.00 |
| Tmax | hr | 0.08 | 0.08 | 0.08 | 0.08 |
| Cmax | µg/mL | 50.83 | 28.58 | 23.98 | 67.14 |
| C0 | µg/mL | 57.05 | 35.53 | 28.21 | 77.26 |
| Tlast | hr | 240 | 312 | 288 | 312.0 |
| Clast | µg/mL | 0 | 0 | 0 | 0 |
| AUCall | hr*µg/mL | 452.38 | 107.37 | 74.86 | 541.45 |
| AUCINF_obs | hr*µg/mL | 452.40 | 107.42 | 74.89 | 541.49 |
| MRTINF_obs (Half-Life) | hr | 20.88 | 39.94 | 10.92 | 35.15 |

(N/A: not applicable)

Mice were injected intravenously with 10 mg/kg of each of the tested Trap proteins. The mice were divided into several groups of 3 mice each and blood was collected from alternate groups beginning at 5 minutes post injection and continuing at 0.33, 1, 3, 6, 12, 16 and 24 hr and daily thereafter for up to 14 days. Plasma was prepared and soluble IGF-IR levels analyzed using ELISA (R&D Systems). Data for each group of mice bled at the same interval were pooled.

Figure 15:
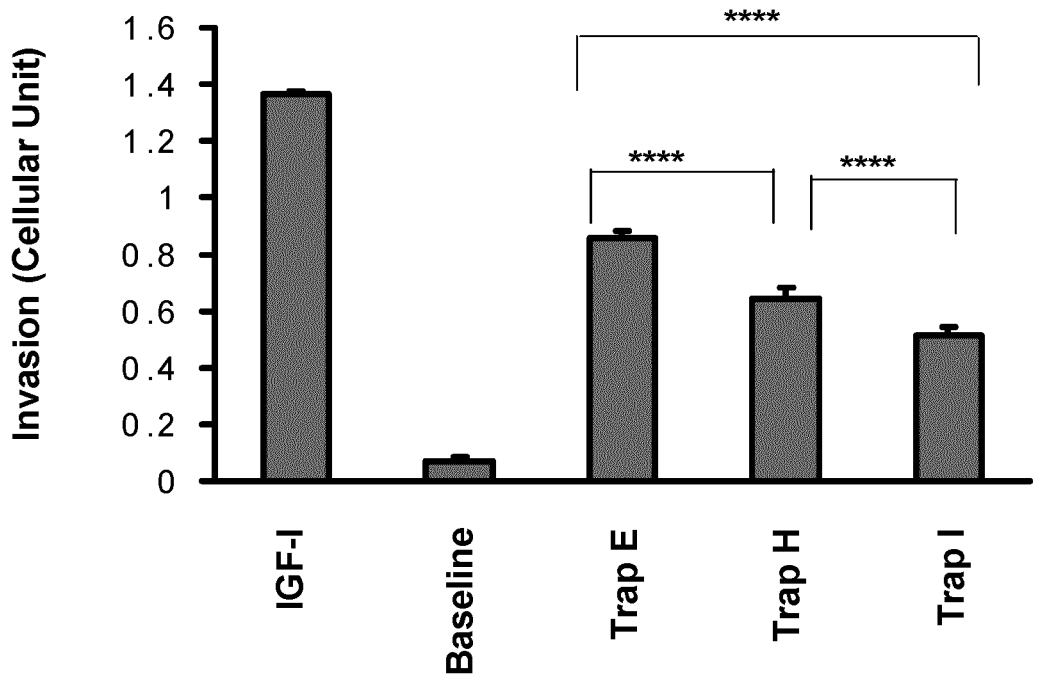
FIG. 15 shows in (A), the effect of Traps E, H and I on tumor cell invasion at 48 hours, illustrating a comparison of Trap E before and after protein A purification; **** indicates p<0.001. (B) shows a time course analysis for the effect of Traps E, H and I on tumor cell invasion: blue line (♦) is IGF-I, pink line (■) is Trap E; green line (■) is Trap H; red line (■) is Trap I; and orange line (■) is baseline (no IGF-I).
Figure 15:
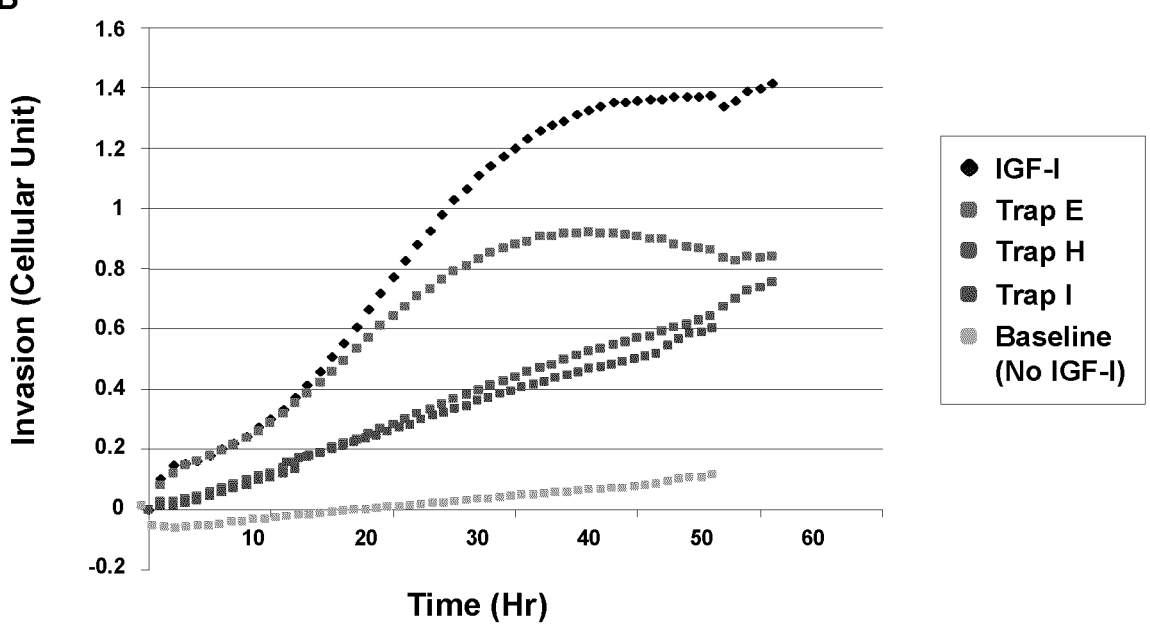
Figure 16:
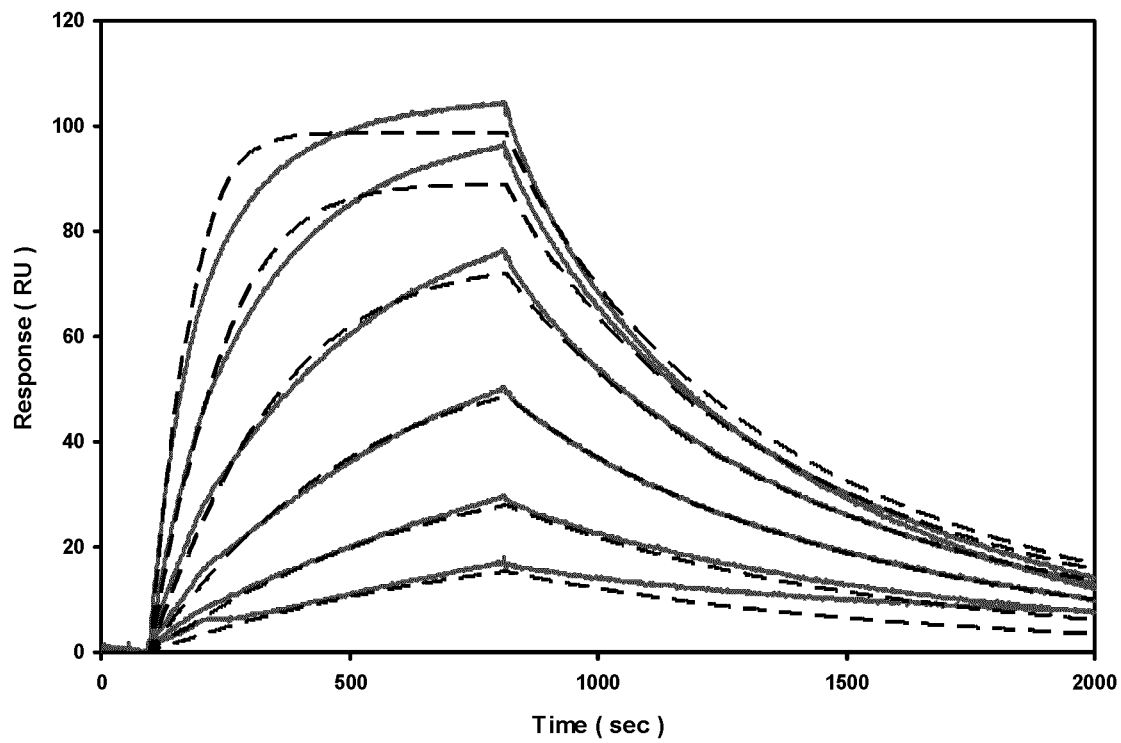
FIG. 16 shows curve fitting for a multi-cycle SPR titration. There is shown a representative analysis of experimental data (solid colored lines) to the "1:1 kinetic" model (global fit, dashed black lines) for hIGF-I (0-66 nM; 2-fold dilution series) binding to amine-coupled Trap B (9500 RU).
Figure 17:
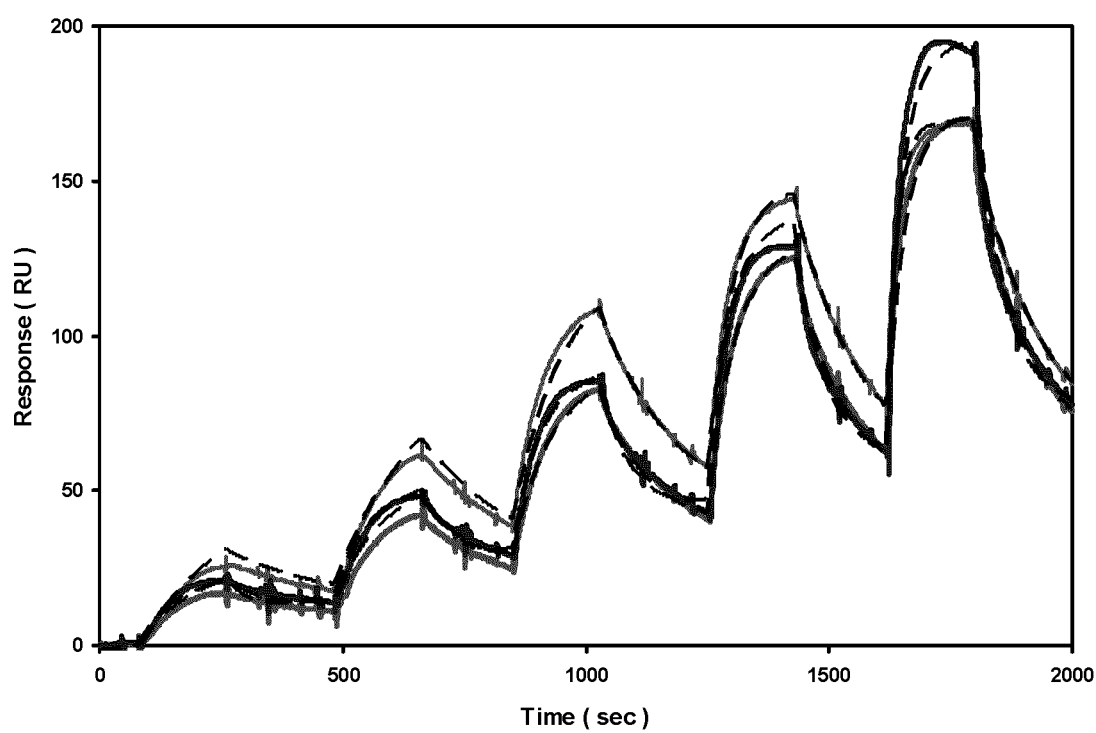
FIG. 17 shows curve fitting for a single-cycle SPR titration. There is shown a representative analysis of experimental data (solid colored lines, 0-530 nM, 2-fold dilution series) to the "1:1 titration" model (local fits, dashed black lines) for mIGF-I (green), hIGF-I (red) and hIGF-II (blue) binding to amine-coupled Trap E (6400 RU).
Figure 18:
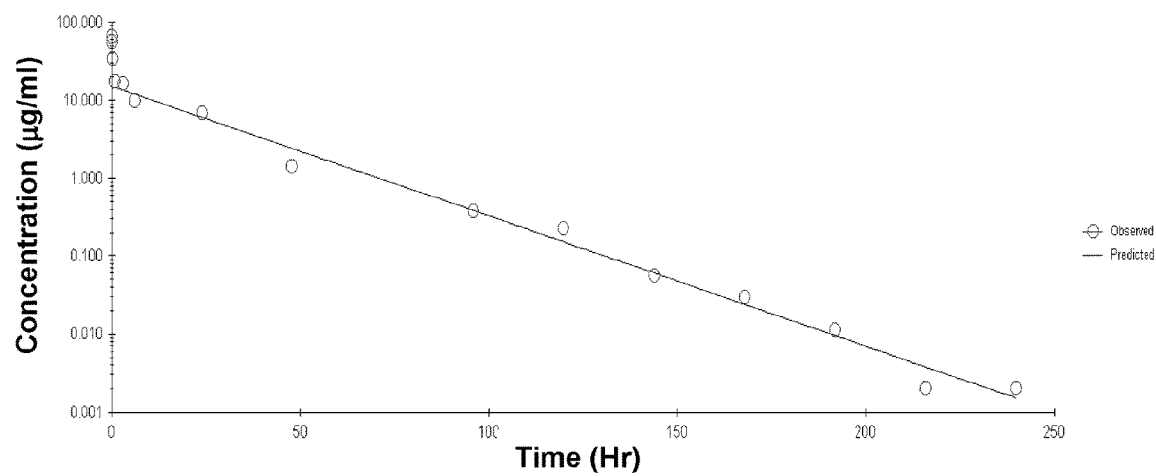
FIG. 18 shows a pharmacokinetic analysis of Traps D and E, indicating a greater than 2-fold increase in the half-life of Fc-sIGF1R (Trap E) compared to sIGF1R (Trap D). Trap D is shown in (A); Trap E is shown in (B); red circles represent observed values; and the blue line shows predicted values.
Figure 18:
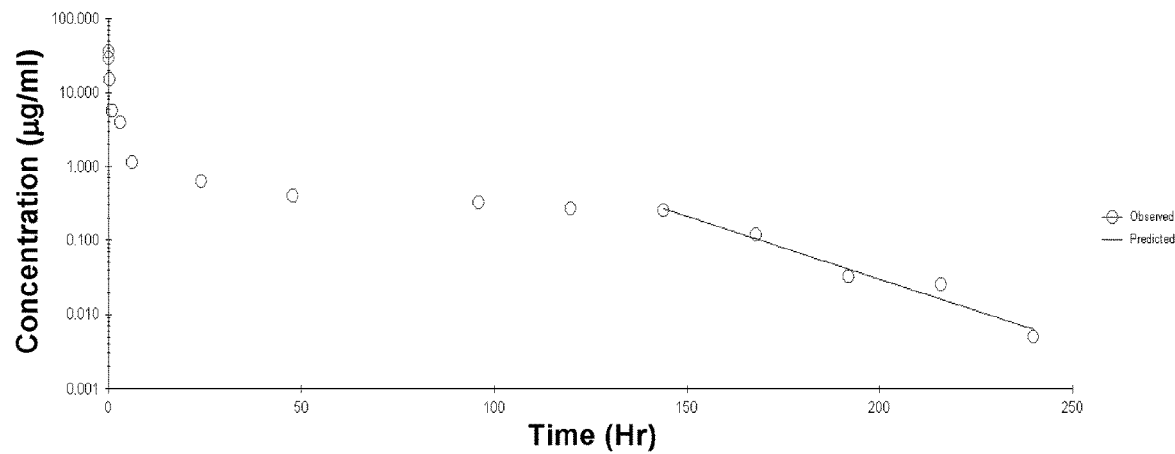
Figure 19:
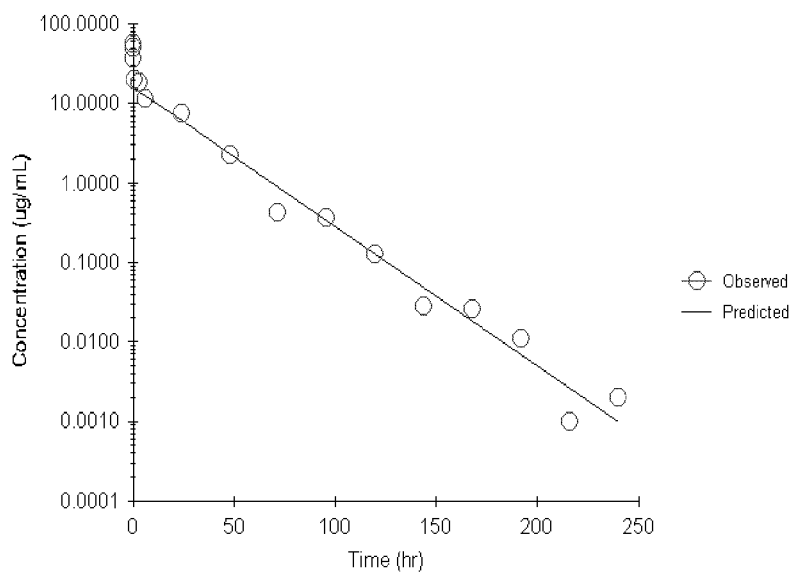
FIG. 19 shows a pharmacokinetic analysis of Traps D, E, H and I, indicating inferior in vivo performance of Protein A-purified Fc-sIGFIR enriched for HMW species. Trap D is shown in (A); Trap E is shown in (B); Trap H (pH 4.0) is shown in (C); and Trap I (pH 3.5) is shown in (D). Red circles represent observed values, and the blue line shows predicted values.
Figure 19:
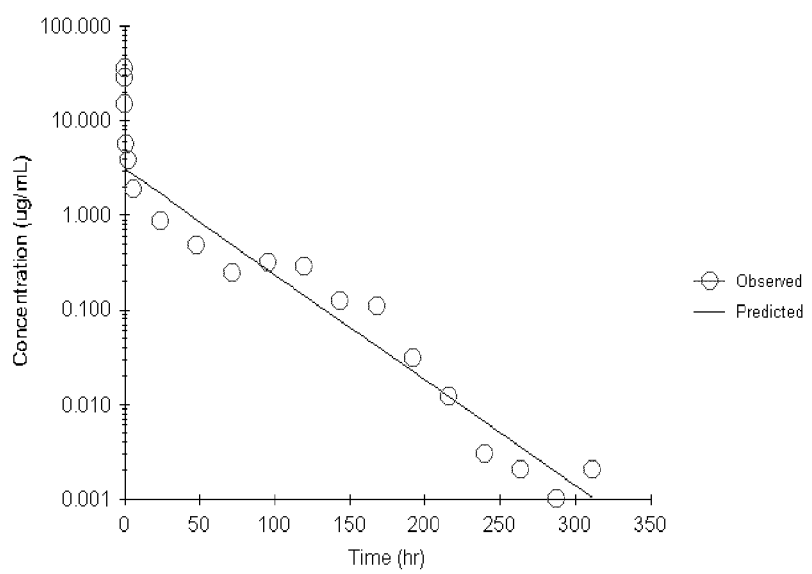
Figure 19:
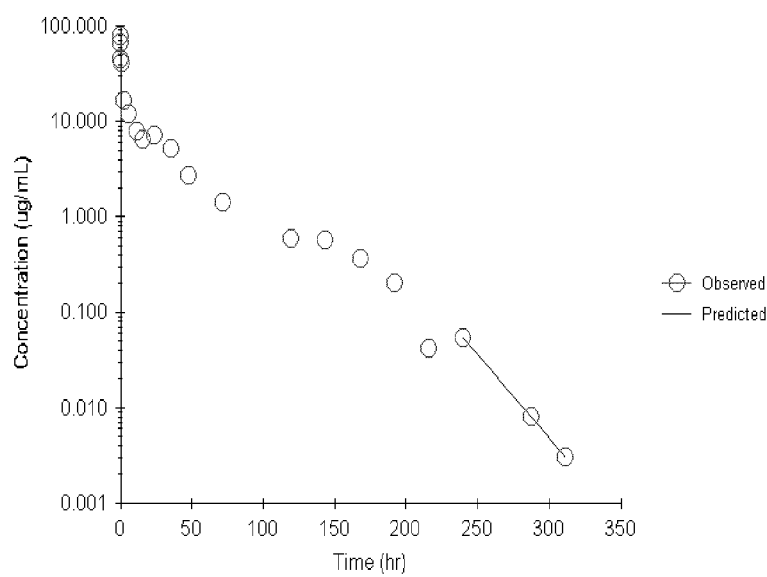
Figure 19:
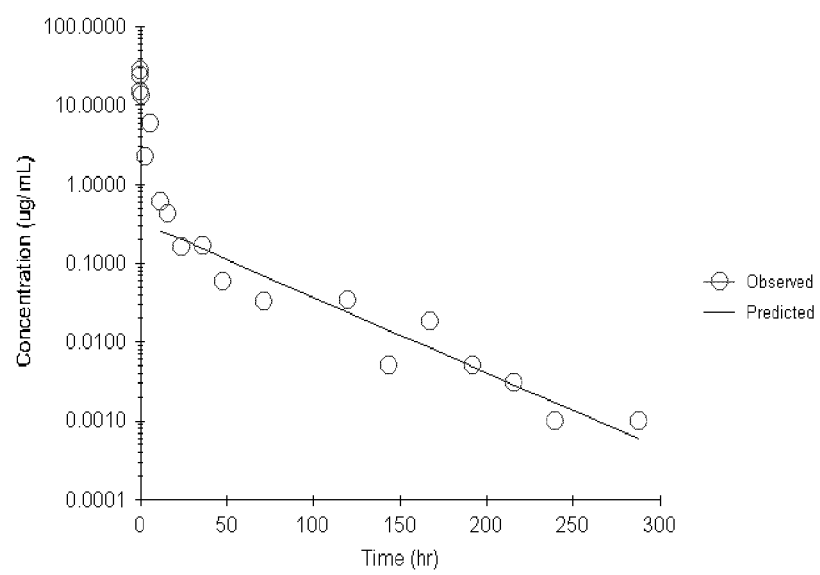

The results (FIG. 15) showed a superior in vivo stability for CHO cell-produced Trap proteins D and E as compared to His-tagged Trap protein (293 cell-produced Trap A). They also showed distinct clearance and in vivo stability profiles for Traps D and E. Pharmacokinetic analysis subsequently performed on these data showed a greater than 2-fold difference in half-life, with Trap E showing superior stability in vivo (47.5 hr as compared to Trap D at 21.8 hr; Table IV). These data confirmed that the addition of the Fc-IgG$_1$ fragment increased the in vivo stability of the Trap proteins. When endotoxin-free, protein A-purified, Fc-sIGFIR proteins (Traps H and I) were then analyzed in a similar manner, we found that the fraction eluted at pH 4.0 (Trap H, high molecular weight species depleted) had superior pharmacokinetics performance (3.5-fold increase in half life, Table V) to that eluted at pH 3.5 (Trap I, high molecular weight species-enriched) (FIG. 16).

These results show that the addition of the Fc fragment to the soluble IGF-IR significantly improved both binding affinity and the pharmacokinetic properties of the Trap protein. In vitro, Fc-sIGFIR had increased activity as compared to native sIGF-IR and the activity of Fc-sIGFIR was increased following protein A purification. Protein A purification was not effective in separating the single tetrameric Trap protein from high molecular weight species. However, elution at pH 4.0 was effective in reducing their relative proportion in the preparations. Finally, while the presence of high molecular weight species did not markedly affect the IGF-trapping activity of the proteins in vitro (with a possible slight advantage to high molecular weight proteins), they had a markedly reduced pharmacokinetic profile, with half-life values of 10 hr constituting the lowest observed for all Trap proteins tested.

Example 6

Reduction of Liver Metastases in a Mouse Model

Mice were injected with $5 \times 10^4$ lung carcinoma H-59 or colon carcinoma MC-38 cells via the intrasplenic/portal route to generate experimental liver metastases. On the following day they received the first i.v. injection of 5 mg/kg Trap H (or vehicle for control) followed by a second injection of the same dose on day 5. Mice were euthanized and metastases enumerated and sized on day 18 post tumor injection.

Results are shown in the table below and in FIG. 20. Trap H reduced the number and size of hepatic metastases for H-59 and MC-38 tumors, compared to vehicle alone, in the mouse model.

| Experimental group | Mice with hepatic metastases (incidence) | No. of metastases/liver (mean(range)) | Size of metastases (mm) |
|---|---|---|---|
| Tumor H-59 Vehicle only | 7/7 | 46 (12-80) | 0.91 |
| Tumor H-59 Trap H- 5 mg/kg | 6/7 | 22* (0-53) | 0.41 |
| Tumor MC-38 Vehicle only | 6/6 | 34 (7-119) | 0.65 |
| Tumor MC-38 Trap H- 5 mg/kg | 3/5 | 10* (0-31) | 0.79 |

*$p < 0.05$ as compared to control (Mann-Whitney test)

Figure 20:
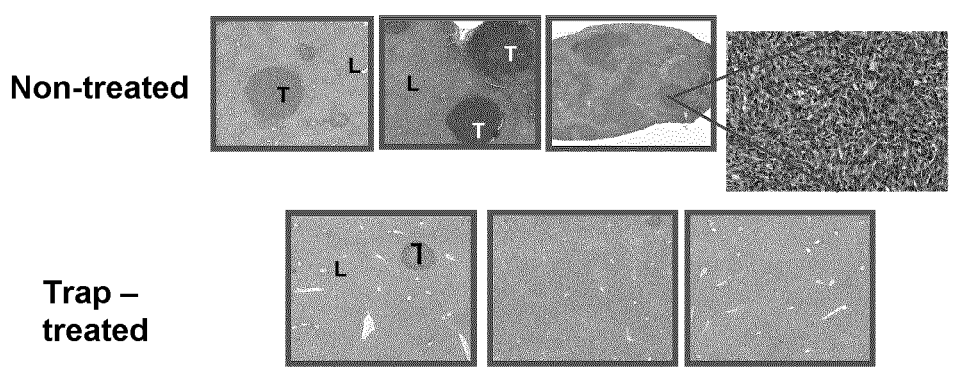
FIG. 20 shows reduced tumor volume in mice inoculated with colon carcinoma MC-38 cells and treated with IGF-Trap H. Representative H&E stained formalin fixed paraffin embedded sections of livers derived from colon carcinoma MC-38-injected mice 19 days post tumor injection are shown. Top row: livers from mice not treated with IGF-Trap H (Non-treated); bottom row: livers from mice treated with IGF-Trap H (Trap-treated); L indicates liver; T indicates tumor; Mag-×20-50, inset—×400. The far right panel in the top row shows an expanded view (×400) of the indicated metastasis.

Shown in FIG. 20 are representative H&E stained formalin fixed paraffin embedded sections of livers derived from MC-38 colon carcinoma-injected mice 19 days post tumor injection.

Example 7

An IGF-Trap Protein Inhibit IGF-IR Signaling in Tumor Cells In Vivo

Figure 21:
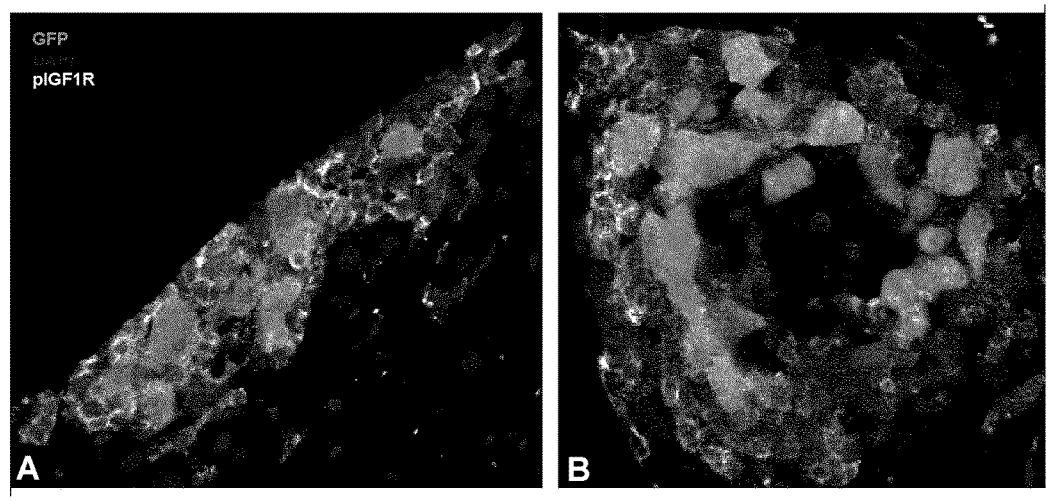
FIG. 21 shows reduced IGF-IR phosphorylation in micrometastases. C57BL6 female mice were injected intrasplenically with $10^5$ GFP-tagged H-59 cells followed by injection of 5 mg/kg IGF-Trap H (Trap-treated) or vehicle only (Non-treated) on days 1 and 3 post tumor injection (3 mice per group). Mice were sacrificed on day 6, livers removed and snap frozen and 10 μM cryostat sections prepared and immunostained with a rabbit polyclonal anti-mouse pIGF1R antibody followed by a goat anti-rabbit Alexa Fluor 647 (far-red) antibody. Sections were washed and mounted with the GOLD anti-fade reagent and analyzed with a Carl Zeiss LSM 510 Meta, confocal microscope. In (A), there are shown representative merged confocal images, as follows: A. sections from non-treated mice; B. sections from Trap-treated mice; Green fluorescent protein (GFP) is shown in green; DAPI staining is shown in blue; pIGF1R is shown in white; Images were taken at Mag. ×200. In (B), there is shown the calculated means of percent of pIGF-IR$^+$ green fluorescent tumor cells in each group (Non-treated, or Trap-treated at 5 mg/Kg, as indicated); P<0.001.
Figure 21:
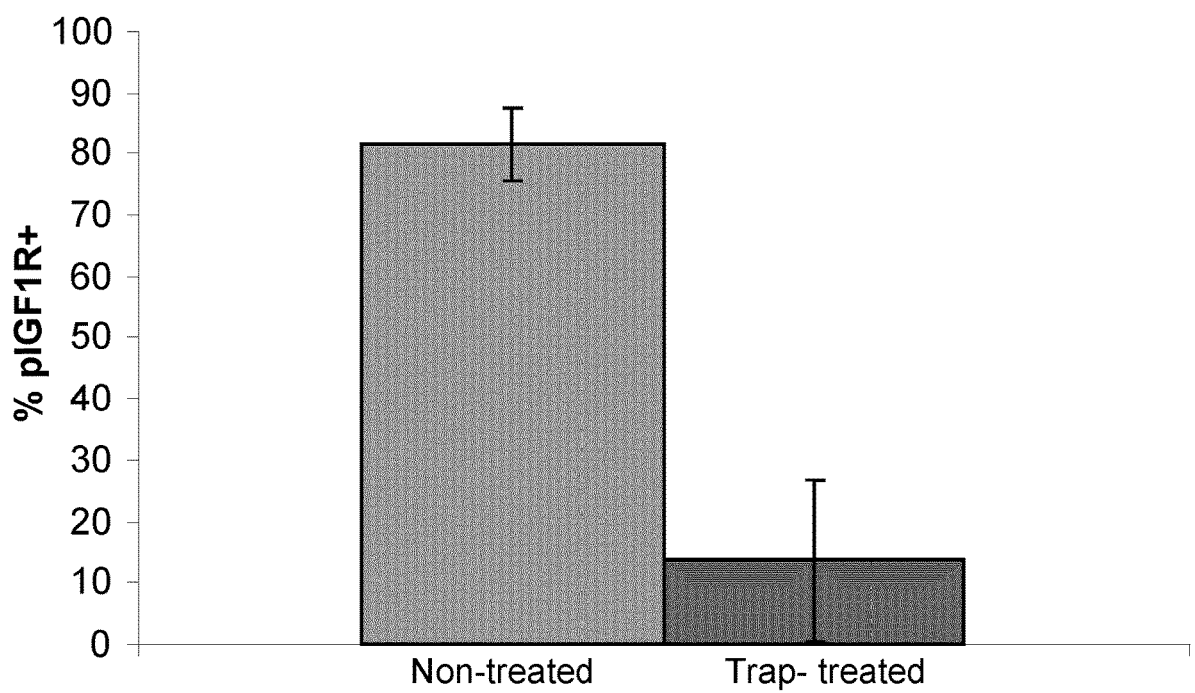

C57BL6 female mice were injected intrasplenically with $10^5$ GFP-tagged H-59 cells followed by injection of 5 mg/kg IGF-Trap or vehicle only (untreated) on days 1 and 3 post tumor injection (3 mice per group). The mice were sacrificed on day 6, livers removed and snap frozen and 10 µM cryostat sections prepared and immunostained with a rabbit polyclonal anti-mouse pIGF1R antibody (ab39398-Abcam, Cambridge, Mass.) diluted 1:100 followed by a goat anti-rabbit Alexa Fluor 647 (far-red) antibody (Molecular Probes Invitrogen, Eugene, Oreg.) diluted 1:200. Incubations were each for 1 h at room temperature in a humidified chamber in the presence of DAPI (1:2000). The sections were washed and mounted with the GOLD anti-fade reagent (Invitrogen) and analyzed with a Carl Zeiss LSM 510 Meta, confocal microscope (Carl Zeiss Canada Ltd, Toronto, ON, Canada) equipped with a Zen image analysis station. For each treatment group, 12-16 sections were analysed and the percentage of GFP+ tumor cells that were pIGFIR positive was calculated. Representative merged confocal images are shown in FIG. 21A, and the calculated means of percent of pIGF-IR+ green fluorescent tumor cells in each group is shown in FIG. 21B. The results show that as a consequence of treatment with the IGF-Trap, activation and signalling of IGF-I receptors on the tumor cells were significantly reduced.

Example 8

An IGF-Trap Increases Tumor Cell Apoptosis In Vivo

Figure 22:
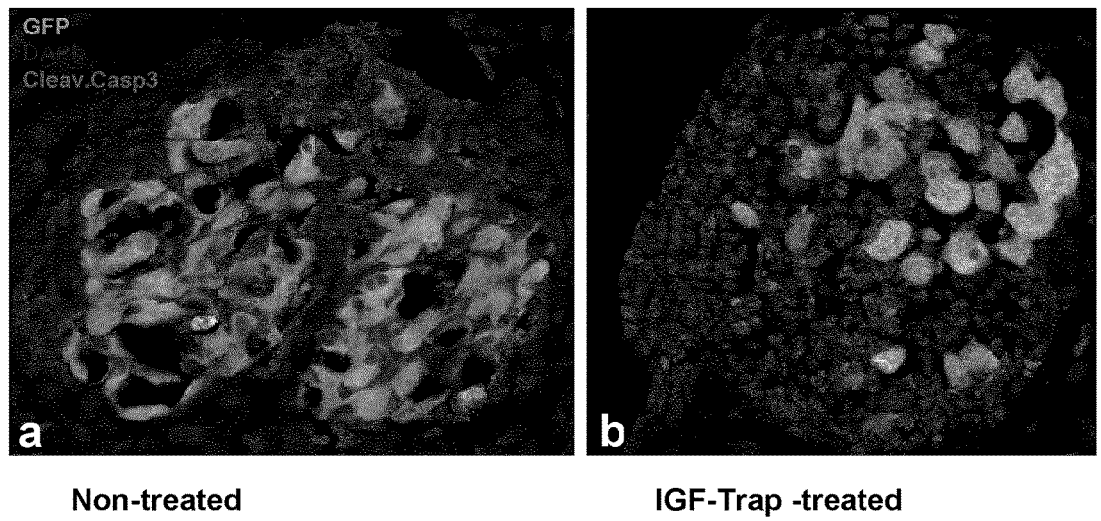
FIG. 22 shows increased tumor cell apoptosis in IGF-Trap H treated mice. Liver cryostat sections were obtained as described above for FIG. 21. Sections were incubated first with a rabbit polyclonal anti-mouse cleaved caspase-3 antibody (ab4501-Abcam) and then with a goat anti-rabbit Alexa Fluor 647 antibody. In (A), representative merged confocal images are shown, as follows: a. sections from non-treated mice (Non-treated); b. sections from Trap-treated mice (IGF-Trap-treated); Green fluorescent protein (GFP) is shown in green; DAPI staining is shown in blue; Cleaved Caspase 3$^+$ cells are shown in red; Images were taken at Mag. ×200. In (B), there is shown the calculated means of percent of cleaved-caspase 3$^+$ green fluorescent tumor cells in each group (Non-treated, or Trap-treated at 5 mg/Kg, as indicated); P<0.001.
Figure 22:
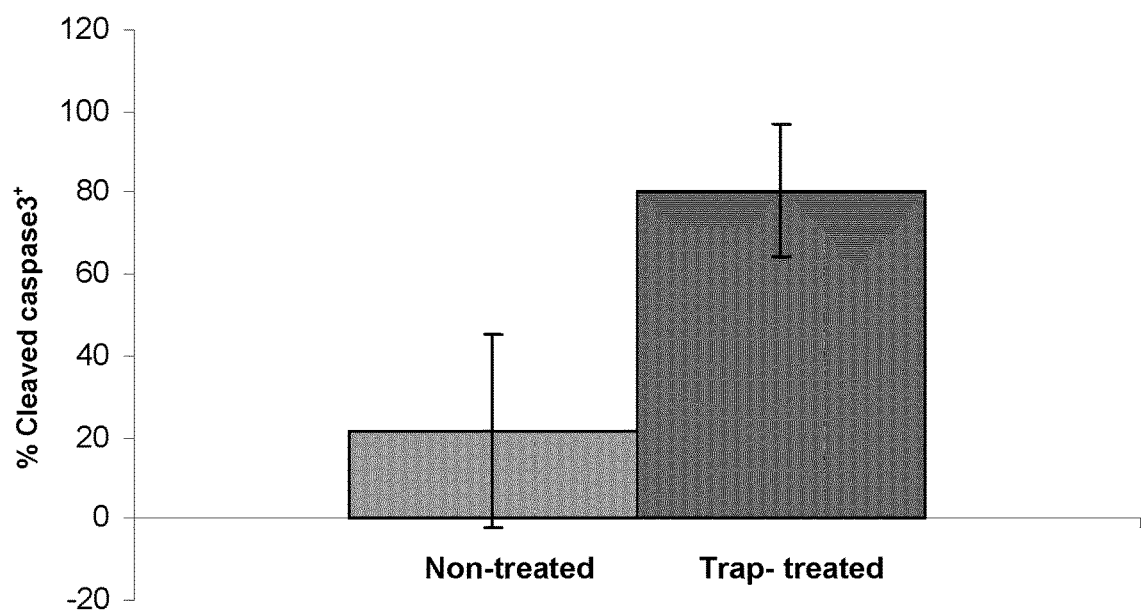

Liver cryostat sections were obtained as described above in Example 7. The sections were incubated first with a rabbit polyclonal anti-mouse cleaved caspase 3 antibody (ab4501-Abcam) diluted 1:100 and then with a goat anti-rabbit Alexa Fluor 647 antibody (Molecular Probes) diluted 1:200. Incubation and processing of the sections were as described in Example 7. For each treatment group 11-14 sections were analysed and the percentage of GFP+ tumor cells that were cleaved caspase 3 positive (an indicator of apoptosis) was calculated. Representative merged confocal images are shown in FIG. 22A, and the calculated means of percent of cleaved-caspase 3+ green fluorescent tumor cells in each group is shown in FIG. 22B. The results show that treatment with the IGF-Trap caused a significant increase in the proportion of tumor cells undergoing apoptosis.

Example 9

An IGF-Trap Inhibits Tumor Cell Proliferation In Vivo

Figure 23:
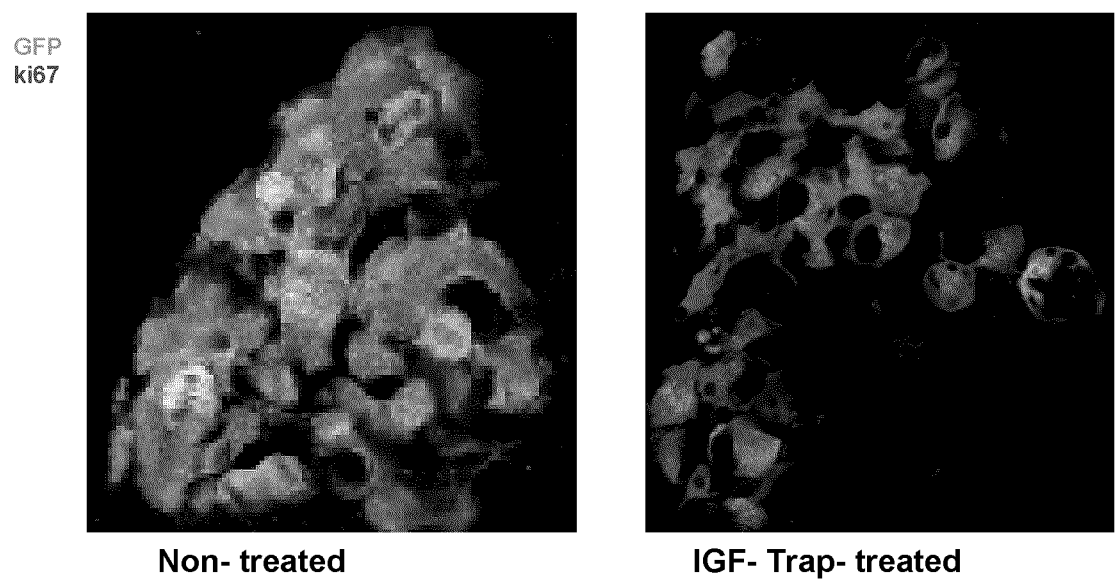
FIG. 23 shows decreased tumor cell proliferation in IGF-Trap H treated mice. Liver cryostat sections were obtained as described above for FIG. 21. Sections were incubated first with a rabbit polyclonal anti-mouse Ki67 antibody and then with a goat anti-rabbit Alexa Fluor 647 antibody. The percentage of GFP$^+$ tumor cells that were Ki67 positive (a marker of proliferation) was calculated. In (A), representative merged confocal images are shown, as follows: left panel: sections from non-treated mice (Non-treated); right panel: sections from Trap-treated mice (IGF-Trap-treated); Green fluorescent protein (GFP) is shown in green; Ki67 positive cells are shown in red; Images were taken at Mag. ×200. In (B), there is shown the calculated means of percent of Ki67$^+$ green fluorescent tumor cells in each group (Non-treated, or Trap-treated at 5 mg/Kg, as indicated); p=0.0012.
Figure 23:
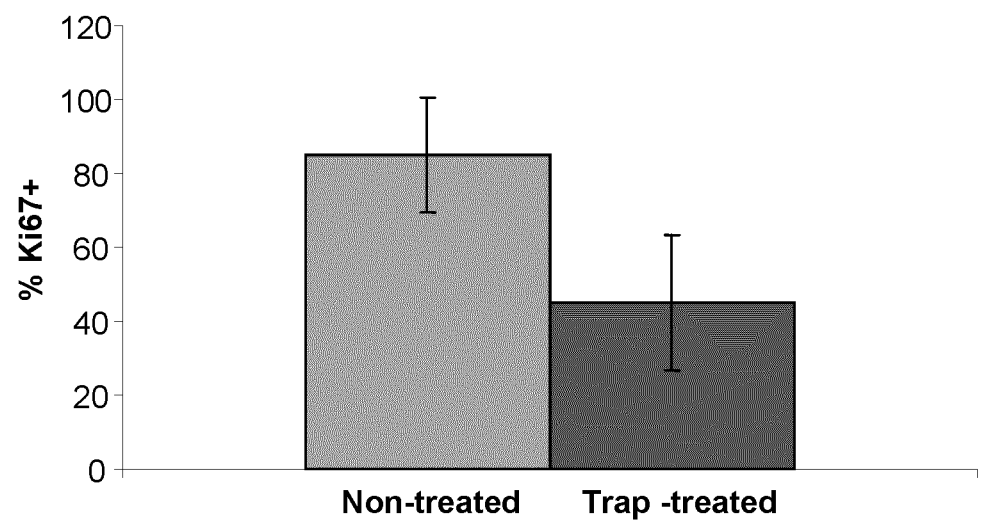

Liver cryostat sections were obtained as described above in Example 7. Sections were incubated first with a rabbit polyclonal anti-mouse Ki67 antibody (ab15580-Abcam) diluted 1:100 and then with a goat anti-rabbit Alexa Fluor 647 antibody (Molecular Probes) diluted 1:200. Incubation and processing of the sections were as described in Example 7. For each treatment group 14 sections were analysed and the percentage of GFP+ tumor cells that were Ki67 positive (a marker of proliferation) was calculated. Representative merged confocal images are shown in FIG. 23A and the calculated means of percent of Ki67+ green fluorescent tumor cells in each group is shown in FIG. 23B. The results show that tumor cell proliferation was significantly reduced in IGF-Trap treated mice.

Example 10

An IGF-Trap Blocks Angiogenesis In Vivo

Figure 24:
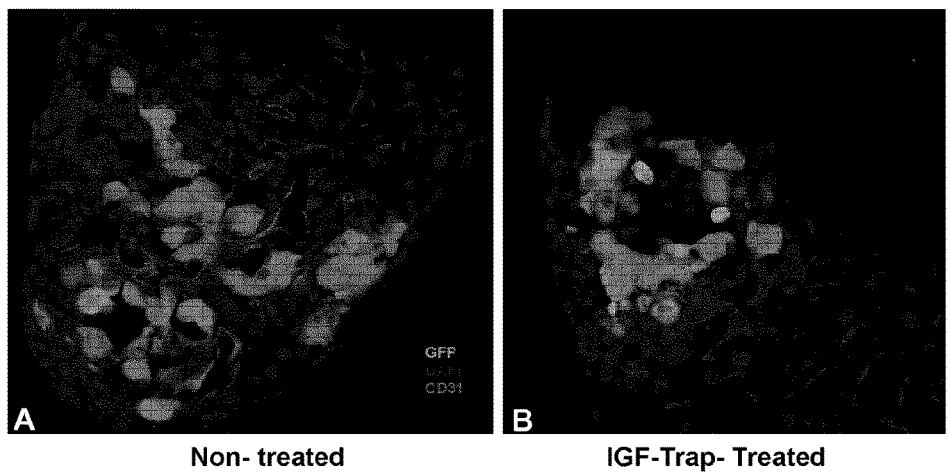
FIG. 24 shows decreased vessel count (angiogenesis) in IGF-Trap H injected mice. Liver cryostat sections were obtained as described above for FIG. 21. Sections were incubated first with a rat monoclonal anti-mouse CD31 antibody and then with a goat anti-rat Alexa Fluor 568 (orange-red) antibody. The number of CD31$^+$ endothelial cells within tumor micrometastases per field (20× objective) was counted in 16 sections per treatment group and the mean number was calculated. In (A), representative merged confocal images are shown, as follows: A. sections from non-treated mice (Non-treated); B. sections from Trap-treated mice (IGF-Trap-treated); Green fluorescent protein (GFP) is shown in green; DAPI staining is shown in blue; CD31$^+$ cells are shown in red; Images were taken at Mag. ×200. In (B), there is shown the calculated means of CD31+ cells per field in each group (Non-treated, or IGF-Trap-treated at 5 mg/Kg, as indicated); p=0.0057.
Figure 24:
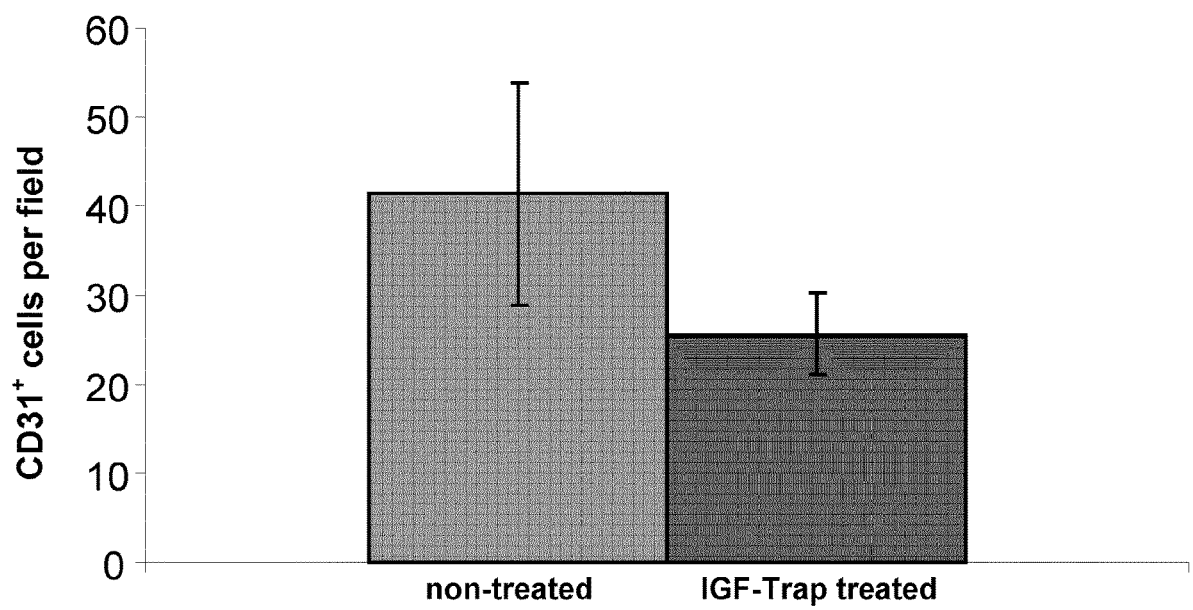

Liver cryostat sections were obtained as described above in Example 7. Sections were incubated first with a rat monoclonal anti-mouse CD31 antibody (Clone MEC 13.3, from BD Biosciences, San Jose, Calif.) diluted 1:100 and then with a goat anti-rat Alexa Fluor 568 (orange-red) antibody (Molecular Probes, Invitrogen) diluted 1:200. (FIG. 24). The number of CD31+ endothelial cells within tumor micrometastases (FIG. 24A) per field (20× objective) was counted in 16 sections per treatment group and the mean number calculated. Representative merged confocal images are shown in FIG. 24A and the calculated means of CD31+ cells per field in each group is shown in FIG. 24B. The results show that tumor-associated angiogenesis was significantly reduced in IGF-Trap treated mice.

Example 11

Tumor Growth Arrest in Mice Injected with Murine Mammary Carcinoma 4T1 Cells

Figure 25:
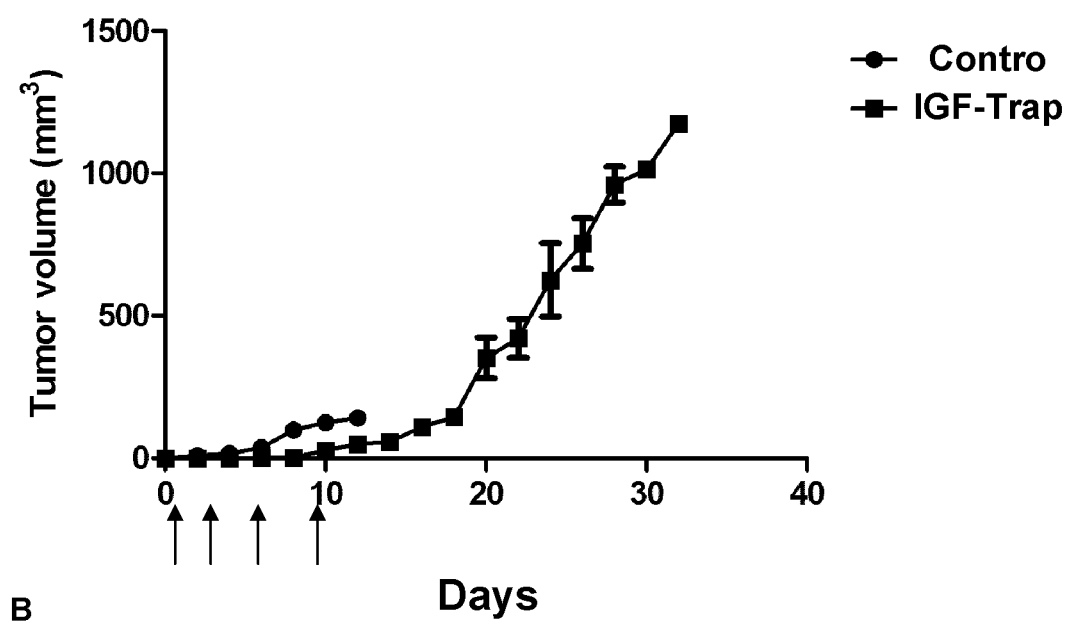
FIG. 25 shows tumor growth reduction and increase in animal survival in an orthotopic murine mammary carcinoma (4T1) model. Balb/c female mice were injected into the mammary fatpad (MFP) with $10^5$ mouse mammary carcinoma 4T1 cells. Four hours and 3 days later the treatment group received an i.v. injection of 10 mg/kg of IGF-Trap H followed by 2 injections of 5 mg/kg on days 6 and 10 post tumor inoculation (indicated by arrows in part (A)). Tumors were measured three times weekly using a caliper and the tumor volumes calculated using the formula 1/2(length×width$^2$). In (A), there is shown a graph of Tumor volume (mm$^3$) vs. Days post tumor inoculation for mice non-treated (Control) or treated with IGF-Trap (IGF-Trap), as indicated. In (B), there is shown a plot of mouse survival vs. Days post tumor inoculation for control or IGF-Trap treated, as indicated; p<0.01 using both Mantel-Cox and Gehan-Breslow-Wilcoxon tests.
Figure 25:
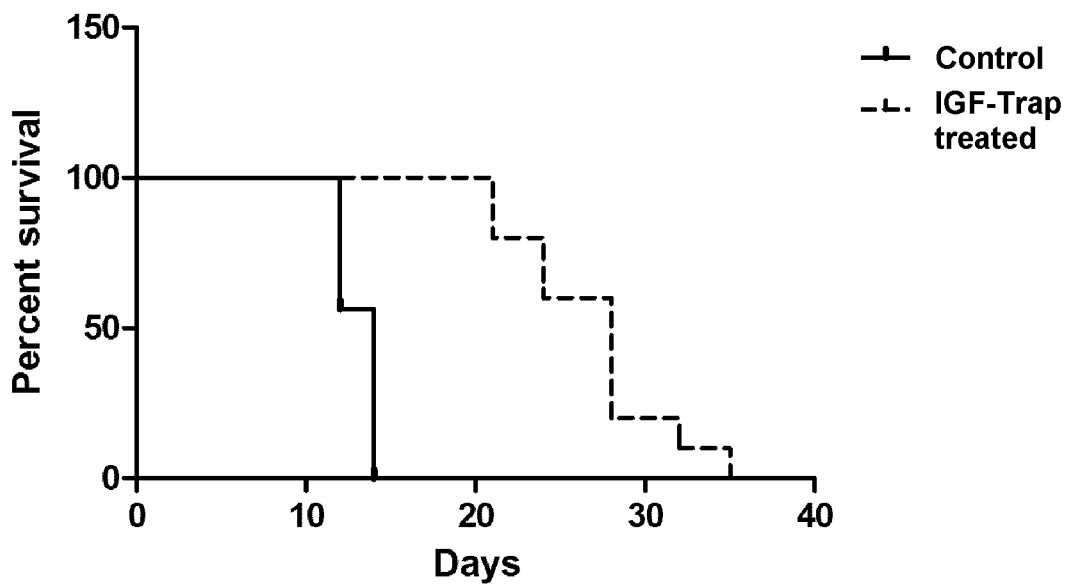

Balb/c female mice were injected into the mammary fatpad (MFP) with $10^5$ mouse mammary carcinoma 4T1 cells (Tabaries, S. et al., Oncogene 30(11):1318-28, 2011) Four hours and 3 days later the treatment group received an i.v. injection of 10 mg/kg of the IGF-Trap followed by 2 injections of 5 mg/kg on days 6 and 10 post tumor inoculation (FIG. 25A-arrows). Tumors were measured three times weekly using a caliper and the tumor volumes calculated using the formula $1/2(\text{length} \times \text{width}^2)$. In all non-treated mice tumors grew rapidly resulting in death of all mice by day 14 post tumor injection (FIG. 25 A, B) with macroscopic liver metastases. In the treatment group, tumors did not significantly progress while IGF-Trap was administered. Tumor growth was seen only after cessation of treatment (day 14 onward, FIG. 25A). Mice survived up to 35 days post tumor injection (FIG. 25B) ($p<0.01$ using both Mantel-Cox and Gehan-Breslow-Wilcoxon Tests).

Example 12

Figure 26:
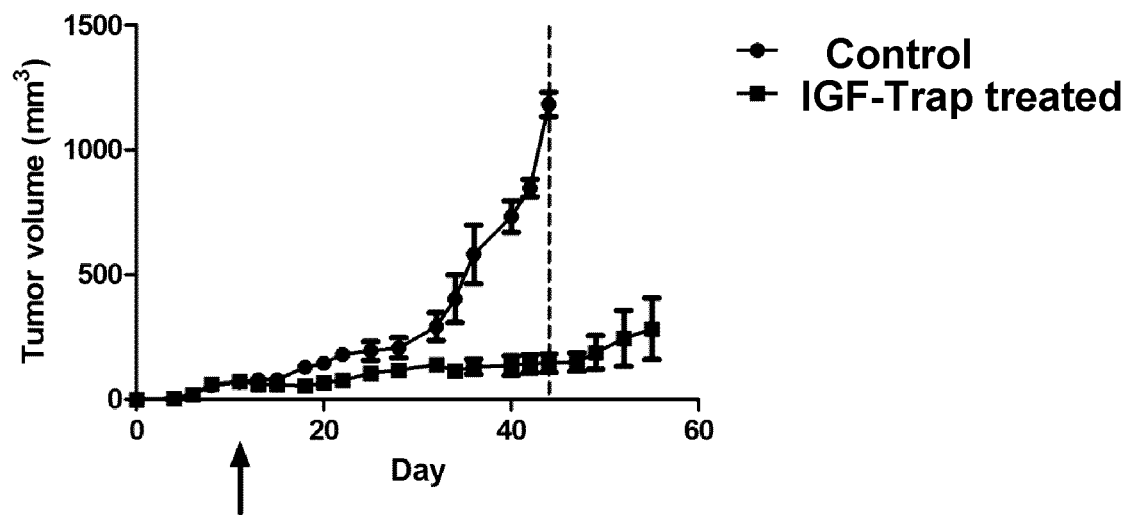
FIG. 26 shows tumor growth inhibition in IGF-Trap-treated mice orthotopically implanted with human breast cancer cells. One million MD-MBA-231 human breast cancer cells were orthotopically implanted with Matrigel in the mammary fatpads of nu/nu mice. Tumors were measured three times weekly using a caliper and the tumor volumes calculated using the formula 1/2(length×width$^2$). When tumors were established (50-100 mm$^3$) (day 11, indicated by an arrow in part (A)), the animals were randomized and treated with 5 mg/kg of IGF-Trap H or vehicle (i.v.) twice weekly up to day 33. Mice in the control group were all moribund by day 44 (indicated by a dashed line in part (A)). In (A), there is shown a graph of Tumor volume (mm$^3$) vs. Days post tumor inoculation for non-treated mice (Control) or mice treated with IGF-Trap (IGF-Trap treated), as indicated. In (B), longitudinal bioluminescence imaging is shown; this was used to monitor tumors. The color scale for bioluminescence is shown at the left side of panel (B), and mice at the indicated day post tumor inoculation are shown; left panel shows non-treated mice and right panel shows Trap-treated mice. The bioluminescence was quantitated and is shown in (C) for control (Non-treated; black line) and Trap-treated (red line) mice. The unit of measurement p/sec/cm$^2$/sr stands for photons per second per cm$^2$/steradian.
Figure 26:
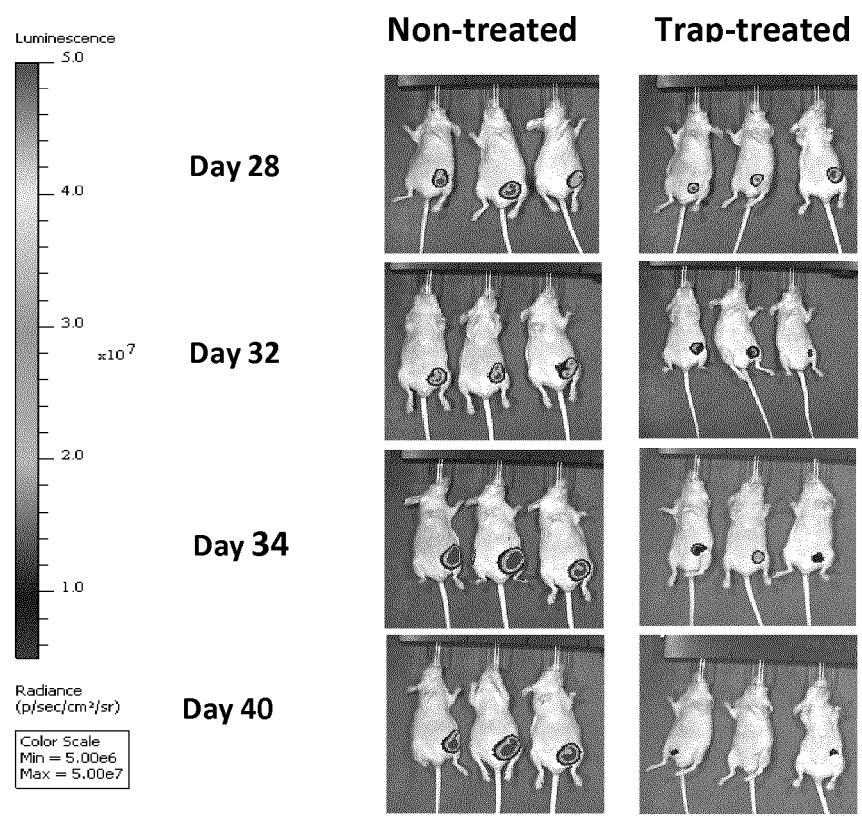
Figure 26:
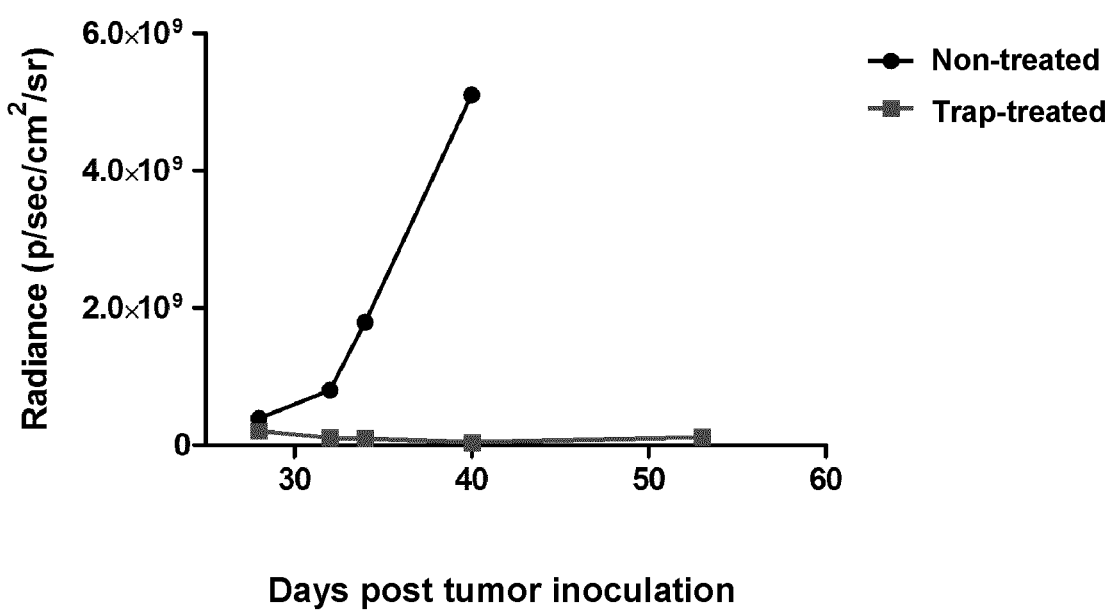

Growth Arrest and Regression in Nude Mice Injected with Human Breast Carcinoma MDA-MB-231 Cells One million MD-MBA-231 human breast cancer cells (Mourskaia, A. A. et al., Oncogene, 28(7): 1005-15, 2009) were orthotopically implanted with Matrigel in the mammary fatpads of nu/nu mice. Tumors were measured three times weekly using a caliper and the tumor volumes calculated using the formula $1/2(\text{length} \times \text{width}^2)$. When tumors were established (50-100 mm$^3$) (FIG. 26A-day 11-arrow), the animals were randomized and treated with 5 mg/kg of IGF-Trap or vehicle (i.v.) twice weekly up to day 33. Mice in the control group were all moribund by day 44 (FIG. 26A-dashed line). In the IGF-Trap group, growth of all tumors was arrested during treatment. In some animals, tumors began to progress 20 days after administration of the last treatment (Day 55). All treated mice survived at least until day 70 (study still ongoing). Complete regression (cure) was seen in 1/5 mice and tumor stabilization (growth arrest) was seen in 1/5 mice. In all the mice, tumors were also monitored using longitudinal bioluminescence imaging showing an increase in bioluminescence signal intensity in the control group and a marked reduction in signal in the IGF-Trap treated group over time (FIG. 26B).

Based upon efficacy in cell-based assays, high-affinity ligand binding to both the IGF-1 and IGF-2 ligands, in vivo stability, and efficacy in mouse tumor models, the Fc-Trap proteins described herein are attractive therapeutic candidates for the treatment and/or prevention of cancer, metastasis and/or angiogenesis-associated disorders.

Example 13

Rational Design of sIGF1R-ed-Fc Variants for Eliminating High-molecular-weight (HMW) Species As shown above, fused forms of sIGF1R to Fc IgG1 or IgG2 (sIGF1R-hFc-IgG1 or sIGF1R-hFc-IgG2, respectively) expressed in CHO cells displayed about 50% of disulphide linked high molecular weight species (HMW).

Under reducing conditions these HMW could be separated into non-disulphide linked sIGF1R-hFc.

Figure 27:
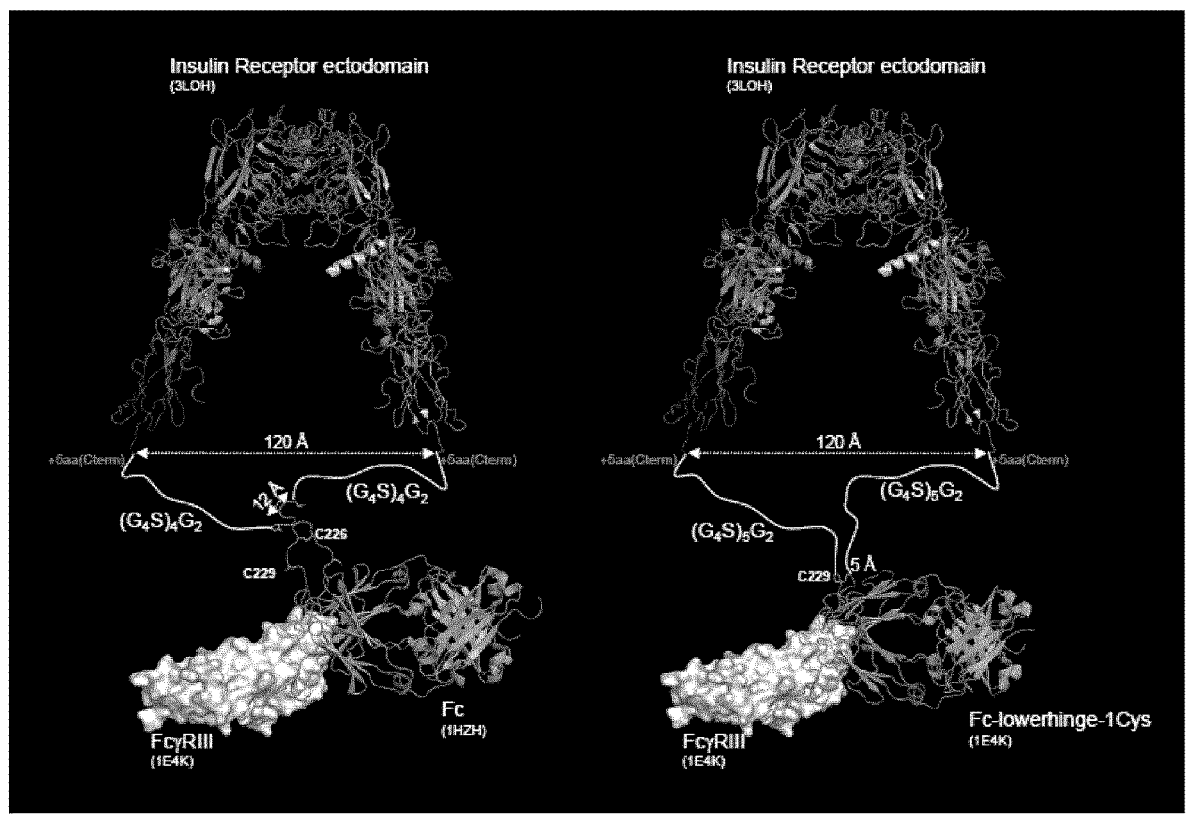
FIG. 27 shows molecular models serving as templates for the design of modified sIGF1R-ed-Fc constructs. Crystal structures for IR-ed, and for Fc complexes with FcgRIII-ed were retrieved from PDB (codes given in parentheses). The image on the left side shows that 22aa flexible linkers (white lines) utilized in the constructs Mod#2 and Mod#3 are sufficiently long to allow intra-molecular pairing of Fc fragments (cyan/green ribbons) and further allow binding to the FcgRIII-ed (surface rendering). The image on the right side illustrates the same concept for the 27aa linkers of the Mod#4 modified variant protein that uses a hinge-truncated version of the Fc.

In order to address the HMW heterogeneity of the original sIGF1R-Fc fusions having an 11 amino acid (aa) linker between the sIGF1R ectodomain (sIGF1R-ed) and the IgG-Fc fragment, we explored several possibilities. Using the crystal structure of the homologous insulin receptor ectodomain (IR-ed), we inferred that the distance between the C-termini of the sIGF1R-ed dimer should be about 120 Å (FIG. 27). Hence, given the geometrical constraints imposed by the sIGF1R-ed dimer, we hypothesized that it is unlikely that in the original 11 aa-linked construct the intra-molecular pairing of two Fc moieties can occur. The unpaired Fc chains may become available to open-ended inter-molecular associations, particularly enhanced by the presence of the available cysteine residues in the hinge region of the Fc, thereby explaining the observed HMW ladder.

To test this idea, and to design modified sIGF1R-hFc-IgG1 variant proteins, we first replaced the cysteines in the hinge region of the Fc with serine residues (variant Mod#1; see FIG. 27). As an alternative, in order to promote intra-molecular Fc dimerization by increasing the length of the linker, we effectively replaced the 11 as linker with a 22aa flexible (GS) linker, as incorporated in the modified variant protein called Mod#2 (FIGS. 27, 28). Both of these approaches (mutation of Fc hinge Cys residues, and utilization of a longer flexible linker) were combined into a third modified protein, the Mod#3 variant (FIG. 28). Finally, we attempted to reduce the HMW disulfide-linked species by truncating the Fc hinge region to retain only the lower Cys residue and accordingly further increasing the length of the flexible linker to 27aa (Mod#4; FIGS. 27, 28). In addition to the intended reduction of HMW species, the designed longer linkers (22aa in Mod#2 and Mod#3, and 27aa in Mod#4) are intended to be sufficiently long and flexible to allow not only binding to the FcRn receptor for improved pharmacokinetic properties (half-life), but also to allow simultaneous binding of the Fc portions to the FcRγIII receptor ectodomain that may confer other beneficial properties (e.g., complement function).

Materials and Methods for this and the following Examples are as follows:

Generation of pMPG-CR5 Vectors Expressing Four Modified sIGF1R-hFc-IgG1 Sequences. To generate a pMPG-CR5 vector expressing the four modified sIGF1R-hFc-IgG1 sequences, different subcloning steps were required for each construct. Briefly, the SmaI site of PUC19 was removed by SmaI-NdeI digestion to accept subsequence subcloning. In the next step, the full length of sIGF1R-hFc-IgG1 was cloned into the BamHI site of the modified PUC19. The 542nt SmaI fragment, which contains the junction of sIGF1R and hFc was removed from the sIGF1R-hFc-IgG1 sequence. This modified PUC19-sIGF1R-hFc-IgG1 vector with SmaI deleted fragment was used as backbone for further subcloning. Four modified fragments of sIGF1R-hFc-IgG1 were synthesized by Genescript. These fragments were inserted in the SmaI site of the modified PUC19-sIGF1R-hFc-IgG1 with the SmaI fragment deletion. Finally, the full length of 4 modified sIGF1R-hFc-IgG1 was excised with BamHI digestion and sub-cloned into a pMPG-CR5 expression vector to generate pMPG-CR5-sIGF1R-hFc-IgG1-Mod#1, pMPG-CR5-sIGF1R-hFc-IgG1-Mod#2, pMPG-CR5-sIGF1R-hFc-IgG1-Mod#3, and pMPG-CR5-sIGF1R-hFc-IgG1-Mod#4.

Transient Expression of the 4 Modified sIGF1R-hFc-IgG1 Proteins in a CHO-BRI-rcTA-55E3 Cell Line. CHO-BRI-rcTA cells were transfected with each of the plasmids encoding the 4 modified sIGF1R-hFc-IgG1 proteins (sIGF1R-hFc-IgG1-Mod#1, Mod#2, Mod#3 & Mod#4) using PEIpro. Five days after transfection, the expression level of the 4 modified sIGF1R-hFc-IgG1 proteins and formation of high molecular weight species were analyzed by SDS-Polyacrylamide Gel Electrophoresis (SDS-PAGE) and Western Blotting. 200 ml of each supernatant were purified using protein A columns.

Figure 29:
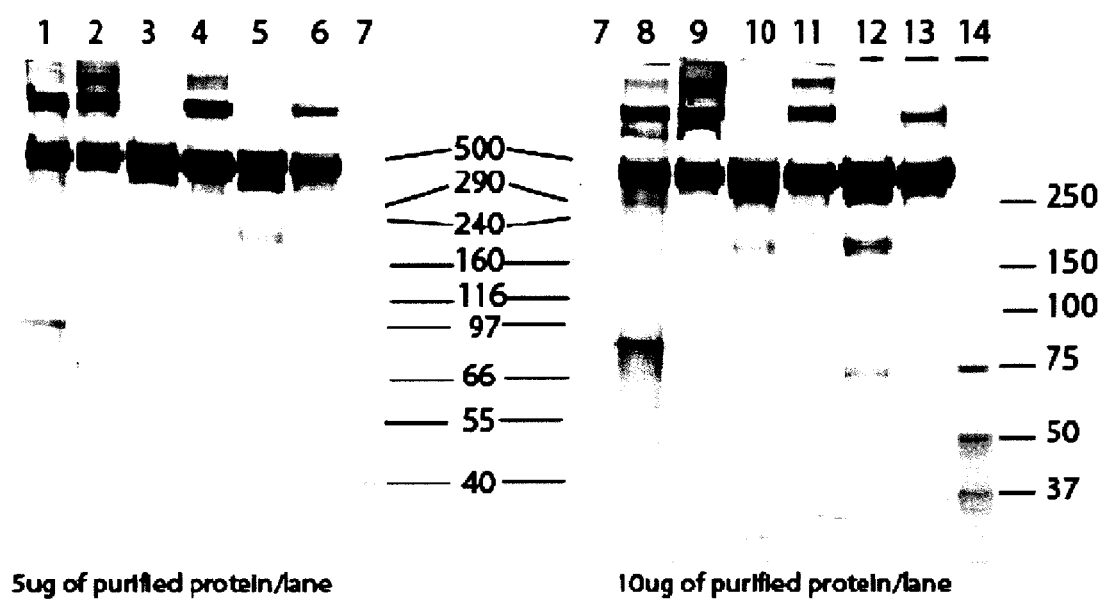
FIG. 29 shows SDS-PAGE analysis of fusion proteins. Five µg (lanes 1 to 6) and 10 µg (lanes 8 to 13) of each parental and modified sIGF1R-hFc-IgG1 protein were separated with SDS-PAGE under denaturing and non-reducing conditions. Lanes 1 & 8: sIGF1R-hFc-IgG1 (parent construct, Trap H) purified by Hydroxyapatite chromatography follow with gel filtration; lanes 2 & 9: sIGF1R-hFc-IgG1 (parent construct, Trap H) purified by protein A; Lanes 3 & 10: sIGF1R-hFc-IgG-Mod#1 purified by protein A; Lanes 4 & 11: sIGF1R-hFc-IgG1-Mod#2 purified by protein A; Lanes 5 & 12: sIGF1R-hFc-IgG1-Mod#3 purified by protein A; Lanes 6 & 13: sIGF1R-hFc-IgG1-Mod#4 purified by protein A; Lane 7: Hi-Mark Unstained HMW protein standard (InVitrogen); Lane 14: Precision Plus Protein™ Unstained Standards (BioRad).
Figure 30:
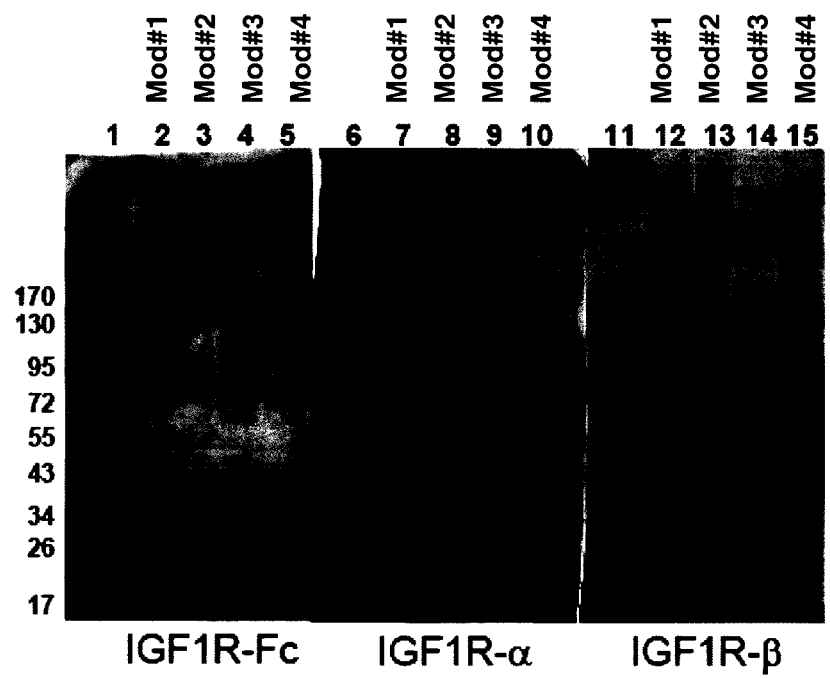
FIG. 30 shows Western blot analysis of designed modified sIGF1R-hFc-IgG1 proteins expressed in cells. Twenty ml of supernatant of CHO-BRI-rcTA-IGF1R-hFc-IgG1-Mod#1 (lanes 2, 7 & 12), Mod#2 (lanes 3, 8 & 13), Mod#3 (lanes 4, 9 & 14) and Mod#4 (lanes 5, 10 & 15) were separated on SDS-PAGE under denaturating and non-reducing conditions. The membrane blot was probed with anti-α chain (lanes 1-5), anti-β chain (lanes 6-10) or anti-Fc (lanes 11-15) antibodies. Lanes 1, 6 & 11: Ez-Run Prestained Rec protein ladder (Fisher). It is noted that β+Fc is about 80-90 kD, Fc+β+α is about 210-220 kD (monomer); and Fc+β+α+α+β+Fc is about 420-440 kD (homodimer).

SDS-PAGE and Western Blotting. To evaluate the gel migration patterns of the 4 modified sIGF1R-hFc-IgG1 proteins, and the purified proteins (5 and 10 μg of each) were separated by 4-12% SDS-PAGE. To compare the intensity or absence of HMW species, a sample of parent sIGF1R-hFc-IgG1 purified by Hydroxyapatite chromatography followed by gel filtration and a sample of parent sIGF1R-hFc-IgG1 purified by protein A were used as controls (FIG. 29). Twenty μl of CHO-BRI-rcTA-sIGF1R-hFc-IgG1-Mod#1, Mod#2, Mod#3 and Mod#4 supernatants were separated by 4-12% SDS-PAGE and transferred onto a membrane. For immunoblotting, the primary antibodies rabbit polyclonal anti-α IGF1R chain (SC-7952 Santa-cruz 1/600) or rabbit polyclonal anti-a IGF1R chain (SC-9038, Santa-cruz, 1/400) were used. Cy5-anti-Rabbit (Jackson, 1/100) was used as a secondary antibody. The IgG1-Fc portion of the sIGF1R-hFc-IgG1 fusion protein was detected with Cy5-goat-anti-Human IgG (H+L, Jackson, 1/400) (FIG. 30).

Figure 31:
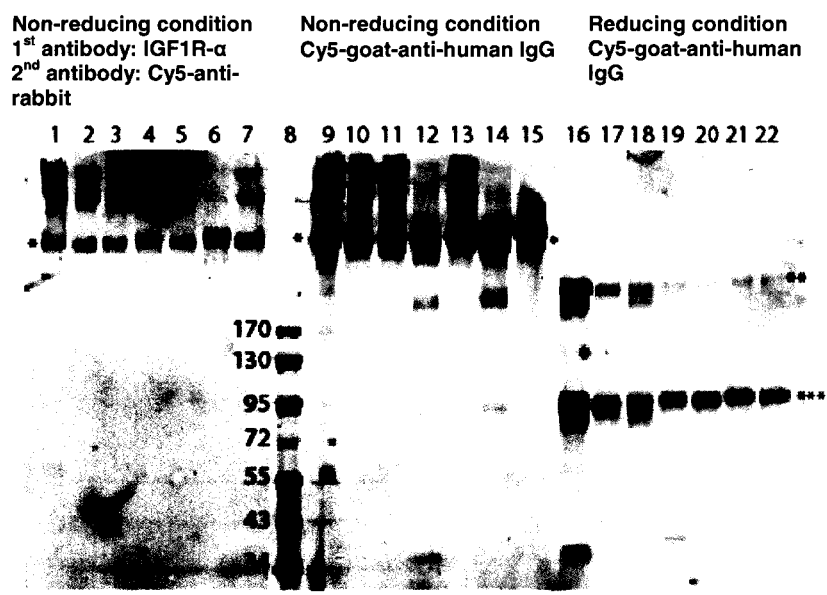
FIG. 31 shows Western blot analysis of fusion proteins. Non-purified or purified parental fusion protein (Trap H) or purified modified sIGF1R-hFc-IgG1 were the subject of SDS-PAGE under denaturing and non-reducing (lanes 1-7 & 9-15) or reducing (lanes 16-22) conditions. Membranes were probed with anti-α (lanes 1-7) and anti-Fc antibodies (lanes 9-22). The lanes shown are as follows: lanes 1, 9 & 16: supernatant of non-purified parental sIGF1R-hFc-IgG1; lanes 2, 10 & 17: parental construct purified by Hydroxyapatite chromatography followed by gel filtration; lanes 3, 11 & 18: parental construct purified by protein A; lanes 4, 12 & 19: purified sIGF1R-hFc-IgG1-Mod#1; lanes 5, 13 & 20: purified sIGF1R-hFc-IgG1-Mod#2; lanes 6, 14 & 21: purified IGF1R-hFc-IgG1-Mod#3; lanes 7, 15 & 22: purified IGF1R-hFc-IgG1-Mod#4; lane 8: EZ-Run* Prestained Rec Protein Ladder (Fisher).
Figure 31:
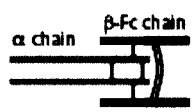
Figure 31:
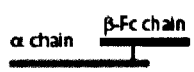
Figure 31:
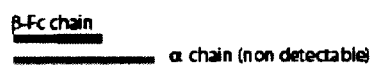

After purification of the 4 modified sIGF1R-hFc-IgG1 proteins using protein A, 200 ng of each protein was subjected to SDS-PAGE followed by Western Blotting. The sIGF1R-a chain and Fc portions of the fusion proteins were detected as described in the previous paragraph. Purified and non-purified parent constructs were used as controls (FIG. 31). In addition, a set of samples was run under reducing conditions (300 mM of DTT).

Figure 32:
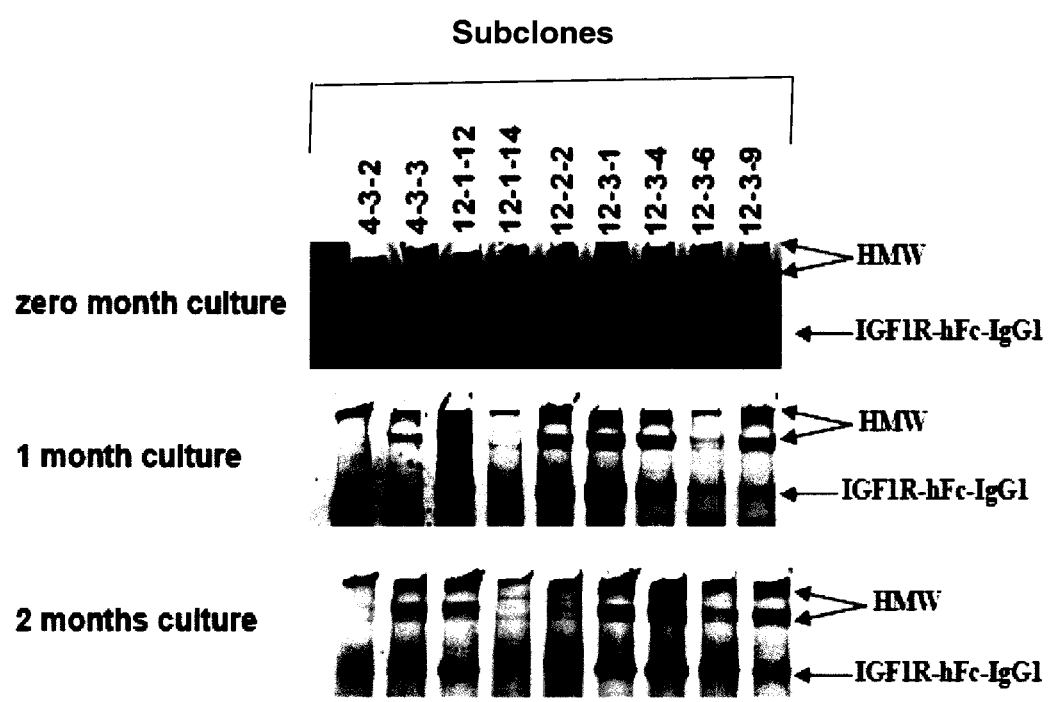
FIG. 32 shows stability testing for 9 sub-clones of CHO-Cum2-CR5-sIGF1R-hFc-IgG1 (non modified (parent) trap protein). Nine sub-clones of CHO-Cum2-CR5-sIGF1R-hFc-IgG1 were kept in culture for 2 months. At time zero, 1 month and 2 months, 7 ml of 1.5×10$^6$ cells/ml of each sub-clone in Power-CHO medium was cultured in presence of cumate for 1 day at 37° C. and 7 days at 30° C. 14 ml of supernatant of each was loaded on SDS-PAGE under denaturing, non-reducing conditions.

Generation of Four Industry-Grade, CHO-Cum2-sIGF1R-hFc-IgG1 Cell Lines Producing the Parent Protein. Four pools of industry grade stable cell lines expressing IGF1R-hFc-IgG1 were generated by transfection of a CHO-Cum2-L72 cell line (Mullick, A. et al., BMC Biotechnol. 6:43, 2006) with pMPG-CR5-IGF1R-hFc-IgG1 vector. Cells were kept under hygromycin selection for 3 weeks. The CHO-Cum2 pools of stable cell lines were subcloned to isolate the best producer clone. The subclones with higher expression levels were kept for 2 months in culture for stability testing. The subclone with highest stability and productivity was scaled up, CHO supernatants were concentrated, and sIGFIR-hFc-IgG1 was purified using a protein A purification method (FIG. 32).

Example 14

Engineering and Testing 4 Modified sIGF1R-hFc-IgG1 Proteins Suggested by Sequence Modeling Presence of HMW species at >1% is not recommended for manufacturing of recombinant proteins. As discussed above, unfortunately about half of the original sIGF1R-hFc-IgG1 and sIGF1R-hFc-IgG2 fusion proteins in the parent preparations were present as HMW species. Our success in removing these HMW species by adding a step of elution at pH 4.5 following protein A chromatography was partial and was not scalable because only a small fraction of protein was eluted at this pH.

To prevent or at least reduce the formation of HMW species, four modified sIGF1R-hFc-IgG1 proteins with different modifications in the junction of the sIGF1R and IgG1 sequences were constructed, as described above. There is one SmaI restriction site at 3' of sIGF1R sequence and another one at 5' end of hFc-IgG1 sequence. The presence of these two sites gave us the opportunity to modify this region by swapping any newly synthesized SmaI fragment with the original sequence. As a first step, the sequence of PUC-19 was modified to accommodate sub-cloning subsequences of full length sIGF1R-hFc-IgG1 and swapping the original sequence with the synthesized (modified) SmaI fragment. Finally the full length modified sequences were sub-cloned into a pMPG-CR5 expression vector.

In the supernatants of CHO-BRI-rCTA-55E3 cells (also referred to herein as CHO-BRI-rCTA cells, for brevity) transiently transfected with the 4 modified sIGF1R-hFc-IgG1 proteins, the proteins could not be detected by SDS-PAGE. To have enough material for SDS-PAGE analysis, 200 ml of each supernatant were then purified with protein A. The level of HMW species in parental sIGF1R-hFc-IgG1 purified by Hydroxyapatite chromatography followed by gel filtration and parent sIGF1R-hFc-IgG1 purified by protein A, was compared with the 4 modified sIGF1R-hFc-IgG1 proteins (FIG. 29). Formation of HMW species was completely absent in modified proteins Mod#1 and Mod#3, in which both cysteines in the core hinge were replaced with serines. HMW species were still present in sIGF1R-hFc-IgG1-Mod#2 and Mod#4 proteins, but their level of production was lower than in the parental form of the proteins (sIGF1R-hFc-IgG1). However, two low molecular weight (LMW) bands with MW about 80-90 kDa and 210-220 kDa were found in gels of Mod#1 and Mod#3, and to a lesser extent in gels of Mod#4. In addition to these LMW bands, a protein of about 30 kD was also detected in the SDS-PAGE profile for Mod#1.

Western Blots on supernatants containing the 4 modified sIGF1R-hFc-IgG1 constructs were performed using antibodies against the α and β chains of IGF-IR and the Fc portion of the fusion proteins (FIG. 30). No HMW bands were detectable in supernatants containing Mod#1 and Mod#3. The level of HMW bands in Mod#4-containing supernatants was lower than in supernatants containing the parent form of the fusion protein. The anti-β and anti-Fc antibodies also detected some LMW species. On the basis of the Western blot results, the band of approximately 80-90 kD appears to be of a single β chain fused to Fc and the band of 210-220 kDa is probably a monomer form of sIGF1R-hFc-IgG1 (Fc+β+α chain). The intensity of these LMW forms in the supernatant of CHO cells was approximately half of the tetramer+Fc protein as assessed by Western Blot.

To determine the abundance of these bands in the purified protein fractions and compare it to levels obtained with the parental construct, non-purified and purified parental sIGF1R-hFc-IgG1 and the 4 modified sIGF1R-hFc-IgG1 proteins were analyzed by Western Blotting using anti-α subunit and anti-Fc antibodies (FIG. 31). Under non-reducing conditions, the parental sIGF1R-hFc-IgG1, non-purified or purified fractions showed a similar pattern and no LMW species were detected. However, under non-reducing conditions when anti-Fc antibody was used, LMW bands were detectable in purified preparations of the modified sIGF1R-hFc-IgG1 proteins (Mod#1 and Mod#3). The mechanism for formation of these LMW species is not clear. Perhaps replacing both Cys residues in the core hinge with Ser (as in Mod#1 and Mod#3) renders the remaining disulphide bonds of sIGF1R-hFc more sensitive to reduction in the cell culture medium. Interestingly, for Mod#4 where one cysteine (i.e., one disulphide bond) is retained, the concentration of LMW species was reduced (relative to Mod#1 and Mod#3) but some HMW species appeared in SDS-PAGE gels and Western blots. Notably however, the levels of LMW bands significantly decreased following fractionation of protein A columns, suggesting that they have different binding dynamics (e.g., affinity) to protein A and could likely be eliminated by protein A purification.

Under fully reducing conditions, when all disulphide bonds are reduced, HMW species should appear as two bands, one at 130-140 kDa corresponding to the full length α-chain (not detectable with anti-Fc antibody) and another at 80-90 kDa corresponding to the β subunit-Fc fusion protein. However, a band of 210-220 kDa (corresponding to a sIGF1R-hFc-IgG1 monomer) was detectable in the gels. This finding suggested that disulphide bonds formed between the α-chain and the β-Fc fusion protein of each monomer were more resistant to reduction by DDT at 300 mM than the disulphide bonds between α-chains of two separate monomers. A low MW band of approximately 30 kDa was also detected in the non-purified protein fraction and in Mod#1 and probably represents a truncated form of the Fc-β-fusion protein.

Although a rational design was employed in constructing all 4 modified proteins, results indicated that only 2 of the new constructs produced proteins that did not form HMW species. For example, in the case of modified protein Mod#2, in which a longer linker was introduced but the hinge Cys residues were not substituted, HMW species could still be observed, albeit at a lower level than in the parent protein. This finding suggests that, while some intra-molecular Fc dimers may have been established in the Mod#2 variant (as postulated), there was still a significant level of Fc protein available for inter-molecular association. On the other hand, the fact that the Cys-Ser substitutions in the hinge domain of Fc resulted in complete elimination of HMW species in modified proteins Mod#1 and Mod#3, together with the finding of an intermediate level of HMW species in Mod#4 that retained only one of the two hinge Cys (FIGS. 29, 30, 31) indicates that hinge Cys residues are indeed involved in promoting inter-molecular oligomerization, as predicted by our molecular modelling. Interestingly, the 30 kDa protein originating from the Fc fragment was seen only in Mod#1 and not in Mod#3. This may indicate that the intra-molecular dimerization that occurs in the Mod#3 protein due to its longer linker protects the Fc fragment from proteolytic degradation. Proteolytic cleavage appears to have occurred more readily in the Mod#1 protein where the Fc fragment is unpaired both intra-molecularly due to the short linker and inter-molecularly due to the absence of hinge cysteines.

In summary, these results suggest that the modified protein Mod#3 may be the most suitable candidate for scaled-up production of a protein which is a single band, which is desirable for development as a therapeutic.

Example 15

Generation of Industry Grade Four Modified CHO-Cum2-sIGF1R-hFc-IgG1 Cell Lines

Four pools of industry-grade stable cell lines expressing the modified sIGF1R-hFc-IgG1-Mod#1, Mod#2, Mod#3 & Mod#4 proteins were generated in the CHO-BRI-rCTA-55E3 cells. Transfected cells were kept under hygromycin selection for 2-3 weeks. The level of production of each of the modified sIGF1R-hFc-IgG1 proteins was measured in supernatants of cells cultured in presence of 1 µg/ml cumate (cum) (for induction of protein production). After 8 days in culture, protein concentrations in the conditioned media were 21, 17, 20 & 31 µg/ml for modified sIGF1R-hFc-IgG1 Mod#1, Mod#2, Mod#3 & Mod#4, respectively. Subcloning of these producing cell pools and selection of high producer clones is expected to result in increases of 3-5 fold in production levels of the selected proteins.

Example 16

Figure 33:
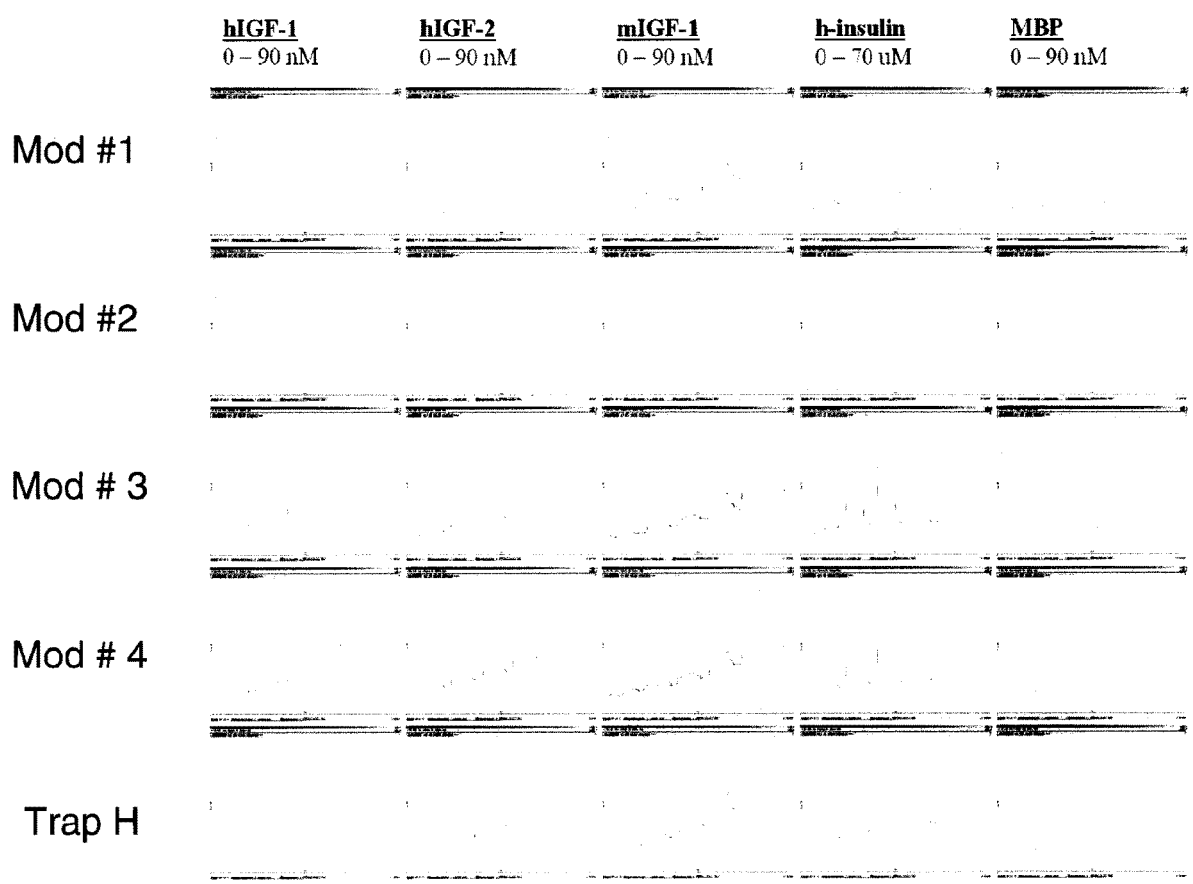
FIG. 33 shows representative single-cycle surface plasmon resonance (SPR) for the indicated ligands (hIGF-1, hIGF-2, mIGF-1, h-insulin, maltose binding protein (MBP); 3-fold serial dilutions) binding to the indicated amine-coupled sIGF1R-hFc-IgG1 proteins (Mod#1, Mod#2, Mod#3, Mod#4, Trap H; 25 µL/min×5 min association+1-10 min dissociation).

Determination of Binding Affinity for Modified sIGF1R-hFc-IgG1 Proteins Using Surface Plasmon Resonance As discussed above, modified fusion proteins Mod#1 and Mod#3 produced one major band at the expected MW for the sIGF1R-hFc-IgG1 protein and no detectable production of HMW species. In order to determine whether the binding affinity (and therefore biological activity) of these modified proteins was unchanged as compared to the parent protein, all four modified proteins (Mod#1, Mod#2, Mod#3 and Mod#4) were amine-coupled to surface plasmon resonance (SPR) sensors and rapid, single-cycle screening was used to compare the profiles of the 4 modified proteins (FIG. 33). These results showed that the 4 modified proteins (Mod #1, Mod#2, Mod#3 and Mod#4) had similar binding affinities to ligands, and that their binding affinities were also highly similar to those of Trap H (the parent trap protein, used as a positive control). Specific, dose-dependent binding responses were strongest with hIGF-1 in all cases (Table II), weaker for other ligands (hIGF-2, mIGF-1, human insulin), and no binding responses were observed with maltose binding protein (MBP; negative control).

TABLE II

Equilibrium dissociation constants ($K_D$ +/− standard error) for IGF1R ligands binding to immobilized sIGF1R-hFc-IgG1 proteins. Experimental data (5-point single-cycle SPR titrations; n = 2) was fit to the "1:1 Titration" model in the BIAevaluation software.

| Purified TRAP protein | hIGF-1 $K_D$ (nM +/− SE) | hIGF-2 $K_D$ (nM +/− SE) | mIGF-1 $K_D$ (nM +/− SE) | h-insulin $K_D$ (nM +/− SE) |
|---|---|---|---|---|
| Mod#1 | 24 +/− 1 | 195 +/− 56 | 252 +/− 21 | 6375 +/− 176 |
| Mod#2 | 17 +/− 1 | 97 +/− 9 | 172 +/− 11 | 5362 +/− 222 |
| Mod#3 | 19 +/− 1 | 169 +/− 29 | 894 +/− 89 | 29902 +/− 1694 |
| Mod#4 | 18 +/− 1 | 126 +/− 12 | 557 +/− 62 | 21695 +/− 1205 |
| Trap H (parent protein) | 11 +/− 1 | 98 +/− 8 | 540 +/− 53 | 15424 +/− 508 |

Figure 34:
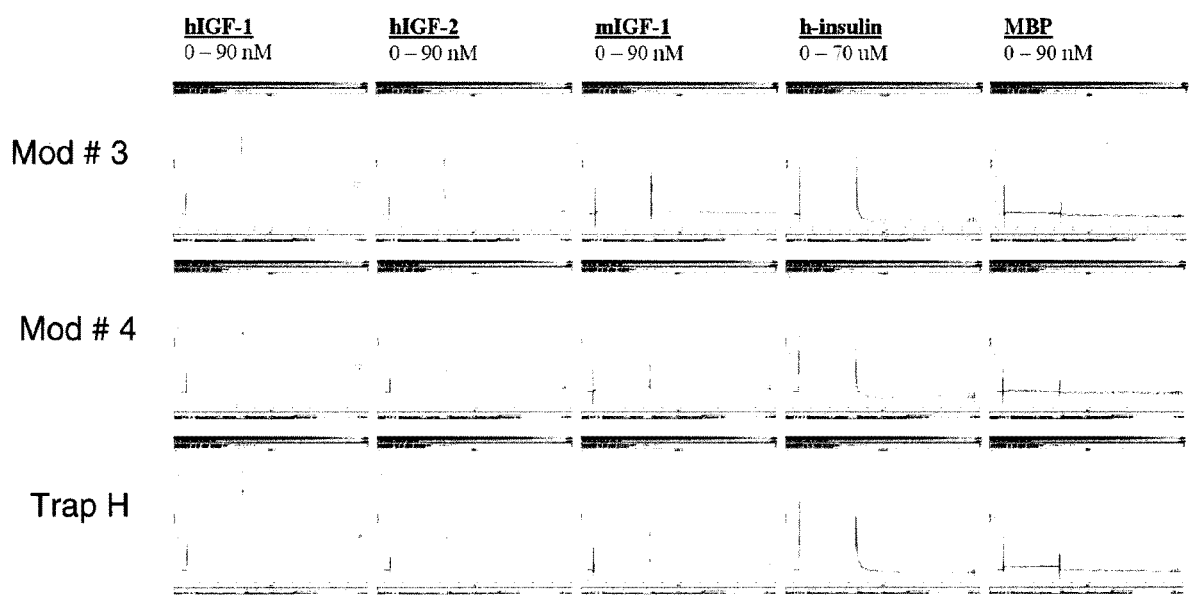
FIG. 34 shows representative multi-cycle SPR for the indicated ligands (hIGF-1, hIGF-2, mIGF-1, h-insulin, and control MBP; 3-fold serial dilutions) binding to the indicated amine-coupled sIGF1R-hFc-IgG1 proteins (Mod#3, Mod#4, Trap H; 25 μL/min×5 min association+10 min dissociation).
Figure 35:
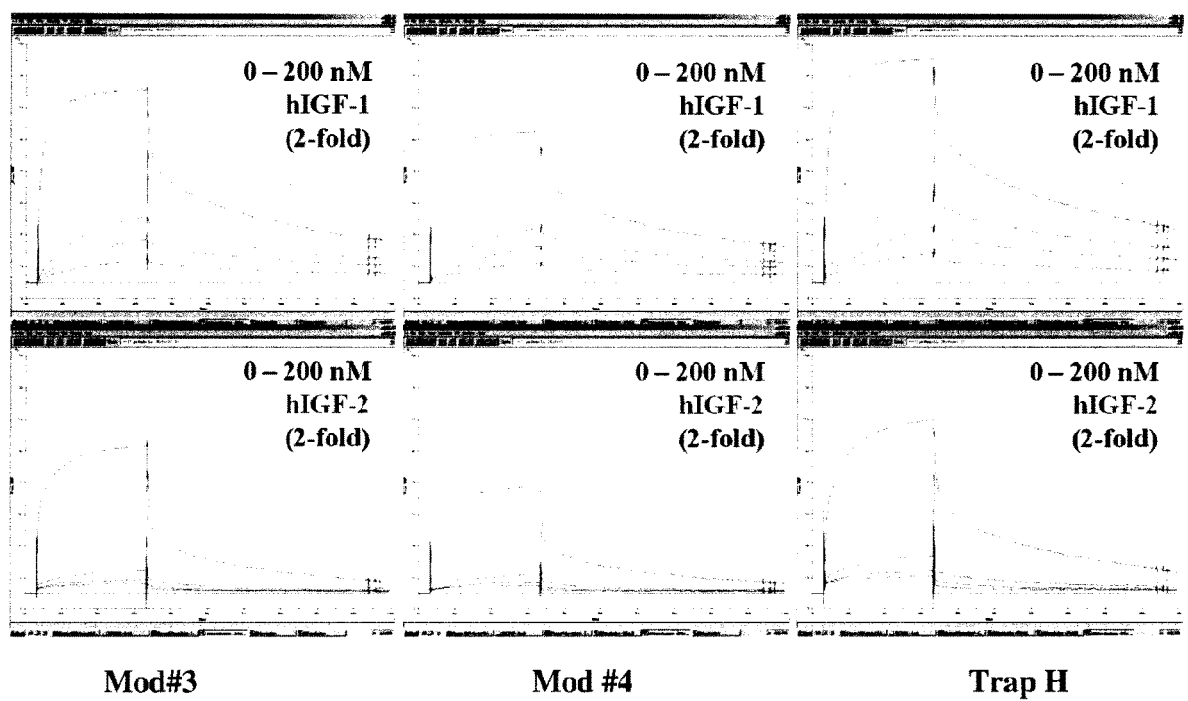
FIG. 35 shows representative multi-cycle SPR for the indicated ligands (hIGF-1, hIGF-2; 2-fold serial dilutions) binding to the indicated amine-coupled sIGF1R-hFc-IgG1 proteins (Mod#3, Mod#4, Trap H; 25 μL/min×5 min association+10 min dissociation).

Based upon SDS-PAGE analysis of the four modified proteins and the results of the rapid, single-cycle screening, we selected the Mod#3 and Mod#4 proteins for more extensive multi-cycle testing (FIGS. 34, 35; Table III). Consistent with results seen for Trap H, the binding affinity of hIGF-1 to Mod#3 and Mod#4 was highest (~6 nM; Table III); weaker binding was observed with hIGF-2 (~37 nM) and mIGF-1 (~150 nM); while binding affinity to human insulin (~7 uM) was about 100-fold lower than that to hIGF-I.

TABLE III

Equilibrium dissociation constants ($K_D$ +/− standard error) for IGF1R ligands binding to immobilized sIGF1R-hFc-IgG1 proteins. Experimental data (10-point (hIGF-1 and hIGF-2) or 5-point (mIGF-1 and h-insulin) multi-cycle SPR titrations; n = 2) was fit to the "1:1 Kinetic" model in the BIAevaluation software.

| Purified TRAP proteins | hIGF-1 $K_D$ (nM +/− SE) | hIGF-2 $K_D$ (nM +/− SE) | mIGF-1 $K_D$ (nM +/− SE) | h-insulin $K_D$ (nM +/− SE) |
|---|---|---|---|---|
| Mod#3 | 6.2 +/− 0.1 | 42 +/− 1 | 206 +/− 72 | 7575 +/− 987 |
| Mod#4 | 6.5 +/− 0.1 | 37 +/− 1 | 162 +/− 38 | 7692 +/− 1201 |
| Trap H (parent protein) | 5.7 +/− 0.1 | 32 +/− 1 | 74 +/− 15 | 5050 +/− 676 |

All references and documents referred to herein are hereby incorporated by reference in their entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A fusion protein comprising the sequence set forth in SEQ ID NO: 12 or SEQ ID NO: 16.

2. A pharmaceutical composition comprising the fusion protein of claim 1 and a pharmaceutically acceptable carrier.

3. A dimer comprising two fusion proteins defined in claim 1.

4. The dimer of claim 3, wherein the two fusion proteins are identical.

5. A method of inhibiting pathological angiogenesis in a subject having an angiogenic associated disorder, comprising administering to said subject a therapeutically effective amount of the fusion protein of claim 1.

6. The method of claim 5, wherein said angiogenic associated disorder is cancer.

7. The method of claim 5, wherein said angiogenic associated disorder is cancer metastases, colorectal carcinoma, lung cancer, breast cancer, multiple myeloma, glioblastoma multiforme, liver cancer, bladder cancer, pancreatic cancer, hepatocellular carcinoma, Ewing sarcoma, or osteosarcoma.

8. The method of claim 7, wherein said hepatic cancer is liver metastases that originated from another primary tumor.

9. The method of claim 5, further comprising administering the fusion protein in combination with another angiogenesis inhibitor and/or an anti-cancer agent.

10. A method of inhibiting tumor cell proliferation, tumor growth and/or tumor angiogenesis in a subject in need thereof, comprising administering to said subject the fusion protein of claim 1.

11. The method of claim 10, wherein said cancer is metastatic disease.

12. The method of claim 10, wherein said inhibiting tumor cell proliferation, tumor growth and/or tumor angiogenesis is associated with cancer metastases, colorectal carcinoma, lung cancer, breast cancer, liver cancer, bladder cancer, pancreatic cancer, multiple myeloma, glioblastoma multiforme, liver metastases, hepatocellular carcinoma, Ewing sarcoma, or osteosarcoma.

13. The method of claim 10, further comprising administering the fusion protein in combination with an angiogenesis inhibitor and/or an anti-cancer agent.

* * * * *